US012391939B2

(12) United States Patent
Derda et al.

(10) Patent No.: US 12,391,939 B2
(45) Date of Patent: Aug. 19, 2025

(54) GENETICALLY-ENCODED BICYCLIC PEPTIDE LIBRARIES

(71) Applicant: THE GOVERNORS OF THE UNIVERSITY OF ALBERTA, Edmonton (CA)

(72) Inventors: Ratmir Derda, Edmonton (CA); Raja Mukherjee, Edmonton (CA); Vivian Triana, Edmonton (CA)

( * ) Notice: Subject to any disclaimer, the term of this patent is extended or adjusted under 35 U.S.C. 154(b) by 1100 days.

(21) Appl. No.: 17/261,390

(22) PCT Filed: Jul. 23, 2019

(86) PCT No.: PCT/CA2019/051017

§ 371 (c)(1),
(2) Date: Jan. 19, 2021

(87) PCT Pub. No.: WO2020/019072

PCT Pub. Date: Jan. 30, 2020

(65) Prior Publication Data

US 2021/0340525 A1 Nov. 4, 2021

Related U.S. Application Data

(60) Provisional application No. 62/702,284, filed on Jul. 23, 2018.

(51) Int. Cl.
*C40B 40/10* (2006.01)
*C12N 15/10* (2006.01)

(52) U.S. Cl.
CPC .......... *C12N 15/1037* (2013.01); *C40B 40/10* (2013.01)

(58) Field of Classification Search
None
See application file for complete search history.

(56) References Cited

U.S. PATENT DOCUMENTS

| | | | |
|---|---|---|---|
| 3,982,594 | A | 9/1976 | Berthiaume |
| 4,426,466 | A | 1/1984 | Schwartz |
| 4,529,658 | A | 7/1985 | Schwartz et al. |

(Continued)

FOREIGN PATENT DOCUMENTS

| | | |
|---|---|---|
| AU | 2014292781 | 5/2018 |
| CA | 2662477 | 3/2008 |

(Continued)

OTHER PUBLICATIONS

Ban et al, Tyrosine Bioconjugation through Aqueous Ene-Type Reactions: A Click-Like Reaction for Tyrosine, Journal, J Am. Chem. Soc. (2010), 132, 1523-1525.

(Continued)

*Primary Examiner* — Christian C Boesen
(74) *Attorney, Agent, or Firm* — Bennet Jones LLP

(57) ABSTRACT

The invention relates to a bicyclic peptide complex comprising a peptide construct, said construct comprising (i) a polypeptide with free terminus (N or C); (ii) optionally, a nucleic acid encoding the polypeptide; (iii) a twofold-symmetric linker (TSL) compound attached to said polypeptide where the linker is attached to the terminus of polypeptide via a covalent bond and to at least two discrete side chains of the peptide. The invention also relates to libraries, and to methods for making complexes and to methods of screening using the same.

16 Claims, 29 Drawing Sheets

Specification includes a Sequence Listing.

(56) References Cited

U.S. PATENT DOCUMENTS

| | | | |
|---|---|---|---|
| 5,254,471 A | 10/1993 | Mori et al. | |
| 5,330,622 A | 7/1994 | Honnorat et al. | |
| 5,370,919 A | 12/1994 | Fieuws et al. | |
| 5,494,698 A | 2/1996 | White et al. | |
| 5,514,548 A | 5/1996 | Krebber et al. | |
| 5,674,961 A | 10/1997 | Fitzgerald | |
| 5,733,757 A | 3/1998 | Barbas, III et al. | |
| 5,776,711 A | 7/1998 | Vyas et al. | |
| 6,017,732 A | 1/2000 | Jespers et al. | |
| 6,043,079 A | 3/2000 | Leighton | |
| 6,472,146 B1 | 10/2002 | Larocca et al. | |
| 6,548,263 B1 | 4/2003 | Kapur et al. | |
| 6,642,014 B1 | 11/2003 | Pedersen et al. | |
| 6,653,124 B1 | 11/2003 | Freeman | |
| 7,005,294 B2 | 2/2006 | Lehmann | |
| 7,141,366 B1 | 11/2006 | Sandman et al. | |
| 7,754,680 B2 | 7/2010 | Cunningham et al. | |
| 7,998,748 B2 | 8/2011 | Harttig | |
| 8,062,890 B2 | 11/2011 | Kiessling et al. | |
| 9,518,081 B2 | 12/2016 | Winter et al. | |
| 9,594,051 B2 | 3/2017 | Whitesides et al. | |
| 9,624,523 B2 | 4/2017 | Derda et al. | |
| 9,829,488 B2 | 11/2017 | Derda et al. | |
| 9,958,437 B2 | 5/2018 | Derda et al. | |
| 10,724,034 B2 | 7/2020 | Derda et al. | |
| 10,900,061 B2 | 1/2021 | Derda et al. | |
| 2001/0054580 A1 | 12/2001 | Watkins et al. | |
| 2005/0019747 A1 | 1/2005 | Anderson et al. | |
| 2009/0137424 A1 | 5/2009 | Tsao et al. | |
| 2009/0281250 A1 | 11/2009 | Desimone et al. | |
| 2009/0298191 A1 | 12/2009 | Whitesides et al. | |
| 2010/0055733 A1 | 3/2010 | Lutolf et al. | |
| 2010/0168380 A1 | 7/2010 | Suga et al. | |
| 2010/0273259 A1 | 10/2010 | Saha et al. | |
| 2010/0317547 A1* | 12/2010 | Gregory | C40B 50/06 435/235.1 |
| 2011/0105360 A1 | 5/2011 | Derda et al. | |
| 2011/0152125 A1 | 6/2011 | Dutta et al. | |
| 2012/0135518 A1 | 5/2012 | Kiessling et al. | |
| 2012/0181184 A1 | 7/2012 | Whitesides et al. | |
| 2012/0198684 A1 | 8/2012 | Carrilho et al. | |
| 2013/0050083 A1 | 2/2013 | Chen et al. | |
| 2013/0196867 A1 | 8/2013 | Strahl et al. | |
| 2013/0252847 A1 | 9/2013 | Mckenna et al. | |
| 2014/0187757 A1 | 7/2014 | Winter et al. | |
| 2014/0349329 A1 | 11/2014 | Whitesides et al. | |
| 2015/0024958 A1 | 1/2015 | Derda et al. | |
| 2015/0316561 A1 | 11/2015 | Zhang et al. | |
| 2016/0115202 A1 | 4/2016 | Pei et al. | |
| 2016/0193582 A1 | 7/2016 | Derda et al. | |
| 2017/0253904 A1 | 9/2017 | Derda et al. | |
| 2017/0298342 A1 | 10/2017 | Derda et al. | |
| 2017/0355982 A1 | 12/2017 | Derda et al. | |
| 2018/0284106 A1 | 10/2018 | Derda et al. | |
| 2019/0352636 A1 | 11/2019 | Derda et al. | |
| 2021/0023523 A1 | 1/2021 | Derda et al. | |
| 2021/0340525 A1 | 11/2021 | Derda et al. | |
| 2022/0002341 A1 | 1/2022 | Derda et al. | |

FOREIGN PATENT DOCUMENTS

| | | |
|---|---|---|
| CA | 2861137 | 8/2013 |
| CA | 2918289 | 1/2015 |
| CA | 2935587 | 8/2015 |
| CA | 2965380 | 4/2016 |
| CN | 103382579 A | 11/2013 |
| EP | 0279077 | 3/1992 |
| EP | 1266963 | 12/2002 |
| EP | 2265959 | 3/2014 |
| EP | 2917174 | 9/2018 |
| GB | 2428293 | 1/2007 |
| JP | H09-500016 | 1/1997 |
| JP | 2001513995 A | 9/2001 |
| JP | 2003531632 A | 10/2003 |
| JP | 2004248666 A | 9/2004 |
| JP | 2009-512443 | 3/2009 |
| JP | 2005-536234 | 3/2011 |
| JP | 2015-508638 | 3/2015 |
| JP | 2015529826 A | 10/2015 |
| JP | 2016539190 A | 12/2016 |
| JP | 2017522188 | 8/2017 |
| JP | 2017535260 A | 11/2017 |
| JP | 2017536846 A | 12/2017 |
| JP | 2018068318 | 5/2018 |
| JP | 2009-511053 | 10/2019 |
| JP | 7073250 B2 | 5/2022 |
| WO | 1985001354 | 3/1985 |
| WO | 1998021593 | 5/1998 |
| WO | 99/10485 | 3/1999 |
| WO | 1999058655 | 11/1999 |
| WO | 2001005950 | 1/2001 |
| WO | 01/23619 | 4/2001 |
| WO | 2002094846 | 11/2002 |
| WO | 2004077062 | 9/2004 |
| WO | 2007008609 | 1/2007 |
| WO | 2007010525 | 1/2007 |
| WO | 2009098450 | 8/2009 |
| WO | 2009108229 | 9/2009 |
| WO | 2009120963 | 10/2009 |
| WO | 2009126980 | 10/2009 |
| WO | 2010105363 | 9/2010 |
| WO | 2010107405 | 9/2010 |
| WO | 2011018227 | 2/2011 |
| WO | 2011103668 | 9/2011 |
| WO | 2012009682 | 1/2012 |
| WO | 2012009692 | 1/2012 |
| WO | 2012056110 | 5/2012 |
| WO | 2012072987 | 6/2012 |
| WO | 2012074130 | 6/2012 |
| WO | 2012150475 | 11/2012 |
| WO | 2012162345 | 11/2012 |
| WO | 2013050083 | 4/2013 |
| WO | 2013050615 | 4/2013 |
| WO | 2013113127 | 8/2013 |
| WO | 2013184930 A2 | 12/2013 |
| WO | 2014035693 A2 | 3/2014 |
| WO | 2014052650 | 4/2014 |
| WO | 2015006874 | 1/2015 |
| WO | 2015030014 A1 | 3/2015 |
| WO | 2016057683 | 4/2016 |
| WO | 2016061695 | 4/2016 |
| WO | 2016/083793 | 6/2016 |
| WO | 2016126852 | 8/2016 |
| WO | 2018089648 A2 | 5/2018 |
| WO | 2018098226 A1 | 5/2018 |
| WO | 2018106112 A1 | 6/2018 |
| WO | 2018115204 A1 | 6/2018 |
| WO | 2018141058 | 8/2018 |
| WO | 2019084664 | 5/2019 |
| WO | 2019161495 | 8/2019 |
| WO | 2020019072 | 1/2020 |
| WO | 2020107118 | 6/2020 |

OTHER PUBLICATIONS

Bashiruddin et al, Synthesis of fused tricyclic peptides using a reprogrammed translation system and chemical modification, Journal, Bioorganic Chemistry (2015) 61 45-50.

Bellotto et al, Phage Selection of Photoswitchable Peptide Ligands, Journal, J. Am. Chem. Soc. (2014), 136, 5880-5883.

Bloom et al, Decarboxylative alkylation for site-selective bioconjugation of native proteins via oxidation potentials, Journal, Nat Chem (2018), 10 (2), 205-211.

Chelius et al, Capture of Peptides with N-terminal Serine and threonine: A Sequence-specific Chemical Method for Peptide Mixture Simplification, Journal, Bioconjug Chem, (2003), vol. 14, No. 1, pp. 205-211.

Chen et al, Embryonic Morphogen Nodal Is Associated with Progression and Poor Prognosis of Hepatocellular Carcinoma, Journal, Plos One (2014), 9 Proc. Natl. Acad. Sci. U.S.A., 2002, 99 (26), 16899-16903.

(56) References Cited

OTHER PUBLICATIONS

Chen et al, Peptide Ligands Stabilized by Small Molecules, Journal, Angew. Chem. Int. Ed. (2014), 53, 1602-1606.
Deber et al, Val-→ Ala mutations selectively alter helix-helix packing in the transmembrane segment of phage M13 coat protein, Journal, Proc. Natl. Acad Sci. USA (1993) 90, 11648-11652.
Degruyter et al, Residue-Specific Peptide Modification: A Chemist's Guide, Journal, Biochemistry (2017), 56, 3863-3873.
Derda et al, "High-throughput Discovery of Synthetic Surfaces that Support Proliferation of Pluripotent Cells", Journal, J Am. Chem. Soc. (2010), 132, 1289-1295.
Diderich, et al, Phage Selection of Chemically Stabilized α-Helical Peptide Ligands, Journal, ACS Chem. Biol. (2016), 11, 1422-1427.
Dirksen et al, Nucleophilic catalysis of oxime ligation, Journal, Angew. Chem. Int. Ed (2006) 45, 7581-7584.
Dutta et al, Selective tethering of ligands and proteins to a microfluidically patterned electroactive fluid lipid bilayer array, Journal, Langmuir (2010) 26, 9835-9841.
Eldridge et al, Hydrazide reactive peptide tags for site-specific protein labeling, Journal, Bioconjugate Chem. (2011), 22: 2143-2153.
Freedman et al "Applications of flow cytometry in transfusion medicine", Journal, Transfusion Medicine Review, (1995) vol. 9, No. 2, 87-109.
Garratty et al, Applications of flow cytometry to transfusion science, Journal, Transfusion, vol. 35, No. 2, (1995) 157-178.
Geoghegan et al, Site-directed conjugation of nonpeptide groups to peptides and proteins via periodate oxidation of a 2-amino alcohol. Application to modification at N-terminal serine, Journal, Bioconjugate Chemistry (1992) 3:136-46.
Glucksman et al, Three-dimensional structure of a cloning vector: X-ray diffraction studies of filamentous bacteriophage M13 at 7 A resolution, Journal, J Mal. Biol (1992) 226, 455-470.
Goransson et al, Disulfide Mapping of the Cyclotide Kalata B1, Journal, JBC (2003) 278:48 48188-48196.
Grant et al, Structure of the filamentous bacteriophage fl. Location of the A, C, and D minor coat proteins, Journal, J Biol Chem (1981) 256, 539-546.
Guang-Zu et al, Decarboxylative 1,4-Addition of α-Oxocarboxylic Acids with Michael Acceptors Enabled by Photoredox Catalysis, Journal, Org Lett, (2015), 17:19 4830-4833.
Hacker et al, Highly Constrained Bicyclic Scaffolds for the Discovery of Protease-Stable Peptides via mRNA Display, Journal, ACS Chem Biol (2017), 12(3), 795-804.
Heinis et al, Phage-encoded combinatorial chemical libraries based on bicyclic peptides, Journal, Nat. Chem. Biol. (2009), 5, 502-507.
Jafari et al, Allene Functionalized Azobenzene Linker Enables Rapid and Light-Responsive Peptide Macrocyclization, Journal, Bioconj. Chem. (2016), 27, 509-514.
Kale et al, Cyclization of peptides with two chemical bridges affords large scaffold diversities. Journal, Nature Chemistry (2018), 10, 715-723.
Kalhor-Monfared et al, Rapid biocompatible macrocyclization of peptides with decafluoro-diphenylsulfone, Journal, Chem. Sci. (2016), 7, 3785-3790.
Laemmli, Cleavage of Structural Proteins during the Assembly of the Head of Bacteriophage T4, Journal, Nature (1970) 227, 680-685.
Laping et al, Inhibition of transforming growth factor (TGF)-beta 1-induced extracellular matrix with a novel inhibitor of the TGF-beta type I receptor kinase activity: SB-431542, Journal, Mol. Pharmacol. (2002), 62, 58-64.
Li et al, Chemical modification of M13 bacteriophage and its application in cancer cell imaging, Journal, Bioconjugate Chem (2010) 21, 1369-1377.
Liu et al, Precisely Regulated and Efficient Locking of Linear Peptides into Stable Multicyclic Topologies through a One-Pot Reaction. Journal, Angew. Chem. Int. Ed. (2017), 56, 4458-4463.
Lonardo et al, Nodal/Activin Signaling Drives Self-Renewal and Tumorigenicity of Pancreatic Cancer Stem Cells and Provides a Target for Combined Drug Therapy, Journal, Cell Stem Cell (2011), 9, 433-446.
Love et al, Enabling Glycosyltransferase Evolution: A Facile Substrate-Attachment Strategy for Phage-Display Enzyme Evolution, Journal, (2006) ChemBioChem 7:753-6.
Ng and Derda, Phage-displayed macrocyclic glycopeptide libraries, Journal Org. Biomol. Chem. (2016), 14, 5539-5545.
Ng et al, "Bacteriophages and Viruses as a Support for Organic Synthesis and Combinatorial Chemistry-", Journal, ACS Chem. Biol. (2012), 7(1) 123-138.
Ng et al, "Quantitative Synthesis of Genetically, Encoded Glycopeptide Libraries Displayed on M13 Phage", Journal, ACS Chemical Biology, (2012), 7(9) 1482-1487.
Sako et al, Ribosomal Synthesis of Bicyclic Peptides via Two Orthogonal Inter-Side-Chain Reactions, Journal, J. Am. Chem. Soc. (2008), 130 (23), 7232-7234.
Strizzi, et al, Effects of a novel Nodal-targeting monoclonal antibody in melanoma, Journal, Oncotarget (2015), 6, 34071-34086.
Teufel et al, Stable and Long-Lasting, Novel Bicyclic Peptide Plasma Kallikrein Inhibitors for the Treatment of Diabetic Macular Edema, Journal, J. Med. Chem. (2018), 61 (7), 2823-2836.
Tilley and Francis, Tyrosine-Selective Protein Alkylation Using π-Allylpalladium Complexes, Journal, J Am Chem Soc (2006), 128, 1080-1081.
Wang, Decarboxylative 1,4-Addition of alpha-Oxocarboxylic Acids with Michael Acceptors Enabled by Photoredox Catalysis, Journal, Org. Lett. (2015), 17 (19), 4830-3.
Woiwode et al., Synthetic Compound Libraries Displayed on the Surface of Encoded Bacteriophage, Journal, Chemistry and Biology, (2003), 10(9), 847-858.
Franzini et al, DNA-Encoded Chemical Libraries: Advancing beyond Conventional Small-Molecule Libraries Accounts of Chemical Research, Journal, ACC Chem Res, (2014), 47, 1247-1255.
Assem et al, Acetone-Linked Peptides: A Convergent Approach for Peptide Macrocyclization and Labeling, Journal, Angewandte Chemie International Edition, (2015), 127(30) 8789-8792.
Mccarthy et al, Phage Display of Dynamic Covalent Binding Motifs Enables Facile Development of Targeted Antibiotics, Journal, Journal of the American Chemical Society (2018), 140, 6137-6145.
Uematsu et al, Combinatorially Screened Peptide as Targeted Covalent Binder: Alteration of Bait-Conjugated Peptide to Reactive Modifier, Journal, Bioconjugate Chemistry (2018), 29, 1866-1871.
Gupta et al, Reactivity, Selectivity, and Stability in Sulfenic Acid Detection: A Comparative Study of Nucleophilic and Electrophilic Probes, Journal, Bioconjugate Chemistry (2016), 27, 1411-1418.
Rader et al, A Humanized Aldolase Antibody for Selective Chemotherapy and Adaptor Immunotherapy, Journal, Journal of Molecular Biology (2003), 332(4), 889-899.
Barbas et al, Assembly of combinatorial antibody libraries on phage surfaces: the gene III site, Journal, Proceedings of the National Academy of Sciences (1991), 88, 7978-7982.
Derda et al. Paper-supported 3D cell culture for tissue based bioassays, Journal, PNAS (2009) U.S.A. 106(44) 18457-18462.
Derda et al., Multizone Paper Platform for 3D Cell Cultures, Journal, PLoS One, (2011) 6(5) e18940.
Funes-Huacca et al, Portable self-contained culture for phage and bacteria made of paper and tape, Journal, Lab Chip (2012) 12, 4269-4278.
Krebber et al., Selectively-infective phage (SIP): a mechanistic dissection of a novel in vivo selection for protein-ligand interactions, Journal, J. Mol. Biol, (1997), 268, 607-618.
Agarwal and Banerjee, Screening of Xanthine Oxidase Producing Microorganisms Using Nitroblue Tetrazolium Based Colorimetric Assay Method, Journal, The Open Biotechnology Journal, (3) 46-49, Published online: May 21, 2009.
Einhauer and Jungbaeur, The FLAG™ peptide, a versatile fusion tag for the purification of recombinant proteins, Journal, J. Biochem. Biophys Methods, (2001) 49, 455-65.
Cebe and Geiser, Size of the ligand complex between the N-terminal domain of the gene III coat protein and the non-infectious phage

(56) References Cited

OTHER PUBLICATIONS strongly influences the usefulness of in vitro selective infective phage technology, Journal, Biochem J, (2000), 352, 841-849.
Deiss et al. Flow-through synthesis on Teflon-patterned paper to produce peptide arrays for cell-based assays, Journal, Angewandte Chemie International Edition, (2014) 53, 6374-6377.
Kozak et al. Micro-volume wall-less immunoassays using patterned planar plates, Journal, Lab Chip, (2013) 13, 1342-1350.
Winkler, Chemistry of SPOT synthesis for the preparation of peptide macroarrays on cellulose membranes, Journal, Mini-reviews in Organic Chemistry, (2011) 8, 114-120.
Winkler, et al, SPOT Synthesis as a Tool to Study Protein-Protein Interactions, Protein Microarray for Disease Analysis (2011) 723, 105-127, DOI: 10.1007/978-1-61779-043-0_8.
Carrilho et al, Understanding wax printing: A simple micropattem-ing process for paper-based microfluidics, Journal, Analytical Chemistry, (2009) 81, 7091-7095.
Hilpert et al, Peptide arrays on cellulose support: SPOT synthesis, a time and cost efficient method for synthesis of large numbers of peptides in a parallel and addressable fashion. Nature Protocols, Journal, (2007) 2(6), 1333-1349.
Hilpert et al, Cellulose-bound peptide arrays: Preparation and applications. Biotechnology and Genetic Engineering Reviews, Journal, (2007) 24, 31-106.
Heine et al, Synthesis and screening of peptoid arrays on cellulose membranes. Tetrahedron, Journal, (2003) 59, 9919-9930.
Reineke et al, Applications of peptide arrays prepared by the SPOT-technology. Current Opinion in Biotechnology, Journal, (2001), 12, 59-64.
Frank, Spot-synthesis: An easy technique for the positionally addressable, parallel chemical synthesis on a membrane support, Journal, Tetrahedron, (1992) 48(42), 9217-9232.
Deiss et al, Platform for High-Throughout testing of the Effect of Soluble Compounds on 3D Cell Cultures, Journal, Analytical Chemistry, (2013), 85:17, 8085-8094.
Klim et al., A defined glycosaminoglycan-binding substratum for human pluripotent stem cells, Journal, Nature Methods (2010), 7, 989-994.
Melkoumian, et al, Synthetic peptide-acrylate surfaces for long-term self-renewal and cardiomyocyte differentiation of human embryonic stem cells, Journal, Nature Biotechnology, (2010) 28, 606-610.
Li et al, Spatial control of cell fate using synthetic surfaces to potentiate TGF-β signaling, Journal, PNAS (2011), 108 (29), 11745-1175.
Giam et al, Scanning probe-enabled nanocombinatorics define the relationship between fibronectin feature size and stem cell fate, Journal, PNAS, (2012) 109(12), 4377-4382.
Yetisen et al, Paper-based microfluidic point-of-care diagnostic devices, Journal, Lab Chip, (2013), 13, 2210-2251.
Hossain et al, Reagentless Bidirectional Lateral Flow Bioactive Paper Sensors for Detection of Pesticides in Beverage and Food Samples, Journal, Anal Chem, (2009), 81, 9055-9064.
Tian et al, Patterning of controllable surface wettability for printing techniques, Journal, Chem Soc Rev, (2013), 42, 5184-5209.
Ueda et al, DropletMicroarray: facile formation of arrays of microdroplets and hydrogel micropads for cell screening applications, Journal, Lab Chip, (2012) 12, 5218-5224, DOI: 10.1039/c21c40921f.
Wang et al, MALDI MS Sample Preparation by Using Paraffin Wax Film: Systematic Study and Application for Peptide Analysis, Journal, Analytical Chemistry, (2008) 80(2), 491-500.
Stronghold Wax: Wax Solubility, Website (2014), obtained online from https://strongholdwax.com/wax-solubility/ on Apr. 7, 2021.
Ng et al, Genetically encoded fragment-based discovery of glycopeptide ligands for carbohydrate-binding proteins, Journal, Journal of the American Chemical Society, (2015), 137, 5248-5251.
Schlippe et al, In Vitro Selection of Highly Modified Cyclic Peptides That Act as Tight Binding Inhibitors, Journal, JACS, (2012), 134, 10469-10477.
Scott and Smith, Searching for Peptide Ligands with an Epitope Library, Journal, Science (1990) 249, 386-390.
Brenner and Lerner, Encoded combinatorial chemistry, Journal, PNAS (1992), 89(12), 5381-5383.
Santoso et al, A simple and efficient maleimide-based approach for peptide extension with a cysteine-containing peptide phage library, Journal, Bioorganic & Medicinal Chemistry Letters, (2013), 23, 5680-5683.
Kawakami et al, In Vitro Selection of Multiple Libraries Created by Genetic Code Reprogramming To Discover Macrocyclic Peptides That Antagonize VEGFR2 Activity in Living Cells, Journal, ACS Chem Biol, (2013), 8, 6, 1205-1214.
Josephson et al, Ribosomal Synthesis of Unnatural Peptides, Journal, J Am Chem Soc, (2005), 127, 33, 11727- 11735.
Jafari et al, Discovery of Light-Responsive Ligands through Screening of a Light-Responsive Genetically Encoded library, Journal, ACS Chem Biol (2014), 9, 443-450.
Matochko et al, Deep sequencing analysis of phage libraries using Illumina platform, Journal, Methods (2012), 58 (1), 47-55.
Guillon et al, Design, Synthesis, and in vitro Antifungal Activity of 1-[(4-Substituted-benzyl)methylamino]-2-(2,4-difluorophenyl)-3-(1H-1,2,4-triazol-1-yl)propan-2-ols, Journal, ChemMedChem, (2011), 6(5), 816-825.
Kitov et al, Rapid, Hydrolytically Stable Modification of Aldehyde-Terminated Proteins and Phage Libraries, Journal, J Am Chem Soc, (2014), 136, 8149-8152.
Kim et al, Synthesis of all-hydrocarbon stapled α-helical peptides by ring-closing olefin metathesis, Journal, Nature protocols, (2011), 6, 761-771.
Matochko et al, Prospective identification of parasitic sequences in phage display screens, Journal, Nucleic Acids Res (2014), 42(3) 1784-1798.
Wang et al, Influence of Solution and Gas Phase Processes on Protein-Carbohydrate Binding Affinities Determined by Nanoelectrospray Fourier Transform lon Cyclotron Resonance Mass Spectrometry, Journal, Anal Chem, (2003), 75, 4945-4955.
Kitova et al, Reliable Determinations of Protein-Ligand Interactions by Direct ESI-MS Measurements. Are We There Yet?, Journal, J Am Soc Mass Spectrom, (2012), 23, 431-441.
El-Hawiet et al, Quantifying Carbohydrate-Protein Interactions by Electrospray Ionization Mass Spectrometry Analysis, Journal, Biochemistry, (2012), 51, 4244-4253.
Sun et al, Method for Distinguishing Specific from Nonspecific Protein-Ligand Complexes in Nanoelectrospray Ionization Mass Spectrometry, Journal, Anal Chem, (2006), 78, 3010-3018.
Chilkoti et al, Site-directed mutagenesis studies of the high-affinity streptavidin-biotin complex: contributions of tryptophan residues 79, 108, and 120, Journal, Proc Nat. Acad Sci USA, (1995), 92, 1754-1758.
Green, Avidin and streptavidin, Journal, Methods Enzymol. (1990), 184, 51-67.
Tjhung et al., "Silent Encoding of Chemical Post-Translational Modifications in Phage-Displayed Libraries", Journal, Journal of The American Chemical Society, vol. 138, No. 1, Dec. 28, 2015, pp. 32-35.
Laskowski et al, The structural basis of allosteric regulation in proteins, Journal, FEBS letters, (2009) 583, 1692-1698.
Marvin et al, Molecular structure of fd (f1, M13) filamentous bacteriophage refined with respect to X-ray fibre diffraction and solid-state NMR data supports specific models of phage assembly at the bacterial membrane, Journal, Journal of molecular biology, (2006) 355, 294-309.
Ellington and Szostak, In vitro selection of RNA molecules that bind specific ligands, Journal, Nature, (1990) 346, 818-822.
Tuerk et al, Systematic evolution of ligands by exponential enrichment: RNA ligands to bacteriophage T4 DNA polymerase, Journal, Science, (1990) 249, 505-510.
Bonaventura et al "An antimicrobial bicyclic peptide from chemical space against multidrug resistant Gram-negative bacteria." 2018 Chem Commun. 54, pp. 5130-5133.

(56) References Cited

OTHER PUBLICATIONS

Dillon T Flood et al "Leveraging the Knorr Pyrazole Synthesis for the Facile Generation of Thioester Surrogates for use in Native Chemical Litigation" Angewandte Chemie vol. 130 No. 36 Aug. 10, 2018 pp. 11808-11813.
Heinis Christian et al, Encoded Libraries of Chemically Modified Peptides, Current Opinion in Chemical Bio, vol. 27 Jun. 1, 2015 pp. 89-98.
Marzinzik et al, "Solid Support Synthesis of Highly Functionalized Pyrazoles and Isoxazoles; Scaffolds for Molecular Diversity"Tetrahedron Letters, Elsevier, Amsterdam, NL, vol. 37 No. 7 Feb. 12, 1996 pp. 1003-1006.
Mohammad R Jafari et al; "Light-responsive bicyclic peptides", Organic & Biomolecular Chem, vol. 16 No. 41, Aug. 1, 2018, pp. 7588-7594.
Simon Ng et al, Phase-Displayed Macrocyclic glycopeptide libraries Organic and Biomolecular Chem. vol. 14 No. 24 Feb. 4, 2016 pp. 5539-5545.
Wong Jeffery, Y.-K et al: "Genetically-encoded discovery of proteolytically stable bicyclic inhibitors for morphogen NODAL" Chem Sci. vol. 12, No. 28 Jun. 17, 2021, p. 9694-9703.
Bonaventura et al, Supporting Information: An Antimicrobial Bicyclic Peptide from Chemical Space Against Multidrug Resistant Gram-Negative Bacteria (2018) Electronic Supplementary Material (ESI) for Chemical Communications. pp. 1-79.
Trindade et al., Irreversible Conjugation of Aldehydes in Water To Form Stable 1,2,4-Oxadiazinan-5-ones Organic Letters, 18(17): 4210-4213 (2016).
Volatron et al., Wittig versus Corey-Chaykovsky Reaction. Theoretical study of the reactivity of phosphonium methylide and sulfonium methylide with formaldehyde J of the American chem soc 109(1): 1-14 (1987).
Mestres et al., A green look at the aldol reaction Green Chem, 6: 583-603 (2004).
Sprung, M., A Summary of the Reactions of Aldehydes with Amines Chemical Reviews, 26(3): 297-338 (1940).
Korean International Property Office, Office Action, Jan. 10, 2025.

* cited by examiner

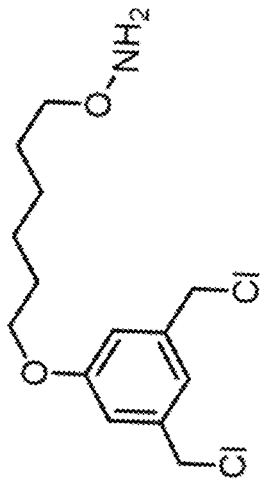
3
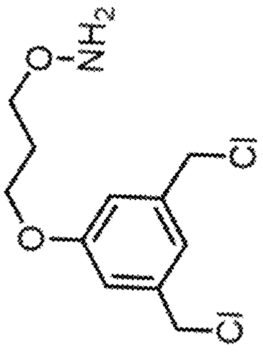
2
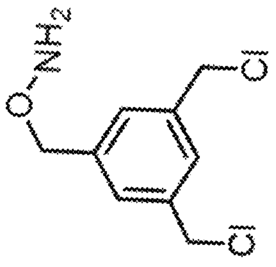
1
Sequence1: SHCVWWDC
Sequence2: SLCFDNGC
Sequence3: SFCDWYGC
Sequence4: SWCDYRC
Sequence5: SHDCYLEC
Sequence6: SWDYRECYLEC
Figure 4A.

Reagents and conditions: a) BocNHOH, DBU, DCM; b) LiCL, DMF, 10h; c) TFA, DCM

7

8

9a when n =0
9b when n = 4

10a when n =0
10b when n = 4

11a when n =0
11b when n = 4

2 when n = 0
3 when n = 4

Reagents and conditions: a) $LiAlH_4$, THF, 0°C to rt, 1 h; b) 1, n-dbromoalkane, $K_2CO_3$, $CH_3CN$, reflux, 72 h; c) BocNHOH, DBU, DCM, 5 h; d) MsCl, $Et_3N$, 0°C to rt, 5 min; e) LiCL, DMF, 10h; f) TFA, DCM a

| SS | Sequence | Linker | Product |
|---|---|---|---|
| 1a | H-SWDYRECYLEC-NH$_2$ | TSL-6 | 1d |
| 1a | H-SWDYRECYLEC-NH$_2$ | TSL-1 | 1f |
| 2a | H-SHCVWWDC-NH$_2$ | TSL-6 | 2d |
| 2a | H-SHCVWWDC-NH$_2$ | TSL-3 | 2e |
| 2a | H-SHCVWWDC-NH$_2$ | TSL-1 | 2f |
| 3a | H-SHDCYLEC-NH$_2$ | TSL-6 | 3d |
| 3a | H-SHDCYLEC-NH$_2$ | TSL-1 | 3f |
| 3a | H-SHDCYLEC-NH$_2$ | TSL-3 | 3e |
| 4a | H-SWCDYRC-NH$_2$ | TSL-6 | 4d |
| 5a | H-SFCDWYGC-NH$_2$ | TSL-6 | 5d |
| 6a | H-SLCFDNGC-NH$_2$ | TSL-6 | 6d |
| 7a | H-SHCDYYC-NH$_2$ | TSL-1 | 7f |
| 8a | H-SYCKADC-NH$_2$ | TSL-1 | 8f |
| 9a | H-SWCFYRC-NH$_2$ | TSL-1 | 9f |
| 10a | H-SDCGFVSC-NH$_2$ | TSL-3 | 10e |
| 11a | H-SYCKPFC-NH$_2$ | TSL-3 | 11e |
| 11a | H-SYCKPFC-NH$_2$ | TSL-1 | 11f |
| 12a | H-STCQGECGGG-NH$_2$ | TSL-3 | 12e |
| 13a | H-SICRFFCGGG-NH$_2$ | TSL-3 | 13e |
| 13a | H-SICRFFCGGG-NH$_2$ | TSL-1 | 13f |
| 14a | H-SNTWNPWCPWDAPL-cam | TSL-1 | 14f |
| 15a | H-SSWPARCLHQDLC-NH$_2$ | TSL-1 | 15f |
| 12a | H-STCQGECGGG-NH$_2$ | PFS | 12i |
| 13a | H-SICRFFCGGG-NH$_2$ | PFS | 13i |
| 16a | Ac-CNTWNPWCPWDAPLC-NH$_2$ | TBMB | 16j |
| 17a | Ac-CSWPARCLHQDLC-NH$_2$ | TBMB | 17j |

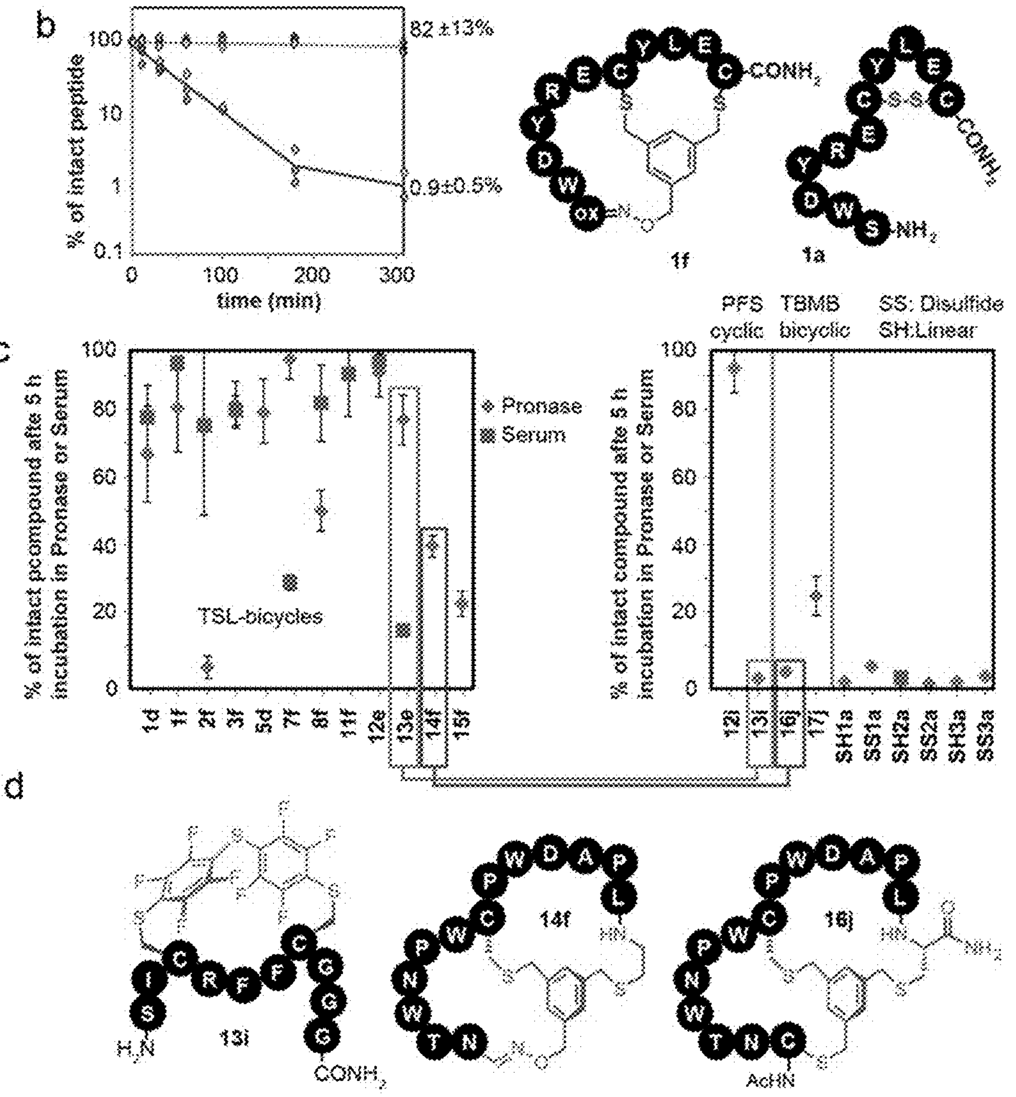

Figure 11

A
SB: SB431542, Nodal singaling inhibitor
Inhibitor
Nodal
pSmad2
Smad 2/3
Peptides: 10 μM
B
Control
Peptides(10μM)
C
Inhibitor
Nodal
pSMAD
SMAD
D
Inhibitors
Nodal
pSMAD
SMAD
Control
#7(μM)

GENETICALLY-ENCODED BICYCLIC PEPTIDE LIBRARIES

FIELD

The present application pertains to the field of receptor-ligand interactions and molecular recognition. More particularly, the present application relates to bicyclic peptide libraries, methods for producing libraries of bicyclic peptides, and the use of such libraries in various assays.

SEQUENCE LISTING

A Sequence Listing is provided herewith as an ASCII .txt file "Sequence Listing 17_261390_v2.txt" created on Apr. 8, 2025 and having a size of 20.4 KB. The contents of the Sequence Listing .txt file are incorporated by reference herein in their entirety.

BACKGROUND

The generation of libraries of small molecules and selection of those molecules that bind uniquely to a target of interest is important for drug discovery. The production of genetically-encoded libraries, in which each library member is linked to an information template, such as DNA or RNA, makes it possible to process large chemical libraries without separating individual library members into individual solutions and reaction vessels. One can select target molecules from mixtures of genetically-encoded molecules and identify or amplify the selected molecule of interest using its information template.

Peptides that contain intramolecular covalent bonds and exhibit bicyclic topology are known to be more stable to proteolysis and other forms of degradation than monocyclic or linear peptides. They are also known to exhibit stronger binding interactions with protein targets; it is hypothesized that the increase in interaction is due to a reduced conformational penalty of the constrained bicyclic system compared to linear or cyclic system.

Phage display is one example of a well-known technique used in the analysis, display and production of a genetically-encoded library of peptides and proteins (Scott et al, 1990). Phage display is a process during which the phage is made to expose or "display" different peptides or proteins such as human antibodies on its surface. Through genetic engineering, peptides or proteins of interest are attached individually to a phage cell surface protein molecule (usually Gene III protein or g3p). In such a phage population (phage library), each phage carries a gene for a different fusion peptide or protein of g3p and exposes it on its surface. Through a variety of selection procedures, phages that "display" binders to specific target molecules of interest can be identified and isolated. These binders can include interaction partners of a protein to determine new functions or mechanisms of function of that protein, peptides that recognize and bind to antigens (for use in diagnosis and therapeutic targeting, for example), and proteins involved in protein-DNA interactions (for example, novel transcription factors).

Phage display can be very useful in discovery and development of pharmaceutical and/or diagnostic polypeptides. In phage display, the entire phage binds and can be eluted from an immobilized target molecule. Since the phage remains infective it can inject its DNA into bacterial cells and is amplified. Phage display methods are usually restricted to the production of libraries, which can be encoded by direct DNA-RNA-protein information transfer. These methods are typically limited to linear sequences of peptides, made of only 20 natural amino acids or cyclic peptides cross-linked through a disulfide bond.

RNA and ribosome display are other techniques known in the art that permit display of naturally-made peptides on information templates. The amplification of libraries of peptides attached to RNA requires an in vitro translation system to generate or reamplify the library. Suga et al (US20100168380 A1) teach production of cyclic peptides comprising N-methyl amino acids and other special (non-standard) amino acids by encoding unnatural amino acids in the RNA sequence. There are no examples of direct encoding of the bicyclic peptides in RNA and production of bicyclic libraries by translation alone.

It is known to produce a library of bicyclic peptides or display of bicyclic peptides on phage, DNA or RNA by the modification of encoded display of molecules derived from peptides via chemical post-translational modifications (cPPTM). Typically, these methods use organic synthesis on the peptides to make peptide derivatives. It is known that an entire peptide library can be modified by uniform chemical modification. Selection from the modified library and sequencing of the DNA yields peptide sequences from which the modified peptide derivatives can be made. Several methods exist which involve conversion of libraries of peptides, libraries of phage-displayed polypeptides and libraries of RNA-displayed polypeptides to libraries of peptide derivatives.

Suga et al. describe methodology for the synthesis of bicyclic peptides displayed on RNA by using a cysteine (Cys) and three different non-proteinogenic amino acids, Cab, Aha, and Pgl simultaneously incorporated into a peptide chain. The first cyclization occurred between the chloroacetyl group of Cab and the sulfhydryl group in Cys in situ of translation, and the second cyclization on the side chains of Aha-Pgl was performed via Cu(I)-catalyzed azide-alkyne cycloaddition. (J. Am. Chem. Soc., 2008, 130 (23), pp 7232-7234). Hartman and coworkers used a different approach that combines two Cys, and non-proteinogenic amino acids, azidohomoalanine (AzHA) and p-ethynyl phenylalanine (F-yne) (ACS Chem. Biol. 2017, 12, 795-804). The first cyclization occurred by cross-linking the cysteine with dibromo-m-xylene and the second cyclization on the side chains of AzHA-F-yne was performed via Cu(I)-catalyzed azide-alkyne cycloaddition. Expressing unnatural amino acids (UAA) such as Aha, Pgl, F-yne requires specialized unnatural translation system; expression of multiple unnatural side chains is difficult in display systems such as phage display does to low efficiency of incorporation of UAA. It is thus of interest to develop methods that use peptides composed of natural amino acid residues.

In US Patent Publication WO2004/077062, a method is described for modification of plurality of unprotected peptides made of natural amino acid residues in water by symmetric linkers to produce libraries of cyclic and bicyclic peptides. This method can be extended to other threefold symmetric linkers with three thiol reactive groups but the number of such linkers with such high symmetry is limited. Prior art examples (WO2009098450A2, WO2004077062, WO2011018227A2) and peer reviewed literature ((*Nat. Chem. Biol.* 2009, 5, 502-507; *Angew. Chem. Int. Ed.* 2014, 53, 1602-1606) describe synthesis of bicycles limited to sulfur-containing side chains and a three-fold-symmetric connector compounds with three identical reactive groups such as tris-(bromomethyl) benzene (TBMB). Production of bicyclic peptides by linkers of lower symmetry (twofold) is not obvious from such prior art. The prior art examples that use two-fold symmetric linkers to modify a plurality of unprotected peptides made of natural amino acids are restricted to production of monocyclic peptides (*ACS Chem. Biol.* 2016, 11, 1422-1427*; J. Am. Chem. Soc.* 2014, 136, 5880-5883*; Bioconj. Chem.* 2016, 27, 509-514; Chem. Sci. 2016, 7, 3785-3790*; Org. Biomol. Chem.* 2016, 14, 5539-5545)

It is of interest to generate libraries that use of lower symmetry linkers, such as two-fold symmetric linkers to access a wide chemical diversity space and maximize the likelihood of finding the bicycle with desired chemical or biological properties. Applying low-symmetry modifications to unprotected peptides has been reported but all examples in the art demonstrate that linkers of low symmetry when applied to modification of unprotected peptides produce a complex mixture of bicyclic peptides. Heinis and coworkers (*Nature Chemistry* 2018, 10, 715) specifically demonstrate that the use of two-fold symmetric linker that reacts with amino acid side chain produces a complex mixture of multiple bicyclic structures. Such mixtures might not be separable by chromatography techniques or other techniques. Liu, Heinis et al demonstrate that two fold symmetric linker applied to modification of side-chains produces a complex mixture of products (*Angew. Chem. Int. Ed.* 2017, 56, 4458) and specialized amino acids with unnatural side chains must be used to avoid production of such heterogeneous mixtures. These and other examples generally highlight that it is well understood that when modifiers of two-fold or lower symmetry are used to modify three or more similar reactive groups in peptides, such reactions produce uncontrolled complex mixture of products.

Specialized methods to synthesize bicycle peptides are known by methods that mandates the use of one or more of the following factors: (i) amino acids that contain specialized reactive groups not found in natural amino acids, (ii) protecting groups for amino acids, (iii) solid support for organic synthesis, (iv) organic solvents and (v) reaction conditions that are not compatible with biomolecules such as DNA, RNA and biomolecular complexes such as phage. There do not appear to be examples of use of low-symmetry linkers for synthesis of bicyclic peptides that comprise a modification of peptides devoid of protecting groups and made of natural amino acids. Such methods are of interest because they may offer an unencumbered route to the synthesis of a large variety of genetically encoded bicyclic structures.

In US Patent Publication WO2009098450 A3, a method is described for modification of genetically-encoded peptide libraries displayed on phage with a threefold symmetric linker. The method produces libraries of bicyclic peptides with free amino terminus and it mandates the use of threefold symmetric linkers with thiol reactive groups. The difficulty of generating phage libraries with odd number of cysteines (here, three) is known in the art.

The above methods described in the prior art are believed to produce libraries of bicyclic peptides, each with a free amino terminus. This terminus is then known to be susceptible to proteolytic cleavage. Methodologies that produces polycyclic peptides without free N-terminus are known but such methods requires incorporating non-proteogenic amino acid containing an N-chloroacetyl (ClAc) group. Methods that produce genetically-encoded bicyclic libraries with blocked N-terminus from natural amino acids are not known.

This background information is provided for the purpose of making known information believed to be of possible relevance to the present invention. No admission is necessarily intended, nor should be construed, that any of the preceding information constitutes prior art against the present invention.

SUMMARY

In general terms, the invention comprises bicyclic peptides, with no N-terminal residue, made by modifying a peptide or multiple peptides (a library) with a linker. Preferably, the peptide or peptide library comprises polypeptides comprising or consisting of unprotected natural proteogenic amino acids.

In some embodiments, the invention comprises genetically-encoded bicyclic peptide libraries, with no N-terminal residue, made by modifying a genetically-encoded peptide library with a linker.

Therefore, in some embodiments, the invention may comprise a genetically-encoded peptide construct comprising:

(a) a polypeptide;
(b) a nucleic acid encoding the polypeptide and optionally an identifying tag uniquely identifying the polypeptide and; and
(c) a bicyclic structure resulting from attaching a linker having a first end reactive group (A) and a second end comprising two reactive groups (B2, B2) to the polypeptide, wherein the first end is ligated to a terminus of the polypeptide by a covalent bond, and wherein both reactive groups of the linker second end are attached to side chain residues of the polypeptide by covalent bonds.

In some embodiments, the linker has two-fold symmetry in that the two second end reactive groups are identical. In some embodiments, the polypeptide terminus is an N-terminus and the side chain residues are each cysteine, lysine or tyrosine. Alternatively, the polypeptide terminus is a C-terminus and the side chain residues are each cysteine, lysine or tyrosine. The linker first end reactive group then is a group with unique reactivity to C-terminus, such as a C-terminal-selective photoredoxdecarboxylative conjugate addition, in acidic pH (Org. Lett., 2015, 17, 4830-4833 and Nature Chemistry 2018, 10, 205-211). In some embodiments, the linker first end reactive group is an aldehyde reactive group, such as oxime, hydrazine, 2-amino benzamidoxime, phosphonium ylide, sulphur ylide, nitrogen ylides or any other carbon nucleophile and carbenoid reagents known to be reactive with aldehydes and stable in aqueous environment.

In some embodiments, the linker second end reactive groups are electrophilic groups reactive with thiol, amine or phenol. Examples of thiol-reactive groups are haloketone, haloacetamide, halobenzyl, a Michael acceptor comprising a conjugated C═C double bond including maleimides, actylates, carbonylacrylic reagents, 3-arylpropiolonitriles, allenamides fluoroarene, chlorotetrazines, Julia-Kocieński-like reagents, 2-azidoacrylates, organometallic palladium reagents, organo gold (I) reagents, conversion of thiols to dehydroalanines (Dha) followed by conjugate addition to Dha any other methods that react specifically with thiol residues in water. Examples of groups which react specifically with lysine amine residues in water such as N-hydroxysuccinimide esters, aryl esters, perfluoroaryl esters, perfluoroarenes, ketenes, ortho-phthalaldehydes strain-release amine modifying agents or other group that reacts specifically with lysine amine residues in water. Examples of groups that react with tyrosine or other aromatic side chains are allylpaladium (J. Am. Chem. Soc. 2006, 128, 1080-1081), diazodicarboxylate (J. Am. Chem. Soc. 2010, 132, 1523-1525), diazonium salts, aniline-formaldehyde hemi-aminal, rhodium carbenoids, dirhodium metallopeptide catalysts, Manganese-Catalyzed C—H Alkynylation, Waser's reagent, 1-[(triisopropylsilyl)ethynyl]-1,2-benziodoxol-3(1 H)-one (TIPS-EBX), under gold (I) catalysis, selective ruthenium-(II)-catalyzed C—H activation, palladium (II) acetate catalyzed C—H activation with aryl iodides in water, and other reagents known in the art to modify phenol of the tyrosine residue specifically (Biochemistry 2017, 56, 3863-3873).

In some embodiments, the polypeptide comprises two cysteine residues and an N-terminal serine or threonine residue, wherein the N-terminal serine or threonine is first converted to an aldehyde by selective oxidation for reaction with the linker first end reactive group and wherein the linker second end reactive groups are covalently bonded to the cysteine residues.

In some embodiments, the complex may be attached to a carrier such as a phage particle bearing the polypeptide externally and including a nucleic acid encoding the polypeptide. Alternatively, the complex may be a RNA display compound, bearing the polypeptide; and including an RNA sequence encoding the polypeptide, and linked to the polypeptide. Alternatively, the complex may be a DNA display compound, said DNA display bearing the polypeptide; and including a DNA encoding the polypeptide, linked to the polypeptide. Alternatively, the complex may be a polypeptide linked to a polymer or protein carrier along with the identifying tag such as another peptide.

In another aspect, the invention may comprise a method for making a phage display complex, said method comprising (i) providing a phage particle comprising a polypeptide having a terminus, (ii) providing a linker having a first end reactive group and a second end comprising two reactive groups, and forming an intermediate complex by ligating the linker first end reactive group with the polypeptide terminus to form a covalent bond ("ligation step"), and (iii) forming a bicyclic structure from the intermediate complex by reacting both reactive groups of the linker second end to side chain residues of the polypeptide ("bicyclization step"). The ligation step and the bicyclization step are preferably independent and sequential steps, and/or are preferably performed at different pHs.

In some embodiments, the terminus of the polypeptide is an N-terminus and is oxidized to aldehyde ("oxidation step") before the ligation step, and wherein the ligation step comprises mixing the polypeptide comprising N-terminal aldehyde with the linker in aqueous buffer of acidic pH. Preferably, the intermediate complex produced after the ligation step is purified, such as by size-exclusion purification, for example gel filtration or dialysis in aqueous buffer of acidic pH, preferably below about pH 5.

In some embodiments, the intermediate complex, which may have been purified, is reduced with a reducing agent such as TCEP ("reduction step"), prior to the bicyclization step. The reduced intermediate complex may then be exposed to an alkaline pH (>7) to induce bicyclization, where the second end reactive groups each comprise a thiol-reactive group which react with two cysteine residues in the polypeptide.

In some embodiments, the peptide is modified to introduce the first cycle and an orthogonally reactive diketone group. The diketone group can be then used to conduct the reaction that creates a second cycle (bicyclization reaction). The intermediate complex which contains the first cycle and diketone group may be purified and stored without the deterioration of the reactivity of the diketone, which may be a 1,3 diketone. The intermediate complex may then be subject to many reactions that use unique reactivity of 1,3-diketone and hydrazine in biocompatible aqueous conditions.

In some embodiments, the 1,3-diketone functionality is introduced by reaction of peptide that contains two cysteine residues with 1,5-dichloropentadione-2,5 in neutral aqueous conditions (about pH 7 to about pH 8) forming a monocyclic peptide with 1,3-diketone functionality.

In some embodiments, the second cyclic structure is formed by combining the monocyclic peptide that contains 1,3-diketone functionality with a molecule that contains hydrazine functionality and functionality with unique reactivity towards the N- or C-terminus of the peptide. Reaction between these molecules lead to formation of the connection between 1,3-ketone functionality and the terminus of the peptide to form a second cycle in the peptide. Alternatively, a hydrazine may be reacted with the 1,3 diketone to present a new functional or reactive group, which may then be linked to the N- or C-terminus of the peptide by a linear linker.

In another aspect, the invention may comprise a method for measuring the yield of a reaction after at least one chemical reaction step described herein, the method comprising the steps of exposing the complex or the polypeptide to a capture reagent which is reactive to unreacted polypeptide but not reacted polypeptide and measuring the incorporation of capture agent with an affinity reagent. The capture agent comprises a reactive group and affinity handle paired with the affinity reagent. The affinity handle-affinity reagent pair may comprises any affinity ligand pairing known to have sufficiently high specific binding to permit quantification of binding pairs. Exemplary pairs include biotin-streptavidin, FLAG peptide-antiFLAG antibody, sulphonamide-carbonic anhydrase, methotrexate-dehydrofolate reductase (DHFR). Preferably, the affinity handle or the affinity reagent is immobilized on a solid support, such as agarose beads.

In some embodiments, the capture agent reactive group is an aldehyde reactive group such as aminooxy group, or a thiol reactive group such as iodoacetamide.

In some embodiments, the measured reaction is the oxidation step, where the phage or complex is exposed to aminooxybiotin (AOB) after the oxidation step, which react with N-terminus groups oxidized to aldehyde, diluting the reactions by at least one order of magnitude, adding streptavidin beads to retain reacted complexes, and measuring the difference in number of phage retained on the streptavidin beads compared to the number of phage not retained to determine the yield of the oxidation step (the fraction of phage particles that acquired an aldehyde group).

In some embodiments, the measured reaction is the ligation step, where the phage or complex is exposed to aminooxybiotin (AOB) before and/or after the ligation step, diluting the reactions by at least one order of magnitude, adding streptavidin beads to retain phage or complexes which had unligated aldehyde groups, and measuring the difference in number of phage particles retained on the beads compared to the number of phage not retained to determine the yield of the ligation step (the fraction of phage particles that lost an aldehyde group).

In some embodiments, the measured reaction is the reduction step, where the phage or complex is exposed to biotin-iodoacetamide (BIA), before and/or after the reduction step, diluting the reactions by at least one order of magnitude, adding streptavidin beads to retain phage or complexes which reduced to expose thiol groups, and measuring the difference in the number of phage particles retained on the beads compared to the number of phage not retained to determine the yield of reduction step (the fraction of phage particles that acquired thiol groups during the reduction step).

In some embodiments, the measured reaction is the bicyclization step, where the phage or complex is exposed to biotin-iodoacetamide (BIA), before and/or after bicyclization step, diluting the reactions by at least one order of magnitude, adding streptavidin beads to retain phage or complexes with unreacted thiol groups, measuring the number of phage particles retained on the beads compared to the number of phage not retained to determine the yield of the bicyclization step (the fraction of phage particles that lost thiol groups during the bicyclization step). Alternatively, the phage or complex may be exposed to biotin-thiol (BSH) that reacts with benzylchlorides (or other thiol reactive groups) before and after the bicyclization step, (ii) diluting the reactions by at least one order of magnitude, (iii) adding streptavidin beads (iv) measuring the number of phage particles remaining after capture, whereby the number of phage retained on the streptavidin beads constitutes the yield of the bicyclization step (the fraction of phage particles that lost thiol-reactive groups during the bicyclization step.

In another aspect, the invention may comprise a genetically encoded library of ligands comprising a plurality of different polypeptide sequences, each forming a bicyclic structure with a linker as described herein. In some embodiments, at least two polypeptides P1 and P2 are separately encoded by DNA sequences. The plurality of different polypeptides may be modified with the same or different linkers. Each linker may be associated with a unique identifying tag, such as a silent genetic barcode.

The libraries may be pooled together to form a genetically encoded mixed library of complexes, produced by producing libraries of the complexes described herein. The mixed library may comprise at least two different peptide sequences (P1 and P2) each separately modified with at least two different linkers (L1, L2), forming at least four distinct complexes (P1L1, P1L2, P1L2, and P2L2). In some embodiments, linker L1 may be reacted with two peptides that are associated with pre-defined nucleic acid code B1 and linker L2 is reacted with two peptides that contain pre-defined nucleic acid code B2. The nucleic acid codes may comprise silent genetic barcodes, such as those described in WO2016061695-A1.

In another aspect, the invention comprises a method for identifying a complex as described herein wherein the polypeptide bicyclic structure is capable of binding to a ligand, the method comprising (i) contacting a library of complexes with the ligand, and (iii) selecting those complexes which bind to the ligand (iii) identifying the structure of a binding complex by sequencing a nucleic acid that encodes the structure of polypeptide and/or linker. In some embodiments, the library of complexes may comprise at least four distinct bicyclic structures, P1L1, P1L2, P1L2, P2L2 as described above.

In another aspect, the invention comprises a Nodal antagonist peptide comprising a bicyclic complex formed from a polypeptide comprising SPCQRGHMFC (SEQ ID NO. 105) or SYCKRAHKNC (SEQ ID NO. 4) and a linker comprising TSL6.

BRIEF DESCRIPTION OF THE FIGURES

For a better understanding of the present invention, as well as other aspects and further features thereof, reference is made to the drawings which form part of this specification together with the description.

FIG. 4A shows linkers TSL1 (1), TSL3 (2) and TSL6 (3). Sequences 1-6 are variable peptides to which these linkers may react with to form bicyclic structures.

FIG. 7A shows a bicyclic modification with a linker of medium length (3 carbon atoms), while

FIG. 11 shows the stability of a number of bicyclic peptide compositions in two different degradation conditions.

DETAILED DESCRIPTION

In one aspect, the invention comprises a method of synthesizing a bicyclic peptide library comprising two distinct modification steps. A first step comprises creating an intermediate complex by ligating a first end of a linker to the terminus of a peptide displayed on a carrier, through ligation chemistry in an aqueous environment. The peptide terminus may be the N or the C terminus. After an optional purification step, a second step comprises exposure of the intermediate complex to reaction conditions to induce an intramolecular bicyclization reaction where two reactive groups at a second end of the linker each independently react with side chains of amino acids in the peptide sequence.

In some embodiments, the bicyclic peptide carrier may comprise phage, mRNA, DNA, ribosome, bacteria, yeast, beads made of synthetic polymers such as PEG or polystyrene or any other genetically-encoded biological display technology or synthetic encoded peptide library technology known in the art. In some embodiments, the carriers comprises display set of genetic sequences which encode a random peptide library of different chemical compositions. In another embodiment, the display set of gene sequences comprises a focused genetic library that encodes a focused sub-set of peptide sequences of different chemical compositions, such as those generated by random mutagenesis, for example.

The display set of gene sequences may be paired with a specific linker, such that the second set are linked with a chemical structure of a linker molecule, such as a linker of different size or composition, or linkers that are stereoisomers, diastereomers or enantiomers.

Either or both of the two steps—ligation and bicyclization—can be a chemical or enzymatic modification of the peptides. In some embodiments, both modifications are chemical conjugation techniques specific to N-terminus or specific N-terminal amino acids and a distinct set of amino acids in the peptide. The chemical modification used for ligation, for example, can result in the formation of oxime at an oxidized N-terminal serine. Ligation can employ other N-terminus or C-terminus specific chemistries known in the art.

Figure 1A:
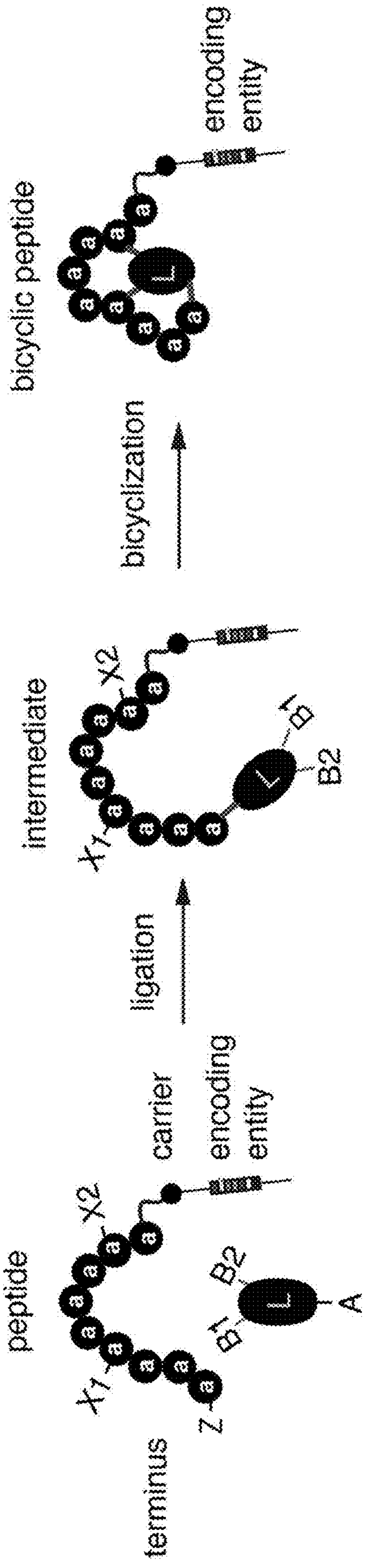
FIG. 1A shows a schematic depiction of carrier with peptide, a linker and encoding entity such as DNA or RNA.
Figure 1B:
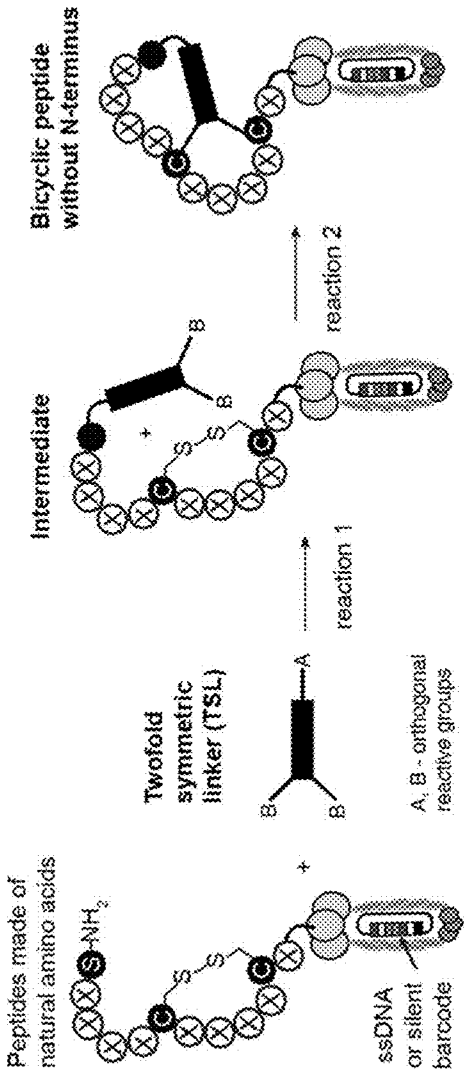
FIG. 1B shows a conceptual outline of the bicyclization process that starts from phage libraries of varied peptides.

A schematic representation of the carrier with peptide and the linker is shown in FIG. 1A. The peptide terminus Z, which may be either N- or C-terminus, reacts with a linker L first end A. The peptide has reactive side chains X1 and X2 which react with two functional groups B1 and B2 on a second end of the linker. The linker L may comprise an aliphatic chain, and may also include an ester, a phenyl, an amine or the like.

In some embodiments, the first end A is first ligated with the peptide terminus Z resulting in a linear intermediate complex identified in FIG. 1A, which is then followed by bicyclization. The ligation reaction may include those reactions which modify oxidized serine (oxaloyl) through a carbon-carbon bond forming process such as the Wittig reaction. One preferred embodiment of the bicyclization step comprises alkylation of cysteine or any other suitable method to modify a peptide or protein in a specific location.

Figure 1C:
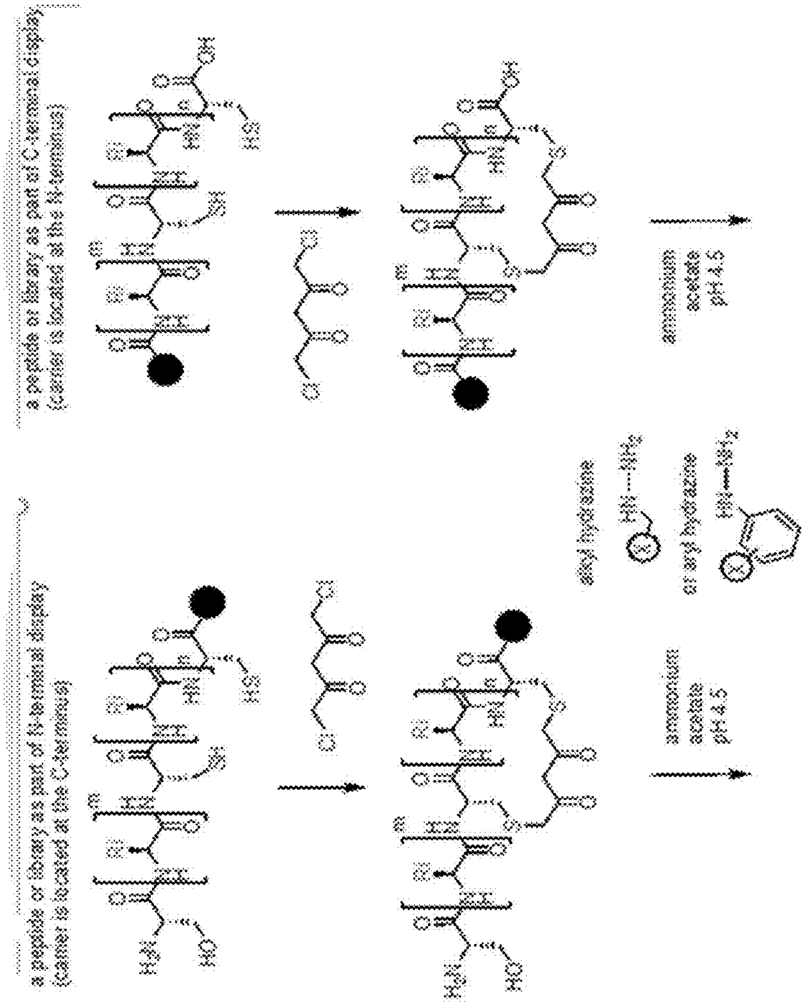
FIG. 1C shows two schemes of reacting a polypeptide where a carrier is located at the C-terminus (left) and at the N-terminus (right).
Figure 1D:
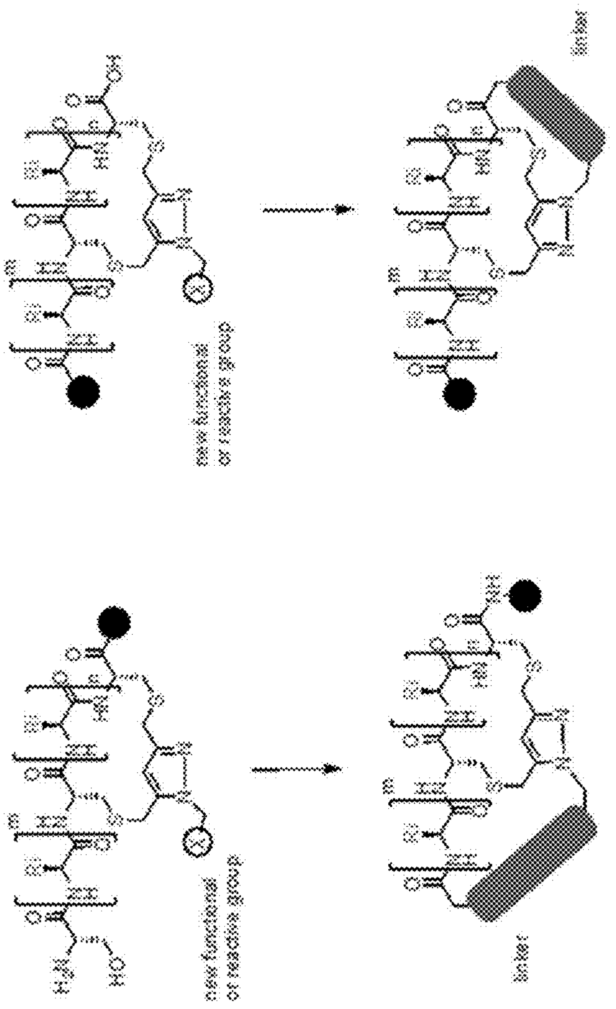
FIG. 1D is a continuation of FIG. 1C.

In alternative embodiments, shown schematically in FIGS. 1C and 1D, a first step comprises a reaction with a diketone that forms a first ring and simultaneously introduces a uniquely reactive group. The diketone is preferably a 1,3 diketone. The intermediate monocyclic peptide formed in this reaction is uniquely stable and may be purified and stored without any deterioration of the reactive group. The intermediate monocyclic peptide bearing the diketone group may then be reacted with a linker molecule that comprises a 1,3-diketone-reactive group, such as an alkyl or aryl hydrazine at one end, and another group at the other end that can undergo chemical or enzyme-catalyzed ligation with the terminus of the peptide to induce formation of the second ring ("bicyclization"). Ligation at the peptide terminus may occur first, resulting in a linear intermediate. Alternatively, reaction with the diketone may occur first, resulting in a branched intermediate.

For example, a display peptide with two internal cysteine residues in the sequences can be reacted with 1,5-dichloropentadione-2,4 at an alkaline pH, for example about pH 8 or 9, to introduce a 1,3-diketone group into the peptide. The 1,3,-diketone group can be then reacted with a linker comprising an alkyl or aryl hydrazine, which introduces a functional group that completes a subsequent bicyclization reaction with the N-terminus of the peptide. For example, the said peptide containing 1,3-diketone group can be modified at the N-terminus to introduce the hydrazine linker, and then bicyclization via an intramolecular reaction between hydrazine at the N-terminus and 1,3-diketone ligated to the side chains. Alternatively, the sequence of the reaction is reversed where a linker that contains N-terminal reactive group is reacted with 1,3-diketone in acidic pH. Then, oxidation of the terminus at neutral pH and change of the environment to acidic pH 4.5 triggers bicyclization via reaction with N-terminus.

In all cases, it is preferred that the two steps—ligation and bicyclization—occur in conditions that are independent of one another. Such independence allows purification of the intermediate product and minimize side reactions. Some embodiments involve the use of reactions that require different pH values. For example, formation of oxime at an oxidized N-terminal serine occurs at acidic pH, about pH 3, and can be catalyzed by 0.1% trifluoroacetic acid (TFA). These conditions are tolerated by phage-displayed libraries and other genetically encoded peptide libraries such as RNA-displayed libraries. The subsequent bicyclization reaction could be any intermolecular reaction with side chains of amino acids that occurs at a higher pH. Suitable reactions may include nucleophilic substitutions between thiols and thiol reactive groups such as halobenzyl, haloacetamide, nucleophilic aromatic substitutions, or Michael additions of thiols to conjugated alkenes and/or allenamides. It is also possible to use other known reactions that occur at alkaline pH with side chain residues of Lys, Tyr or other amino acid side chain residues.

In alternative embodiments, the ligation and bicyclization steps are separated through the use of protection-deprotection reactions. For example, formation of a C—C bond at an oxidized N-terminal serine via a Wittig reaction occurs at about pH 7 to about pH 8. It is known that the Wittig reaction does not perturb the S—S disulphide that protects thiol residues. Wittig reactions are tolerated by phage-displayed libraries and other genetically encoded peptide libraries such as RNA-displayed libraries. After ligation and purification, the bicyclization reaction is triggered by reduction of the disulphide and ligation between thiol and thiol reactive group, which may occur at about pH 7 to about pH 8. Many linkers may be designed which combine a stabilized ylide to be used in a Wittig ligation reaction with thiol reactive groups for nucleophilic substitutions, nucleophilic aromatic substitutions or Michael additions or other well known reactions for the bicyclization step.

In some embodiments, the carrier comprises an identifier, which is preferably a variable nucleic acid code identifier. The identifier may be silent so as to not encode any peptide borne on the carrier exterior. Alternatively, the identifier may be such that all variants of the identifier encode identical or substantially similar peptides. In this latter case, referred to "silent barcoding" technology, the method involves producing a bacteriophage display system on particles that contain DNA of different compositions inside bacteriophage particle and display peptides of identical composition. In some embodiments, the carriers are viral or bacteriophage virions of identical external chemical composition containing variable nucleic acid codes comprising degenerate DNA tags within the genome, packaged inside these particles. The genome of the virus or phage is manipulated in a manner that does not produce changes in chemical composition of the virion coat, such as, the use of degenerate codons in virion coat coding regions, change in DNA sequence that encodes excised sequences, change in DNA sequence that does not encode expressed protein sequences or change in DNA sequence that encodes components that are not incorporated into the virion coat. Thus, there may be provided a carrier library comprising a plurality of carriers (such as phages or viruses), wherein all the carriers are externally chemically identical (prior to modification eg. the attachment of any ligands), but contain distinct nucleic acid identifiers therein.

In another aspect, the invention may comprise a method of selecting a genetically-encoded modification of a peptide library by using a unique identifier, preferably a silent genetic barcode, associated with a specific bicyclic structure. In some embodiments, multiple libraries of carriers are produced, each carrying a unique silent genetic barcode, and each displaying a polypeptide. Each library is then modified with a different linker, as described herein, to produce a bicyclic structure unique to the linker used. The libraries are then combined to produce a mixed library wherein each linker-specific bicyclic structure may be identified by the barcode. The mixed library may then be screened to select a peptide with a desired sequence and bicycle topology, which may then be identified by sequencing the genetic barcode (or otherwise identifying the identifier).

Figure 2:
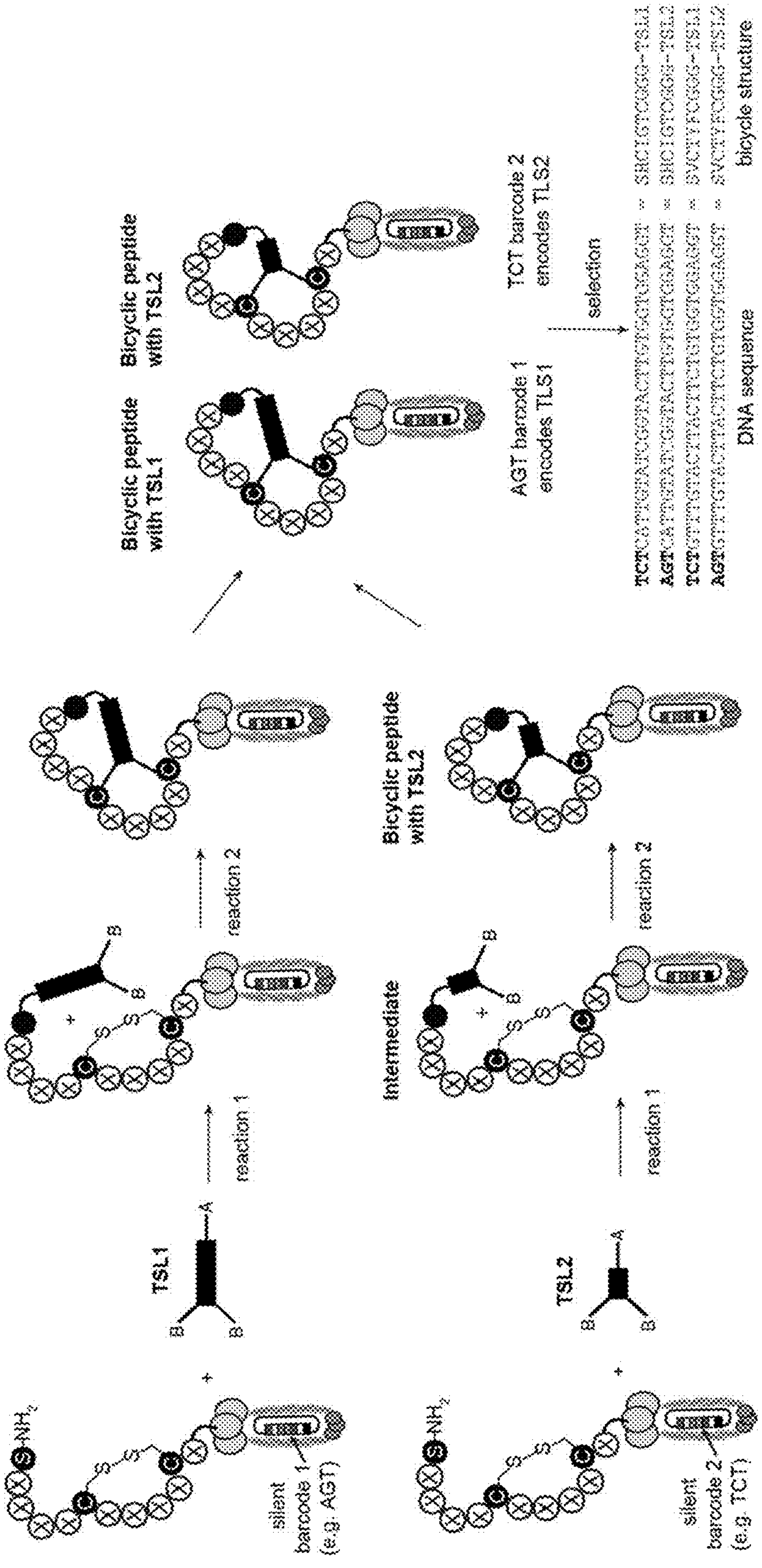
FIG. 2 shows a scheme of chemical bicyclization by linkers TSL1 and TSL2 and simultaneous encoding of different linkers with two different silent genetic barcodes TCT and AGT.
Figure 3:
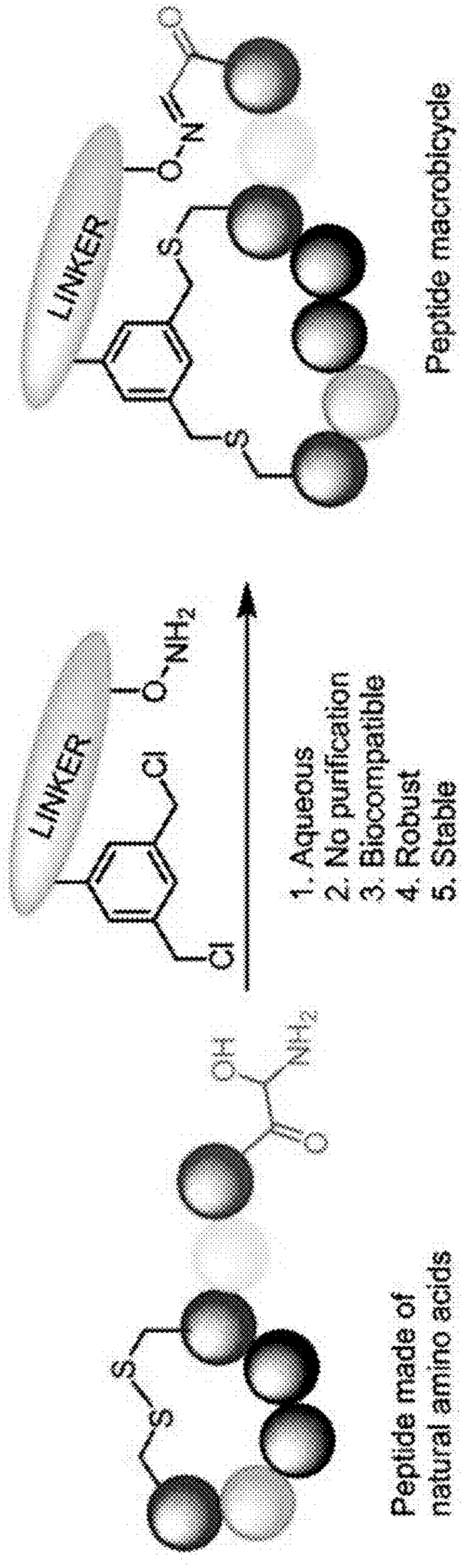
FIG. 3 shows a specific example of a linker that uses formation of an oxime on an N-terminal serine and benzylchloride as reactive groups A and B.

For example, as shown schematically in FIG. 2, a first carrier carries a first silent nucleic acid code (barcode) and a DNA sequence which encodes a peptide. A second carrier carries a second silent nucleic acid code, different from the first code, and a DNA sequence which encodes a peptide, which may be the same or different from the first peptide. The first carrier peptide is modified with a first linker (TSL1), while the second carrier is modified with a different linker (TSL2). After ligation and bicyclization, the two resulting different bicyclic structures are distinguishable by the first and second nucleic acid codes.

In another aspect, the invention may comprise a method of identifying a drug candidate comprising: preparing a genetically-encoded bicyclic peptide mixed library as described herein and screening the library with a putative receptor molecule to identify those bicyclic peptides which bind to the receptor molecule. The bicyclic peptides which bind to the receptor are then identified by enriching and sequencing the silent nucleic acid code and the sequence encoding the peptide.

In another aspect, the invention may comprise a method of synthesizing a genetically-encoded chemical bicyclic peptide library comprising: inserting, into multiple independent vectors in a substrate, a redundant set of gene sequences encoding a peptide linker, such that gene sequences produce identical or closely related peptide sequences ("linkers") upon translation; inserting, into each vector, a second set of gene sequences encoding a genetically diverse insert, such that a diverse set of peptides ("library"), is expressed upon translation; expressing and amplifying the first and second gene sequences such that a translation product comprises non-variable linker and variable peptide library is synthesized; and modifying each peptide library by a distinct TSL and combining multiple modified libraries to produce a library in which chemical modification is encoded genetically.

US Patent Publication 2013/050083 to Derda et al., the entire contents of which are incorporated herein by reference where permitted, describes a method for quantification of chemical modifications of genetically-encoded peptide libraries and selection of new strategies for effective modification. These methods may be used to quantify the yield of any one or all of the reactive steps described herein, based on the presence or absence of a reactive group which would be consumed in the reaction.

Techniques for genetic encoding of chemical post-translational modifications for phase-displayed libraries are described in PCT patent application no. WO2016061695A1, the entire contents of which are incorporated herein by reference, where permitted.

EXAMPLES

To gain a better understanding of the invention described herein, the following examples are set forth. It should be understood that these examples are for illustrative purposes only. Therefore, they should not limit the scope of this invention in any way.

Figure 4B:
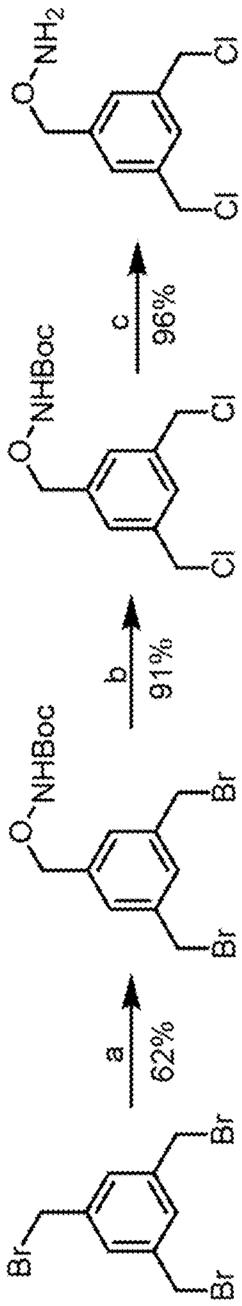
FIG. 4B shows a synthetic scheme for linker TSL1.
Figure 4C:
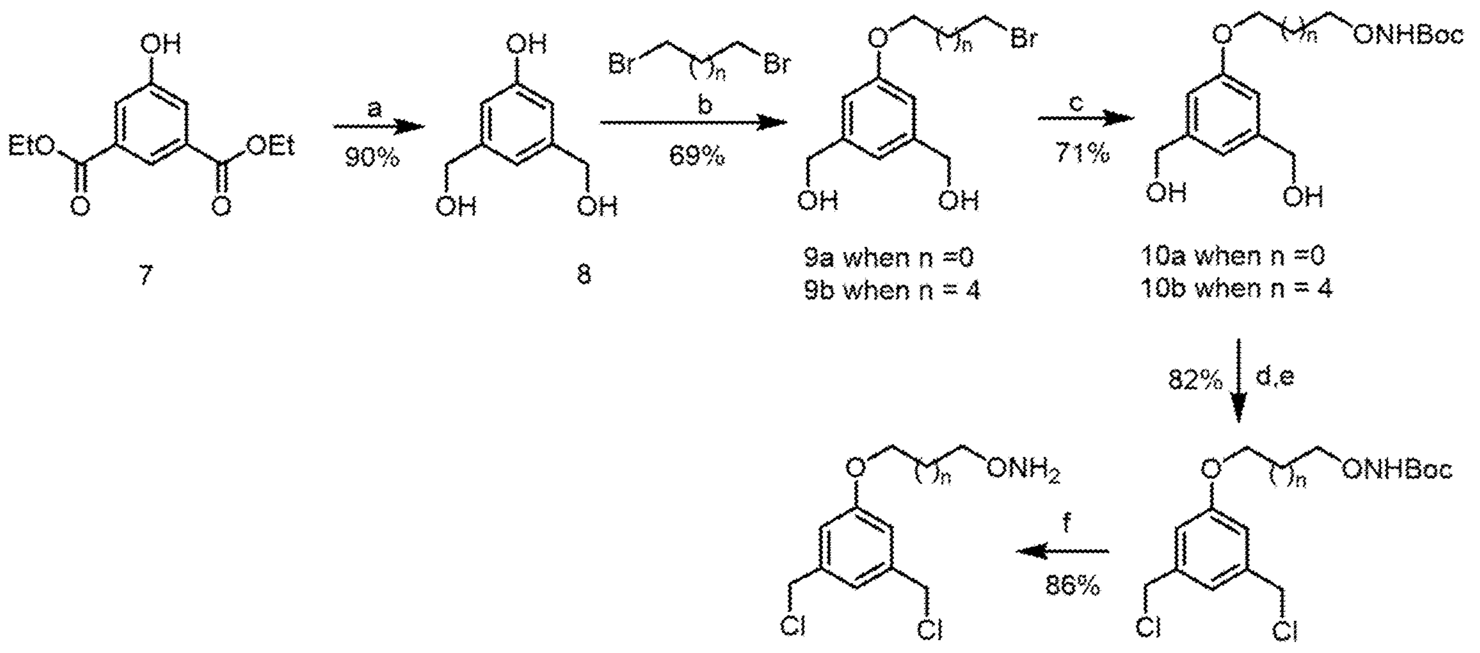
FIG. 4C shows a synthetic scheme for linkers TSL3 and TSL6.

Example 1. Synthesis of linkers for bicyclization. Cross-linkers 1 (TSL1), 2 (TSL3) and 3 (TSL6) as shown in FIG. 4A were designed based on oxime formation and cysteine S-alkylation chemistries. These reactions involve bioorthogonality, clean and high yielding reactions with fast kinetics. The synthetic steps are outlined in FIGS. 4B and 4C. The difference between the three are primarily the number of carbon atoms in the linking chain.

Figure 5A:
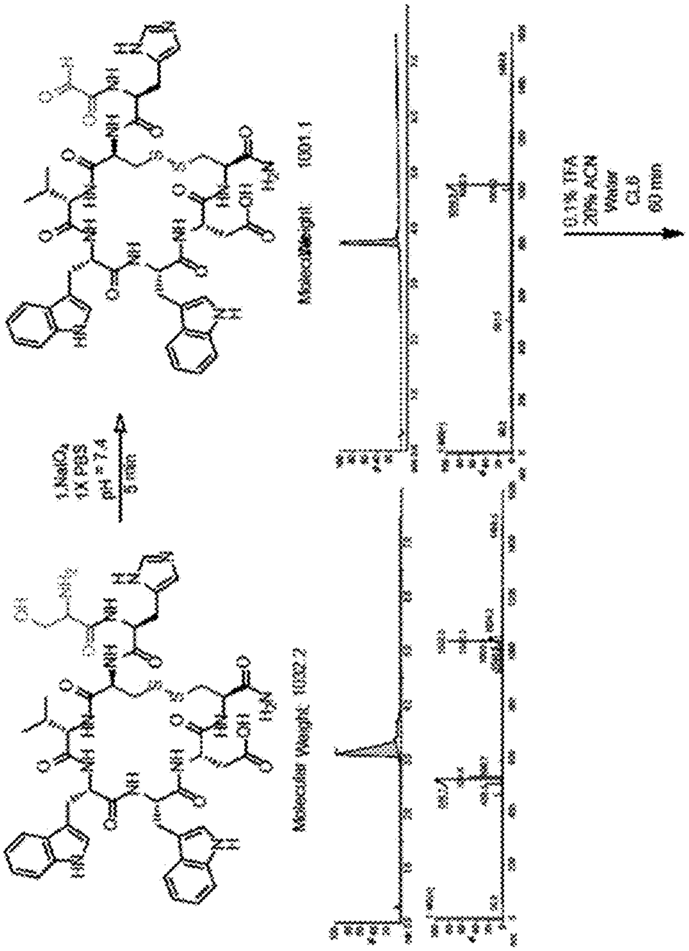
FIG. 5A shows a modification of oxidized peptide SHCVWWDC (SEQ ID NO. 1) with TSL6.
Figure 5B:
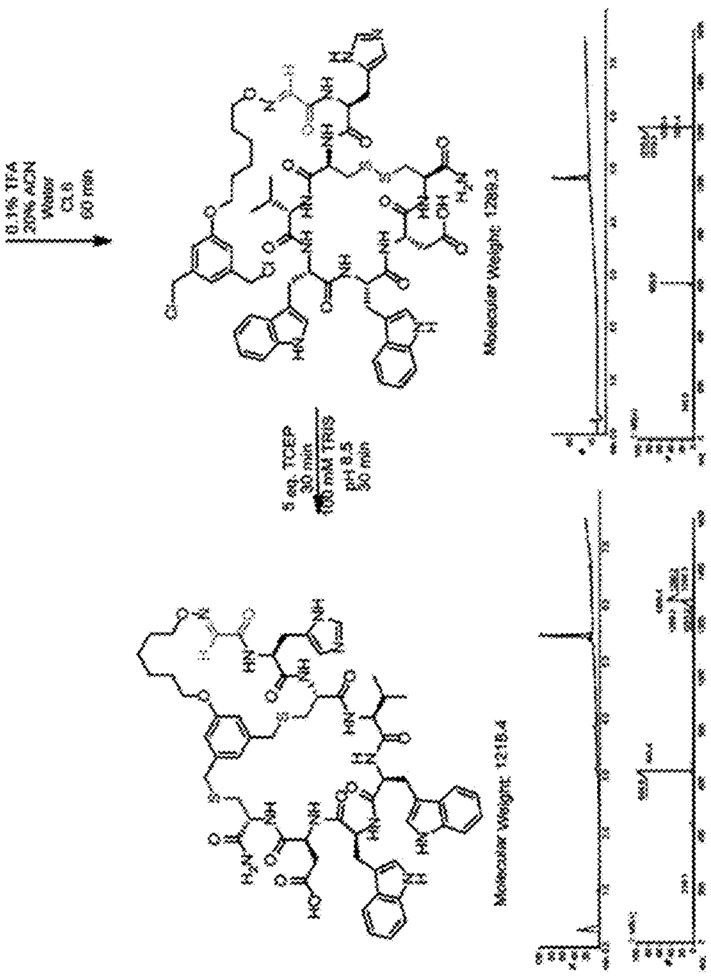
FIG. 5B is a continuation of FIG. 5A.
Figure 6:
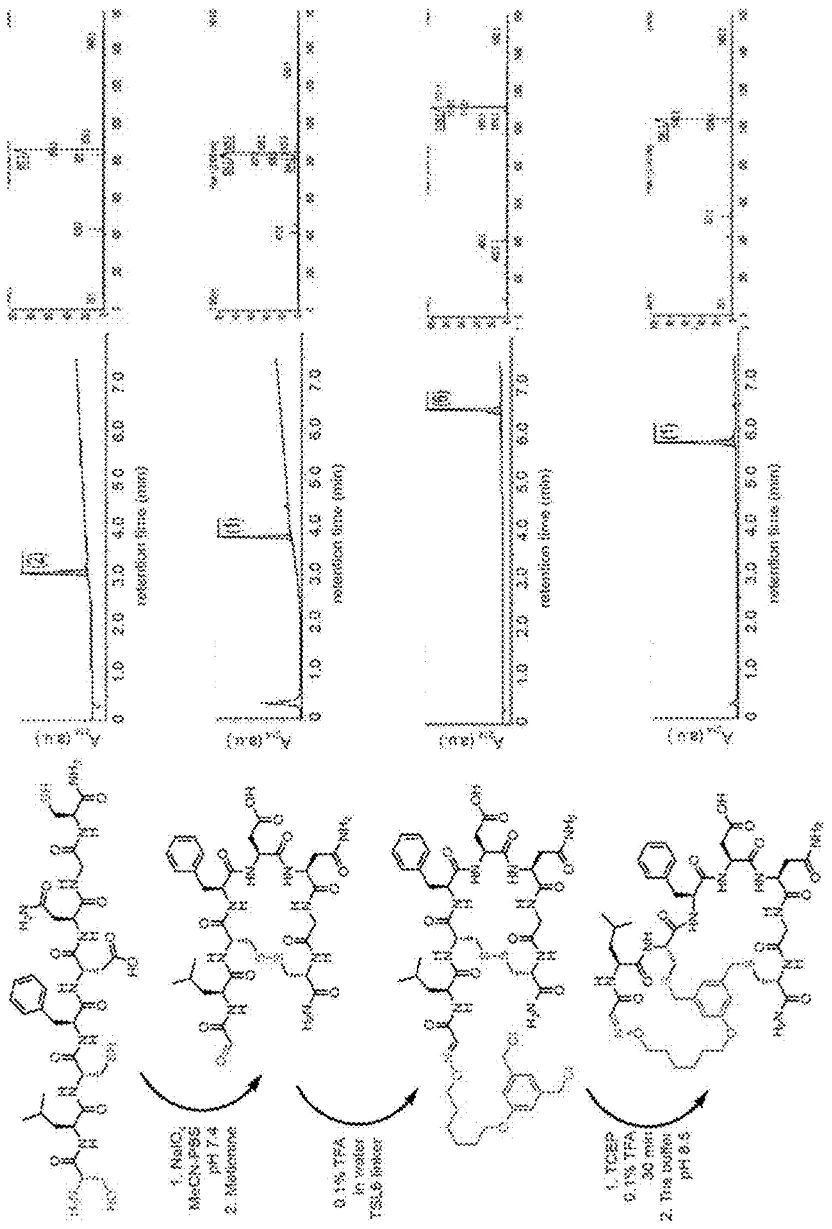
FIG. 6 shows a modification of reduced peptide SVCFDNGC (SEQ ID NO. 2) with TSL6.

Example 2. Modification of reduced peptide SHCVWWDC (SEQ ID NO. 1) with TSL6 linker. Details of modification are outlined in FIGS. 5A and 5B. The ligation step occurs at a low pH. Purification at aldehyde step or after ligation can be afforded by size exclusion column. Low pH at a reduction step maximizes the yield of the bicyclization reaction. Increase in pH after the reduction cleanly affords the bicyclic products and no visible unreacted starting material or byproducts by LCMS. Characterization by LCMS confirmed the identity of all intermediates at each step.

Example 3. Modification of reduced peptide SVCFDNGC (SEQ ID NO. 2) with TSL6 linker. Details of modification are outlined in FIG. 5. Important details of chemistry: low pH at the ligation step. Purification at aldehyde step or after ligation can be afforded by size exclusion column. Low pH at a reduction step maximizes the yield of the bicyclization reaction. Increase in pH after the reduction cleanly affords the bicyclic products and no visible unreacted starting material or byproducts by LCMS. Characterization by LCMS confirmed the identity of all intermediates at each step.

Figure 7A:
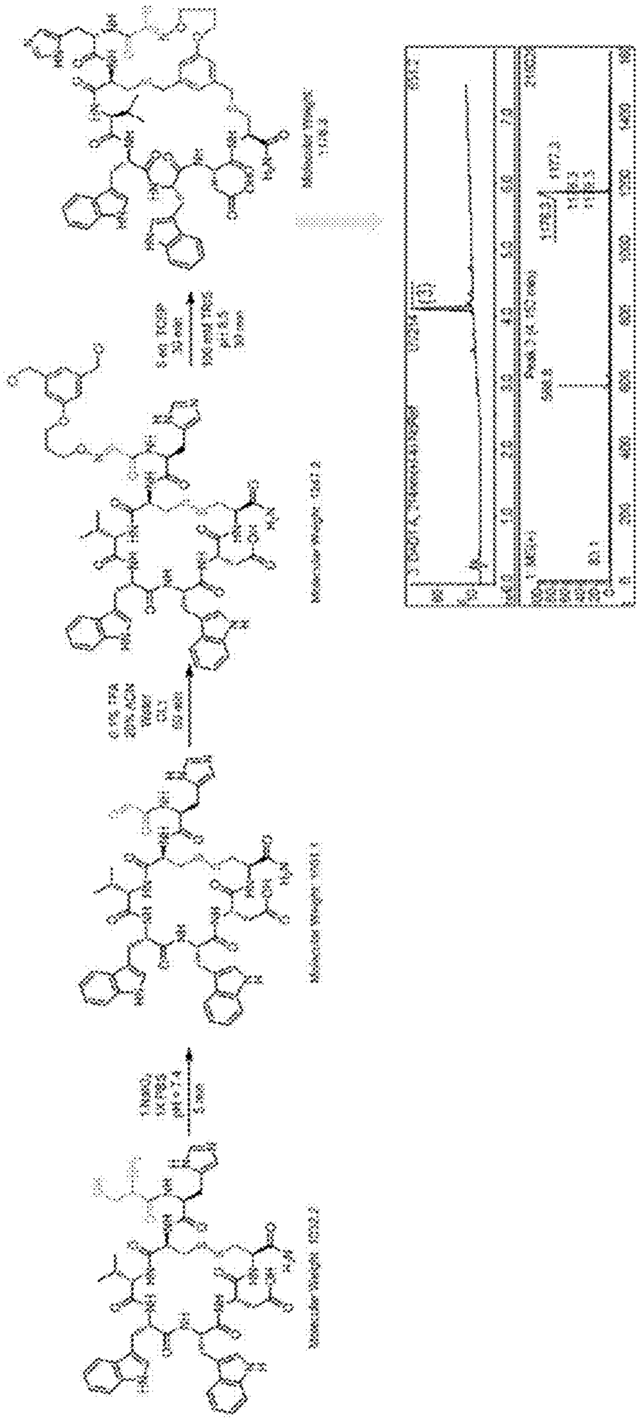
Figure 7B:
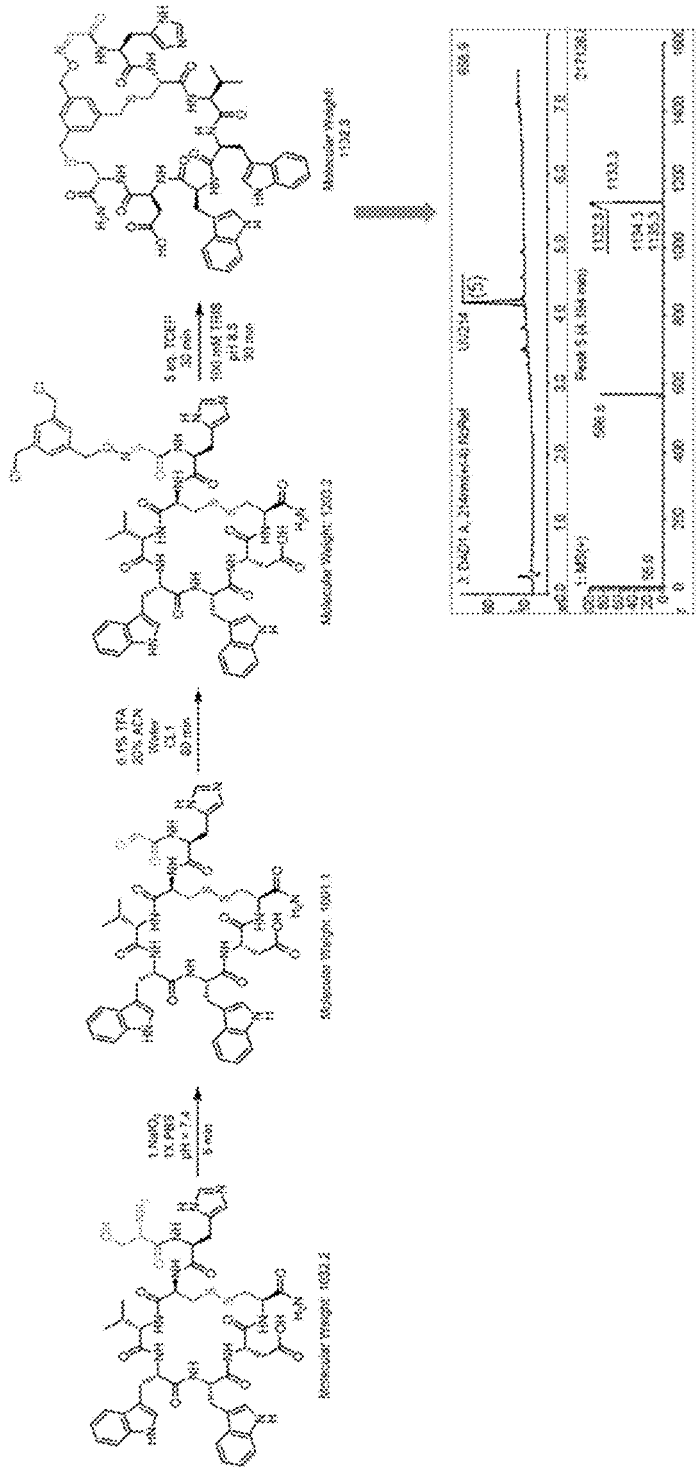
FIG. 7B shows a bicyclic modification with a short linker (1 carbon atom).
Figure 8A:
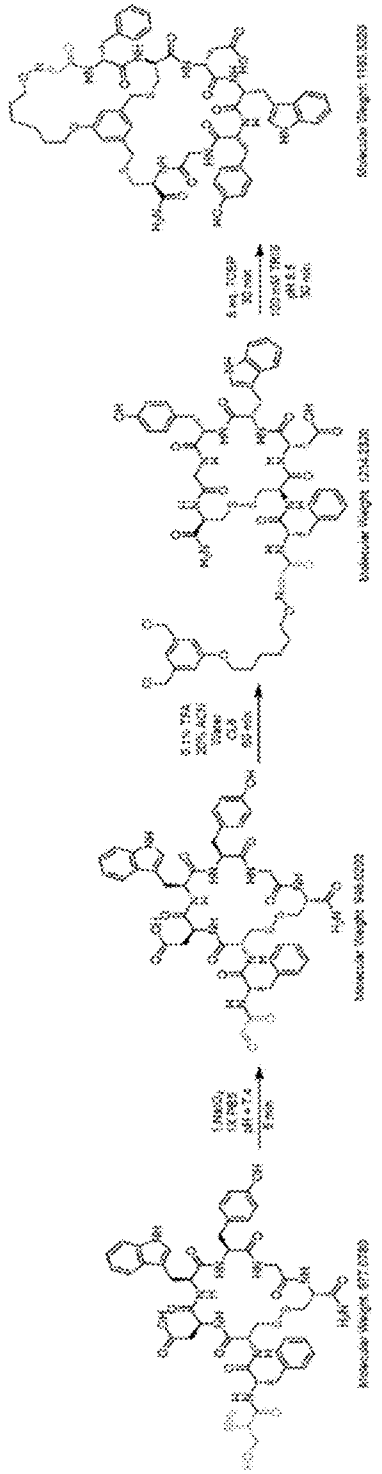
FIG. 8A shows a SFCDWYGC (SEQ ID NO. 104) modification with TSL-6 (6 carbon atom linker).
Figure 8B:
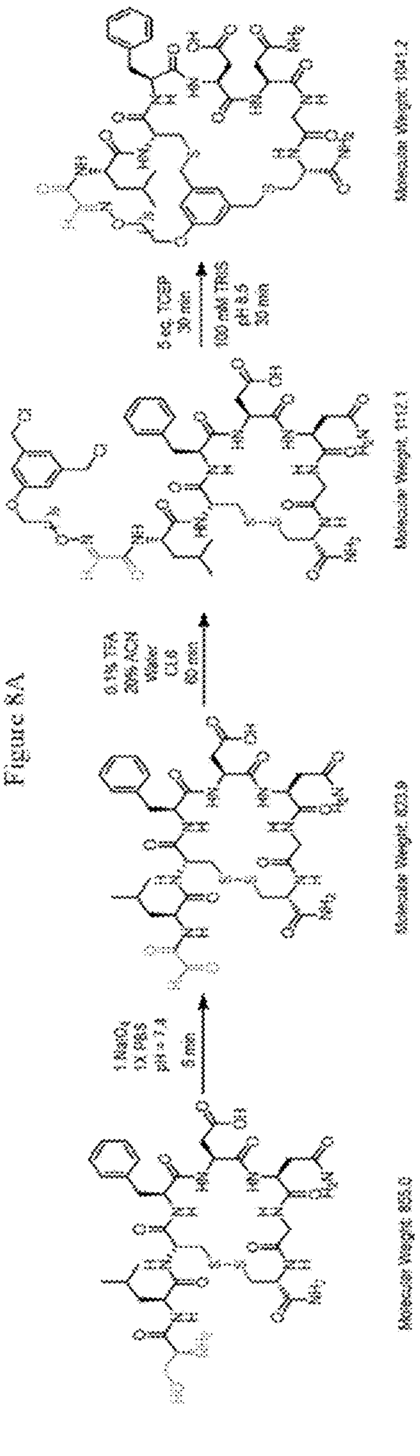
FIG. 8B shows a SLCFDNGC (SEQ ID NO. 105) modification with TSL-6.
Figure 8C:
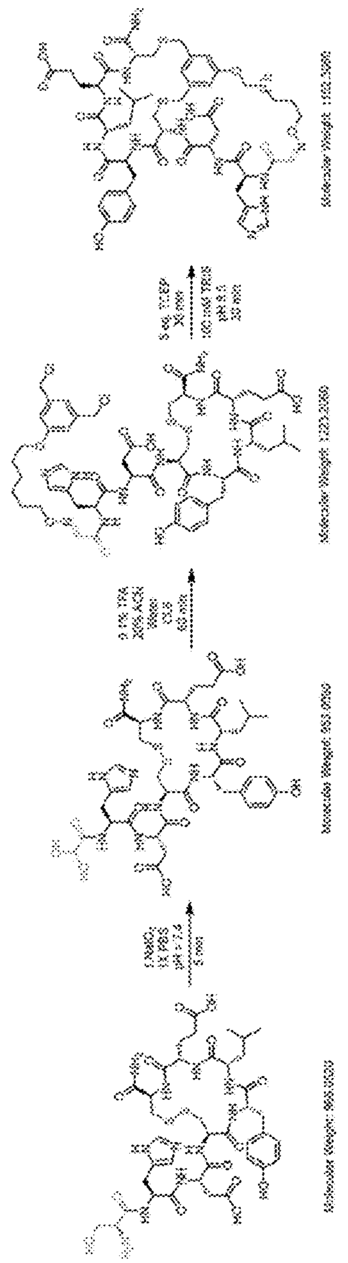
FIG. 8C shows a SHDCYEC (SEQ ID NO. 106) modification with TSL-6.
Figure 8D:
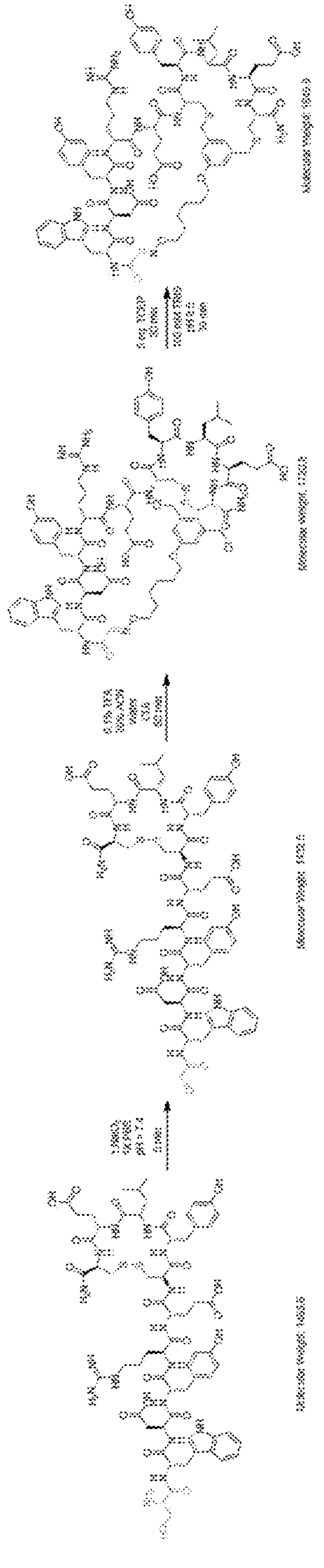
FIG. 8D shows a SWDYRECYLEC (SEQ ID NO. 3) modification with TSL-6.
Figure 8E:
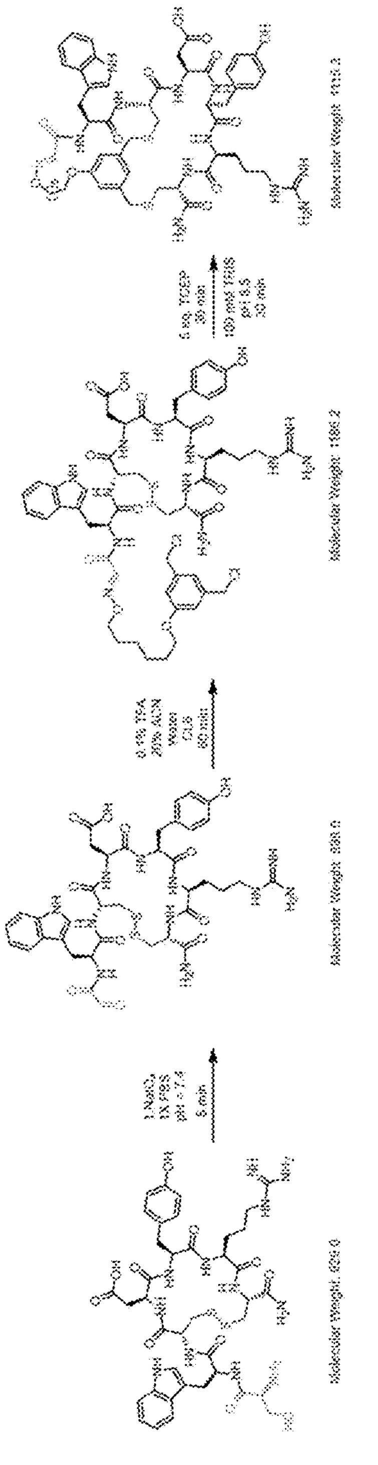
FIG. 8E shows a SWCDYRC (SEQ ID NO. 107) modification with TSL-6.
Figure 8F:
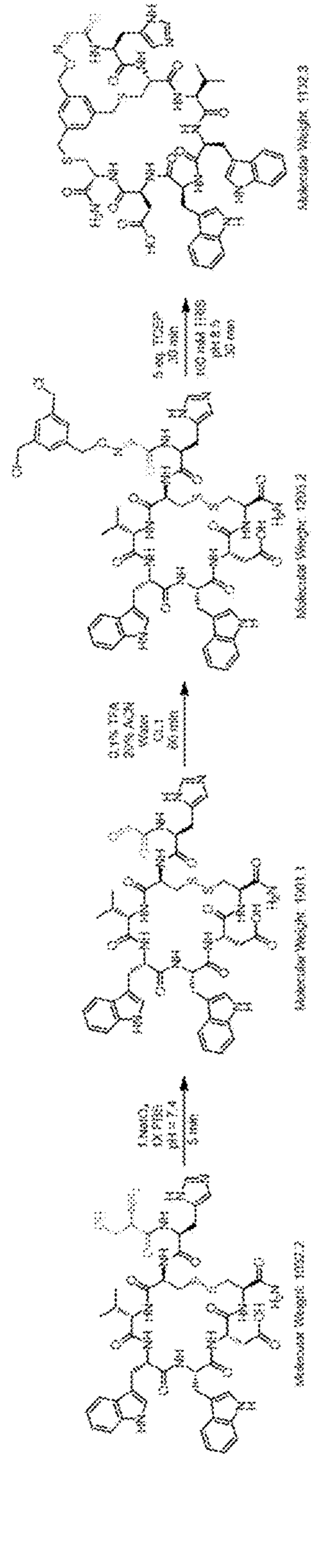
FIG. 8F shows a SHCVWWDC (SEQ ID NO. 1) modification with TSL-1.
Figure 8G:
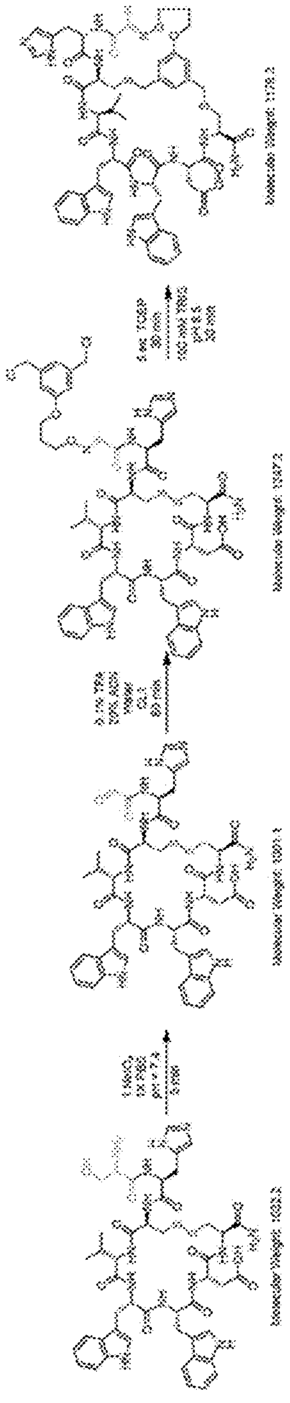
FIG. 8G shows a SHCVWWDC (SEQ ID NO. 1) modification with TSL-3.

Example 4. Modification of diverse set of peptides with several TSL-linkers. A series of peptide sequences having a serine residue at the N-terminus and two cysteines in downstream positions were selected. Oxime ligation based chemistry was used to recognize the oxoaldehyde generated from the periodate mediated oxidation of the N-terminal serine and later to catch the two cysteines by cross-linking strategy to eventually form a conformationally rigid peptide macrobicycle using the conditions described in Examples 2 or 3. Summary of reactions on multiple different peptides, as described in FIGS. 8A-8G, confirms that ligation and bicyclization chemistry occurs effectively on a variety of peptide sequences. Modification with TSL linkers that have decreasing number of atoms proceeded effectively even when the resulting size of the second ring was formed by only one amino acid (FIG. 7B). These results shows that there should be no constraints on the size of peptide loops and few constraints on the geometry of the TSL.

Figure 9B:
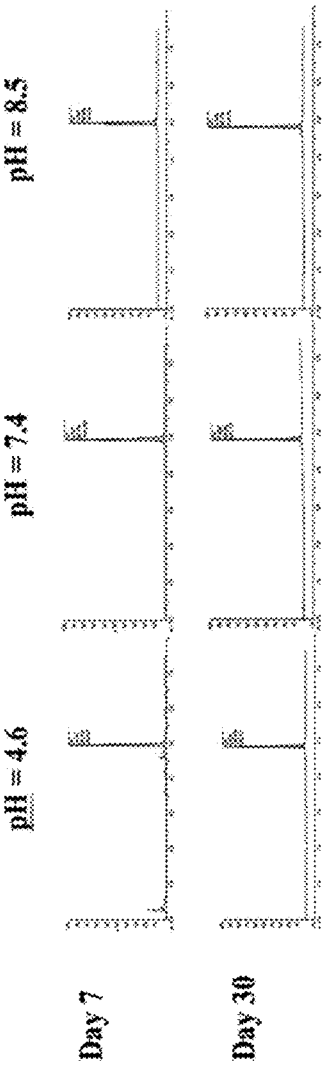
FIG. 9B shows graphs demonstrating stability of the complex in buffered medium of pH 4 7 and 8.5 at room temperature for a month.
Figure 9A:
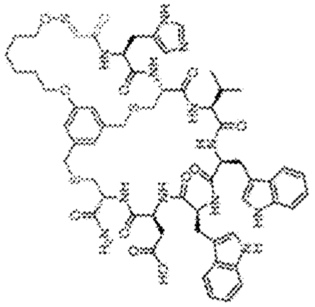
FIG. 9A shows bicycle SHCVWWDC (SEQ ID NO. 1)-TSL6.
Figure 10A:
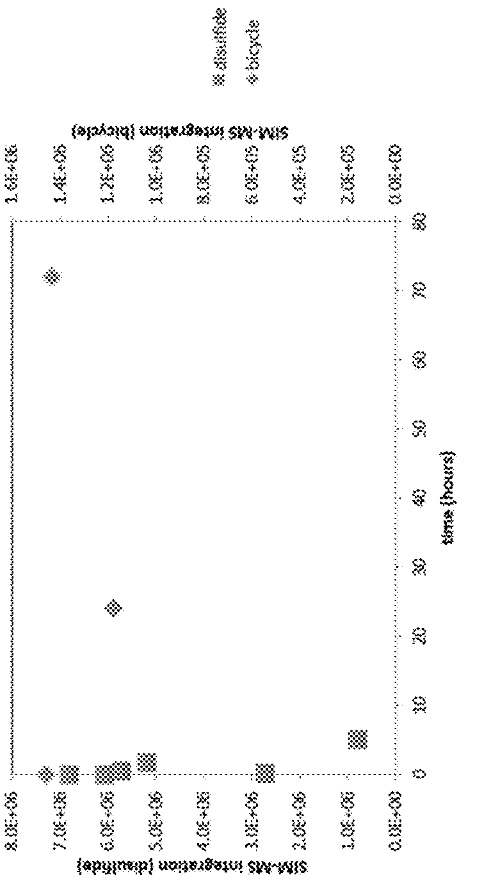
FIG. 10A shows stability of bicycle shown in FIG. 9A to incubation in fetal bovine serum (FBS) at 37° C. The mixture was analyzed by ion-selective LCMS. Intensity of the bicycle ion does not diminish even after 3 days (~70 hours) of incubation in FBS at 37° C. whereas 90% disulphide SHCVWWDC (SEQ ID NO. 1) peptide is degraded after <5 hours.

Example 5. Stability of the bicycles in buffers and biological medium. Bicyclic peptides formed from sequence SHCVWWDC (SEQ ID NO. 1) by modification with TSL3 linker were incubated in buffered medium of pH 4, 7 and 8.5 at room temperature for a month (FIG. 9). We observed no changes in LCMS indicating no degradation of bicycle product in any of these conditions. SHCVWWDC (SEQ ID NO. 1)-TSL3 bicycle was incubated in fetal bovine serum (FBS) at 37° C. and the integrity of the bicycle was tested by LCMS. Using ion-selective LCMS, the bicycle remains unchanged in FBS even after 3 days of incubation in FBS at 37° C. In contrast ion-selective LCMS demonstrated that 90% of cyclic peptide disulfide SHCVWWDC (SEQ ID NO. 1) was degraded in FBS after 300 minutes (FIG. 10A).

Figure 10B:
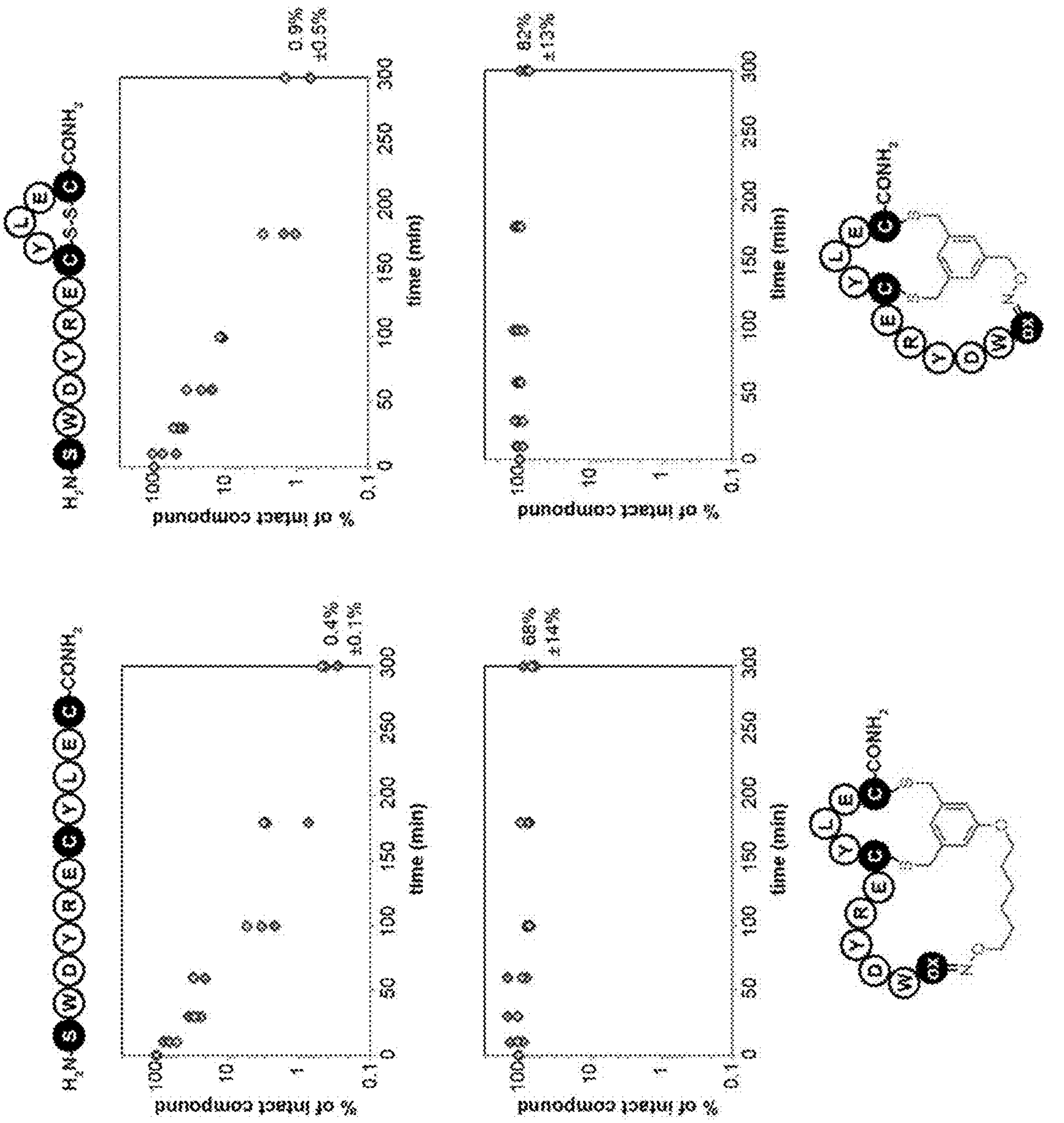
FIG. 10B shows stability of the bicycle to incubation in Pronase™ protease mixture at 37° C. Linear, disulfide and two bicycle compounds made from TSL-1 and TSL-6 linker were incubated with Pronase™ for the indicated period of time (up to 5 hours). The reaction was diluted and analyzed by Ion selective MS-UPLC. The numbers indicate % of intact compound remaining after 5 hours of digestion.

In another rigorous stability test, an aggressive cocktail of endo- and exoproteases (Pronase) were used to digest linear sequence SWDYRECYLEC (SEQ ID NO. 3), its disulfide derivative and two bicyclic derivatives of this sequence modified with TSL1 And TLS6 linker (FIG. 10B). After 5 hours of incubation at 37° C. only 0.4±0.1% of linear and 0.9±0.4% of linear and disulfide peptide remain undigested. In the same conditions, after 5 hours of proteolytic digestion 68±14% of TSL6-SWDYRECYLEC (SEQ ID NO. 3) bicycle and 82±13% of TSL1-SWDYRECYLEC (SEQ ID NO. 3) bicycle remain intact (FIG. 10B). The latter observation extrapolates the half life stability of TSL1-SWDYRECYLEC (SEQ ID NO. 3) bicycle to be ~24 hours.

FIG. 11 demonstrates the generality of this observations in 12 other bicyclic peptide compositions in two different degradation conditions. FIG. 11*a* describes the sequences and abbreviated names of reagents used for modifications (TSL-1, TSL-3 and TSL-6 correspond to structures 1, 3 and 6 in FIG. 4A). Alphanumeric designations are used to describe the products. FIG. 11*b* shows the example of time-resolved measurement of stability 5 hours at 36° C. and end-point measurement of stability after 5 hours. FIG. 11*c* summarizes the end-point measurements (at 5 hours at 36° C.) in two different proteolytic conditions: in Pronase and in fresh mouse serum. FIGS. 11*c* and 11*d* compare the stability of bicyclic peptides to some known in the art cyclic and bicyclic structures. This comparison shows surprising non-obvious benefits of 14f, a compound produced by TSL-6 modifier reported herein and 16j known-in-the-art compound (*J. Med. Chem.* 2018, 61 (7), 2823-2836) produced from a similar peptide sequence by TBMB modifier. Bicyclic compound 14f is 10 times more stable to Pronase treatment than 16j. Another comparison between 13i and 13e, again demonstrate the benefits of TSL-6 when compared to known in the art cyclization through perfluoro arenes described in WO2014052650A2.

Example 6. Production of genetically-encoded bicycle library by modification of the phage displayed libraries of peptides and validation of modification by capture agents.

Figure 12:
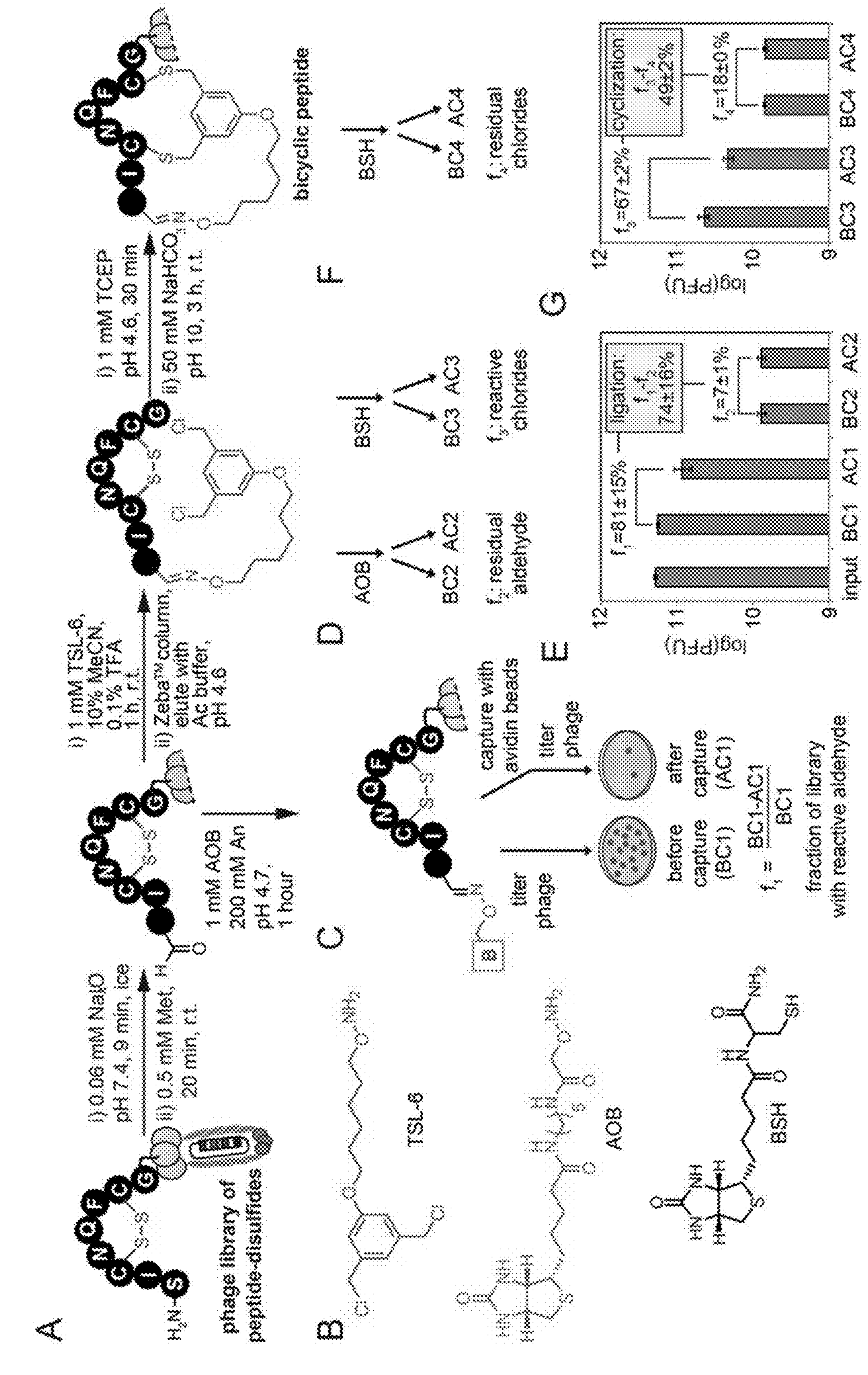
FIG. 12 shows a schematic depiction of modification of phage libraries of peptides using a TSL6.
Figure 13:
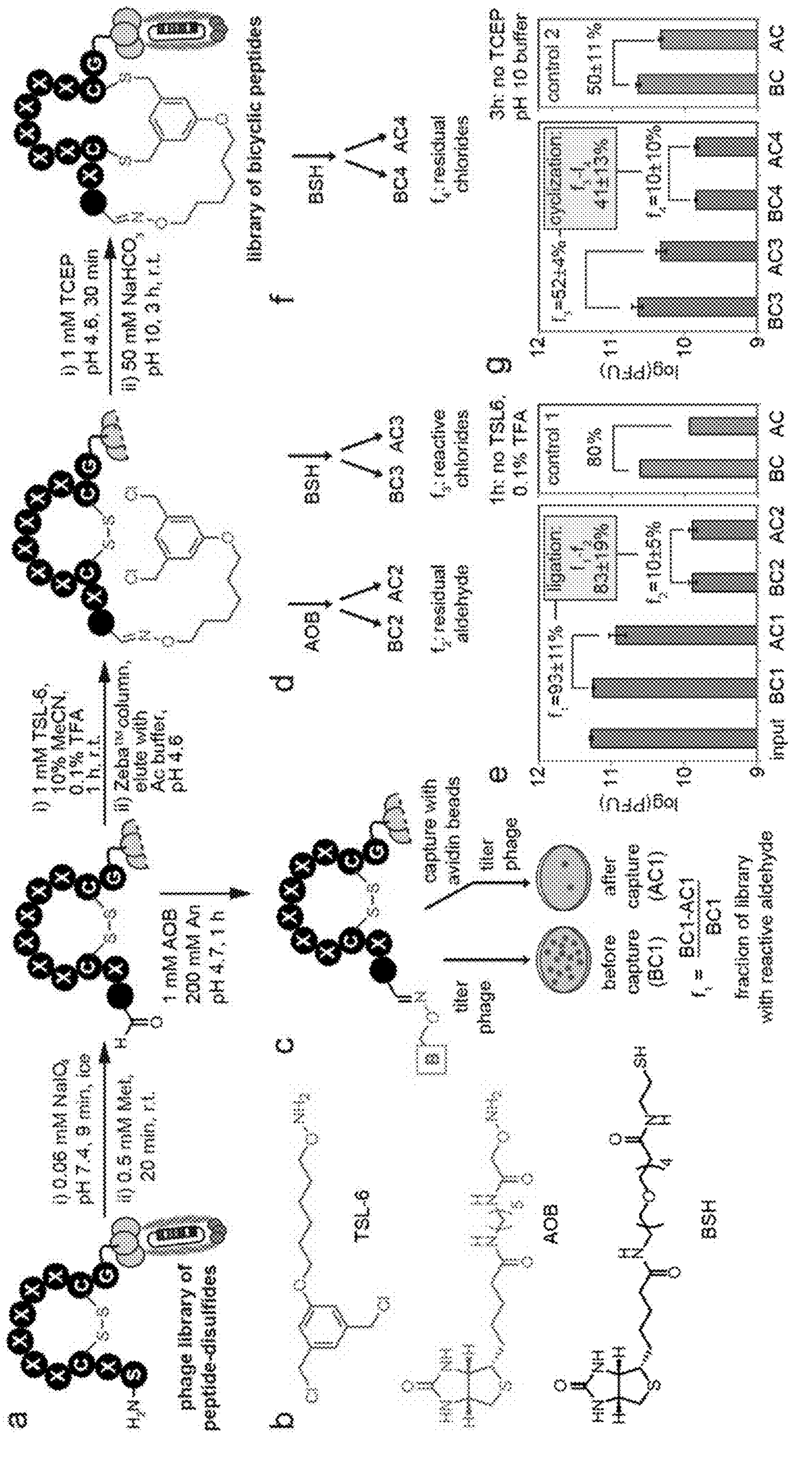
FIG. 13 and FIG. 14 show schematic examples of modification of a large phage library SxCxxxxxxC using a TSL1, TSL3 or TSL6 linker and show a generality of this approach for any library and any linker geometry.
Figure 14:
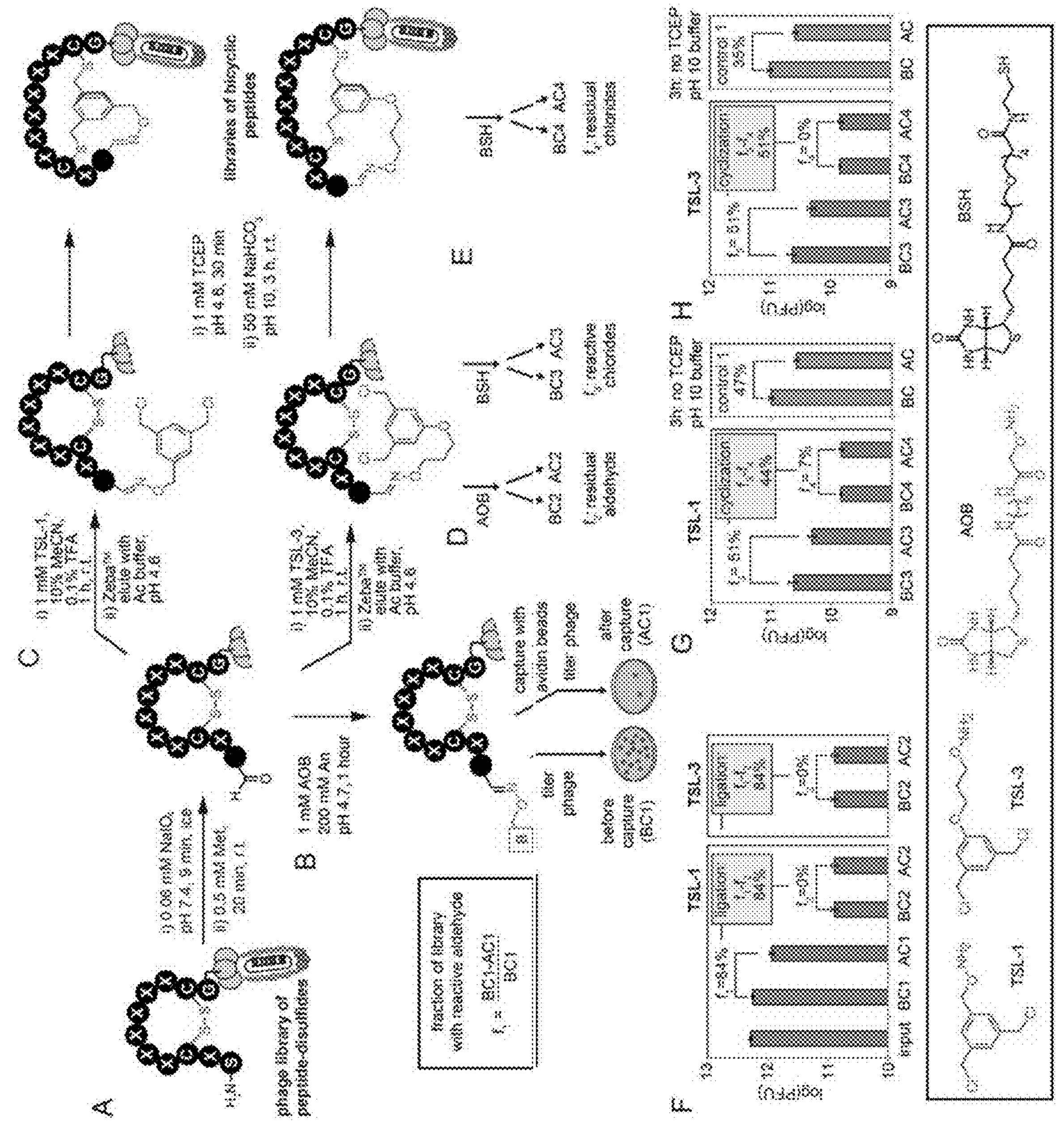

Phage displayed library of peptides with structure SxCxxxC, where S is serine, C is cysteine and x is a random amino acid, was used as starting point for production of genetically-encoded bicycle library. FIG. 12 describes example of modification of a clone from such phage library using a TSL6 linker. FIG. 13 and FIG. 14 describes example of modification of a large phage library SxCxxxxxxC using a TSL1, TSL3 or TSL6 linker and show a generality of this approach for any library and any linker geometry. We used conditions optimized for ligation on synthetic peptide sequence: specifically, library was exposed to ice-cold 60 micromolar solution of sodium periodate in PBS for 8 minutes, and the reaction was quenched by adding a 0.5 mM solution of methionine. Oxidized library was exposed to 1 mM solution of TSL6 linker in 0.1% aqueous trifluoroacetic acid for one hour at room temperature. The ligated library can be purified by size exclusion chromatography, such as Zeba™ Spin Desalting Columns, 7K MWCO using pH 4 buffer as eluent. Purified library was exposed to TCEP at pH 4 to reduce the disulfide bonds. Lastly, Tris buffered medium was added to the solution to raise the pH to 8 and promote bicyclization (FIG. 13A). Each step of the reaction can be effectively monitored using a range of capture reagents (FIG. 13B). For example to quantify the oxidation step, we mixed the oxidized library with aminooxybiotin (AOB) in aniline acetate buffer and measured the titer of phage before and after exposure to streptavidin-coated beads (FIG. 13C, F). AOB capture demonstrated that 73% of the library is oxidized. Only 10% of the phage population contained AOB-reactive aldehyde after exposure to TSL6, indicating that 87% of the oxidized library is ligated with TSL6. The same procedure can be used to test integrity of the reactive groups. For example, modification by AOB followed by capture demonstrated that aldehydes remain reactive when library was incubated in 0.1% TFA without TSL linker (FIG. 13F). Analogously, exposure to BIA and capture by streptavidin ("BIA capture") can be used to quantify the number of thiols and exposure to BSH followed by capture with streptavidin ("BSH capture") can be used to quantify the fraction of library that contains thiol-reactive benzyl chloride groups. Exposure to BIA (FIG. 13G) after ligation and after bicyclization (FIG. 13H) shows that thiols are present in the library after ligation but they disappear after bicyclization. Analogously, exposure to BSH can be used to check for presence and absence of benzyl chloride groups. Exposure to BSH can also be used to check the integrity of benzyl chloride groups. For example, prolonged exposure of ligated library to pH 7 or purification in pH 7 buffer leads to hydrolysis of benzyl chloride groups as determined by BSH-capture. This observation was used to select specific conditions for purification of library ligated to TSL6. It is not obvious how purification and integrity of the TSL7-modified library could be checked without such quantification. Optimization of other peptide sizes and linkers sizes follow the same steps (FIG. 11, FIG. 12) and show the same observations.

Figure 15A:
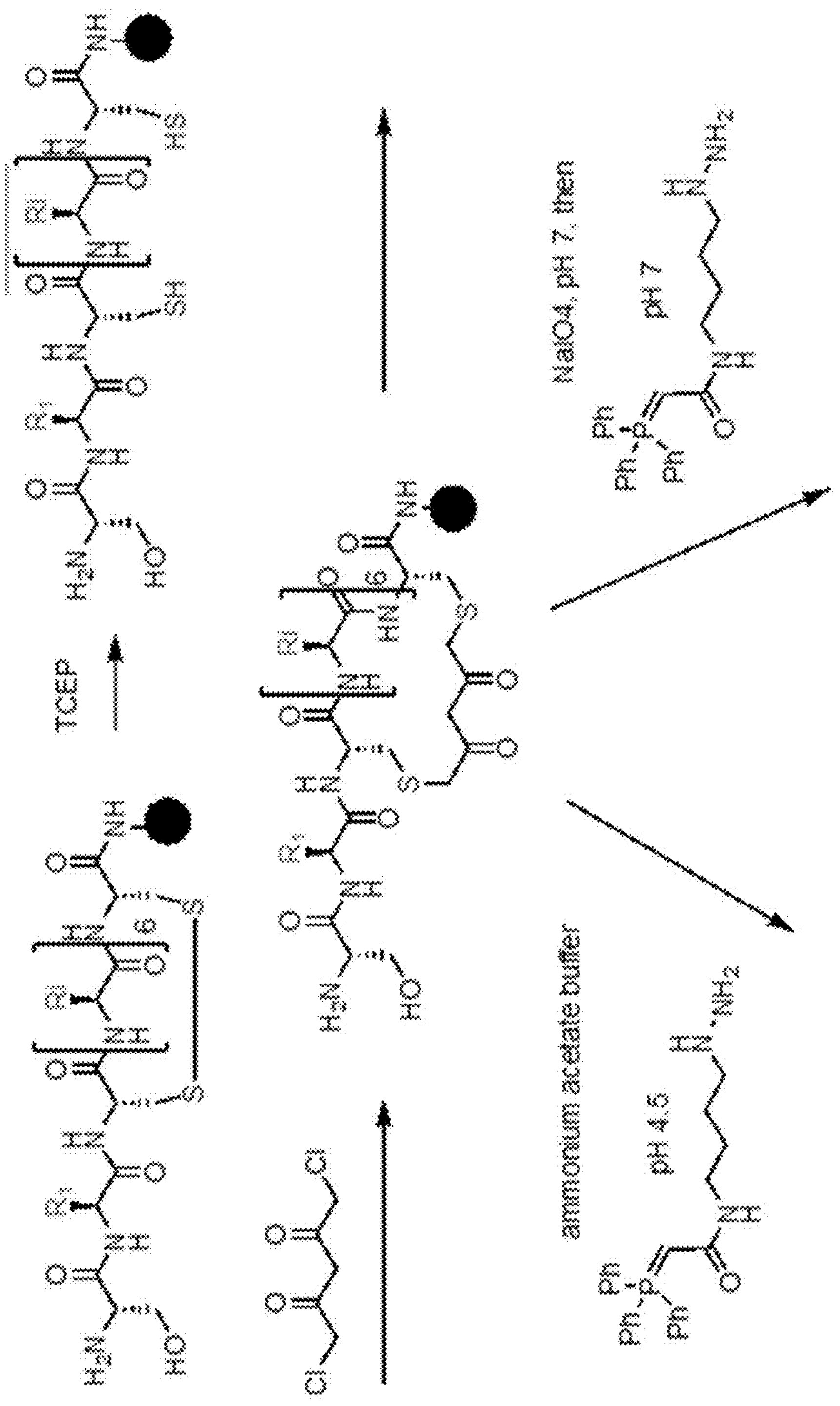
FIGS. 15A and 15B (continuation of 15A) shows an example of the bicyclization that employs the molecules that correspond to two halves of the linker introduced in two distinct locations in the peptide: first half by reaction with the peptide terminus and the second half introduced by reaction with two side chains of the peptide. The intermediate complex, which may have been purified, is induced to undergo cyclization be reaction of the two halves of the linker.
Figure 15B:
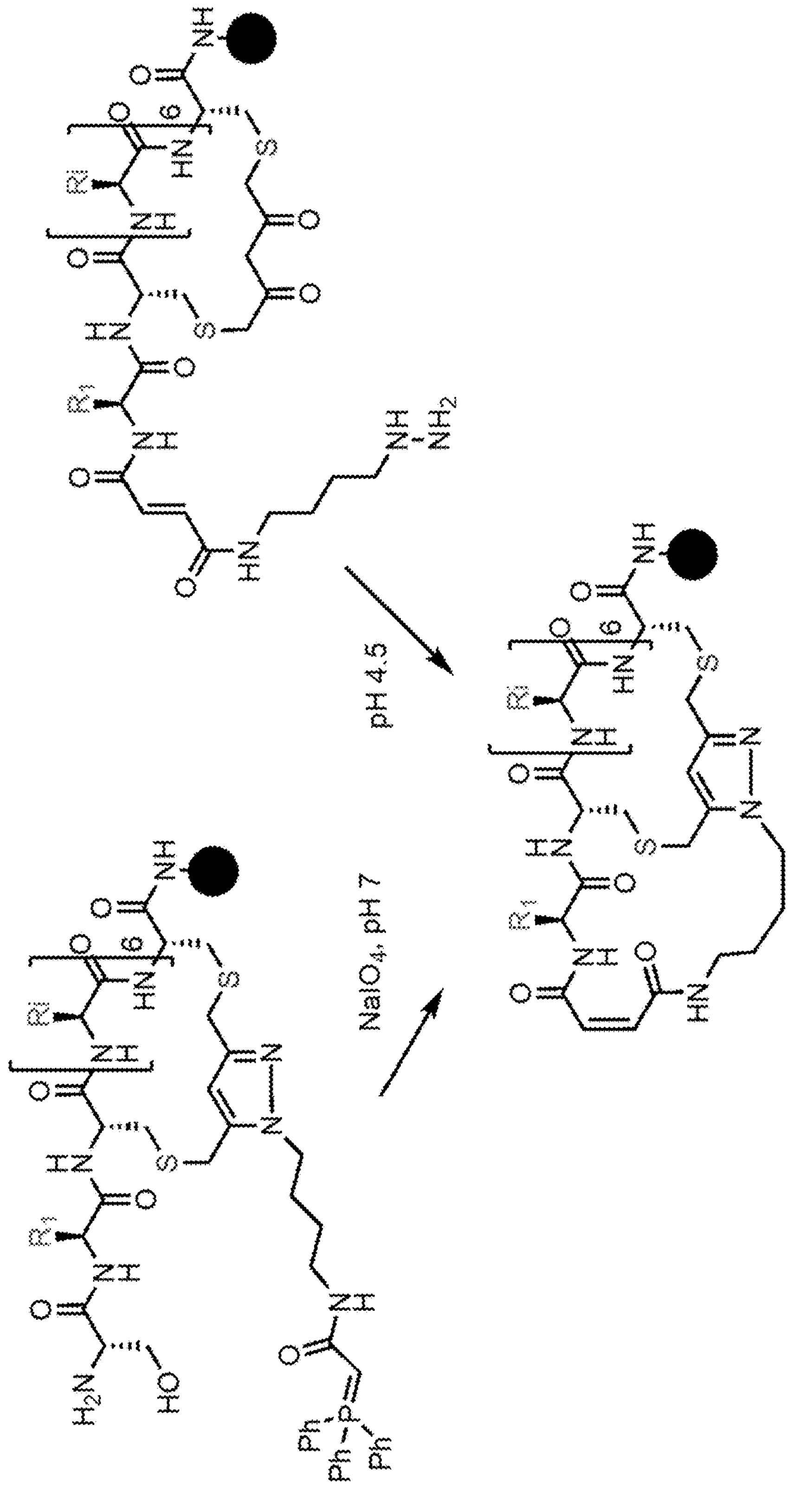

Example 7: Synthetic peptide or phage displayed peptide with two Cys residues in the sequences can be reacted with 1,5-dichloropentadione-2,4 at pH 8.5 to quantitatively introduce 1,3-diketone group into the peptide. In synthetic peptides, LCMS confirms the completion of the reaction in multiple diverse peptide sequences. In phage libraries displayed on phage, reaction of the 1,3-diketone modified product with hydrazine-biotin followed by capture with streptavidin beads confirms the presence of 1,3-diketone in the displayed peptide. The 1,3-diketone group in the peptides or phage displayed peptides can be then modified with alkyl or aryl hydrazines in controlled conditions such as ammonium acetate buffer pH 4.5 FIG. 15A. This reactivity can be used to introduce the functional group, such as aldehyde-reactive ylide that completes a reaction with N-terminus and a bicyclization in the subsequent step (FIG. 15B). For example, the said peptide containing 1,3-diketone group can be modified at the N-terminus to introduce the aldehyde, and change of the environment to acidic pH will induce bicyclization via an intramolecular reaction between hydrazine at the N-terminus and 1,3-diketone ligated to the side chains (FIG. 15B right pathway). In another example, the sequence of the reaction can be reversed where a linker that contains N-terminal reactive group is reacted with 1,3-diketone in acidic pH. Oxidation of the terminus at neutral pH triggers bicyclization via reaction with N-terminus (FIG. 15B left pathway).

Example 8: Production of genetically-encoded bicycle library by modification of the phage displayed libraries of peptides and selection of bicyclic peptides that bind to the target from this library. The screening steps were performed using a representative human protein Nodal: GenBank: BC104976.1; full sequence described in Proc. Natl. Acad. Sci. U.S.A., 2002, 99 (26), 16899-16903. Specifically, a 40-338 amino acid sequence PLAYMLSLY[ . . . ]VLLDHHKD as encoded by BC104976 of Hexahistidine-tagged Nodal (His-Nodal) catalog number ag21882 in Proteintech was used. Selection employed known techniques for selection of phage displayed libraries and can be readily performed for any other target. Results of the screening, panning and validation of TSL-6-modified SXCX6C is shown in FIG. 13.

Figure 16:
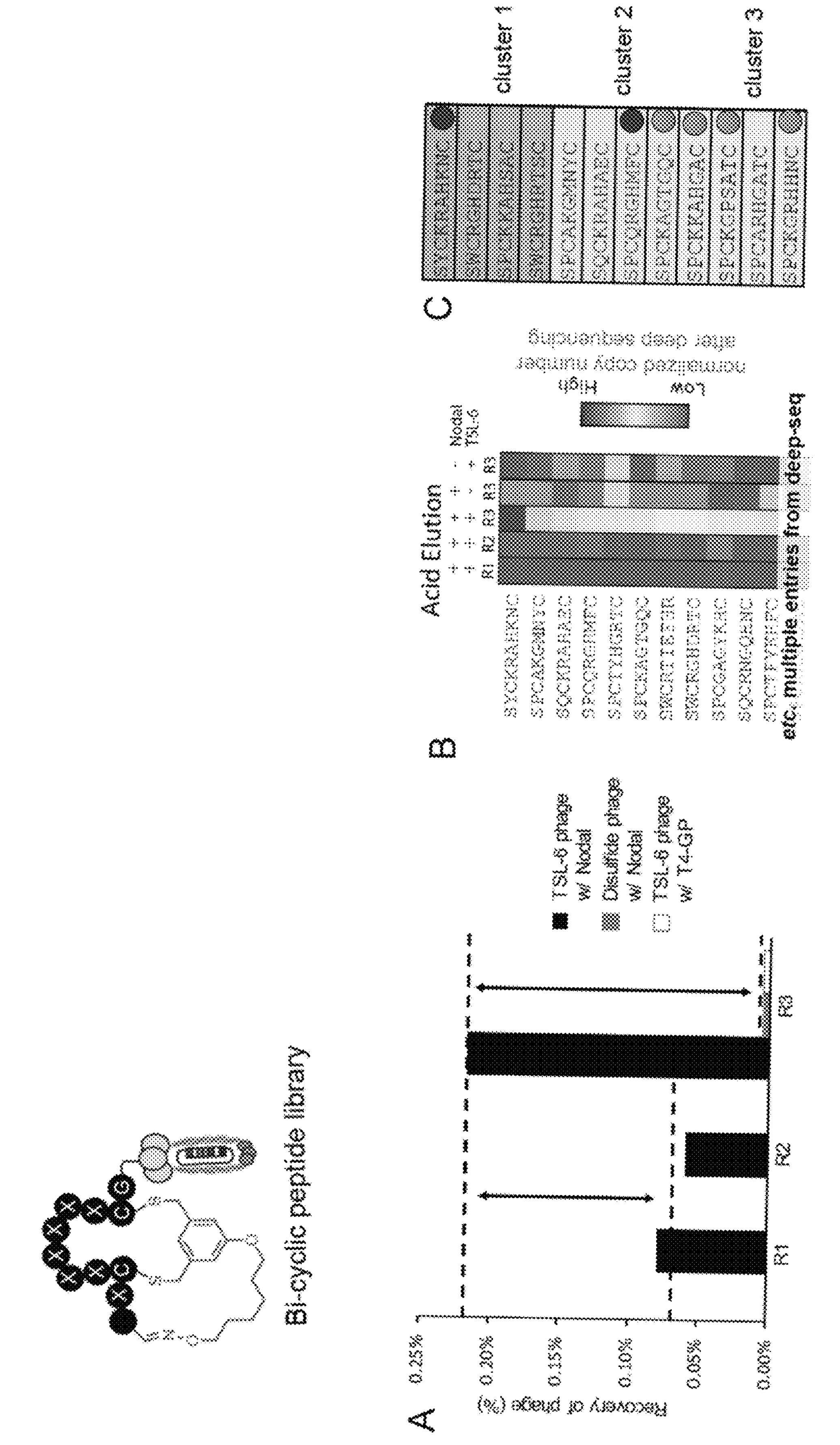
FIG. 16A shows the scaffold of the bicyclic peptide library.
FIG. 16B shows three panels A, B and C, showing production of genetically-encoded bicycle library by modification of the phage displayed libraries of peptides and selection of bicyclic peptides that bind to a target from this library.

Target immobilized on agarose beads functionalized with nitrilotriacetic acid (NTA) was panned using a mixed bicyclic library modified with TSL-6 (six-carbon) linker (FIG. 16B-A). After washing of beads on KingFisher Duo, the beads were boiled in water to release Nodal and bound ligands/phage were subjected to PCR and amplification. After three rounds of selection, a desired convergence was observed: bicycle library at round 3 (R3) was specifically enriched on Nodal immobilized on agarose beads when compared to R1 and R2 libraries. No enrichment was observed on blank beads or beads with control His-tagged target. Importantly, unmodified R3-library panned on Nodal-modified beads exhibited no enrichment, confirming that selected peptide sequences bind to Nodal only when constrained into a bicyclic scaffold (FIG. 16A). The dsDNA amplicons from each round of selection were sequenced using Illumina NextSeq and informatics analysis suggested that a large number of sequences (FIG. 16B) and at least three family of sequence motifs (FIG. 16C) are potential ligands for Nodal. A list of peptide sequences which bind to Nodal is shown in Table 1.

TABLE 1

| | | |
|---|---|---|
| 6. SYCKRAHKNC (SEQ ID NO. 4) | 39. SPCARHGATC (SEQ ID NO. 37) | 72. SPCVKGHGRC (SEQ ID NO. 70) |
| 7. SICRRAHQDC (SEQ ID NO. 5) | 40. SWCKGHTGAC (SEQ ID NO. 38) | 73. SPCHNNRHTC (SEQ ID NO. 71) |
| 8. SWCRGHDRTC (SEQ ID NO. 6) | 41. SPCKGRHHNC (SEQ ID NO. 39) | 74. SHCPWKSQHC (SEQ ID NO. 72) |
| 9. SHCKKGHGEC (SEQ ID NO. 7) | 42. SHCGTGIHRC (SEQ ID NO. 40) | 75. SPCGQKGHHC (SEQ ID NO. 73) |
| 10. SWCRGHRTSC (SEQ ID NO. 8) | 43. SHCGRIGNFC (SEQ ID NO. 41) | 76. SPCGKRGGAC (SEQ ID NO. 74) |
| 11. SPCKKAHSAC (SEQ ID NO. 9) | 44. SFCRKGHGFC (SEQ ID NO. 42) | 77. SPCPGSHKAC (SEQ ID NO. 75) |
| 12. SPCKKAHGAC (SEQ ID NO. 10) | 45. SPCTRHDATC (SEQ ID NO. 43) | 78. SPCHMGGAIC (SEQ ID NO. 76) |
| 13. SPCKGPSATC (SEQ ID NO. 11) | 46. SPCDNRHSTC (SEQ ID NO. 44) | 79. SHCVRGAKNC (SEQ ID NO. 77) |
| 14. SPCNRKGQVC (SEQ ID NO. 12) | 47. SPCANGHHAC (SEQ ID NO. 45) | 80. SPCERDGAKC (SEQ ID NO. 78) |
| 15. SHCQAHNGTC (SEQ ID NO. 13) | 48. SWCKGHGNQC (SEQ ID NO. 46) | 81. SPCRGNYHGC (SEQ ID NO. 79) |
| 16. SHCGRGVAAC (SEQ ID NO. 14) | 49. SPCKAGTGQC (SEQ ID NO. 47) | 82. SPCTEGSHYC (SEQ ID NO. 80) |
| 17. SPCSDSNKRC (SEQ ID NO. 15) | 50. SHCRHGQREC (SEQ ID NO. 48) | 83. SHCRITQHGC (SEQ ID NO. 81) |
| 18. SPCFQGVRGC (SEQ ID NO. 16) | 51. SQCRNGQHNC (SEQ ID NO. 49) | 84. SFCKGHKPYC (SEQ ID NO. 82) |
| 19. SPCNKGGSVC (SEQ ID NO. 17) | 52. SPCAHTGRSC (SEQ ID NO. 50) | 85. SSCKRAHLNC (SEQ ID NO. 83) |
| 20. SPCGFHTQEC (SEQ ID NO. 18) | 53. SPCHGIANVC (SEQ ID NO. 51) | 86. SPCSRHSKYC (SEQ ID NO. 84) |
| 21. SPCHQRGQLC (SEQ ID NO. 19) | 54. SHCRRAGANC (SEQ ID NO. 52) | 87. SHCQRQNKNC (SEQ ID NO. 85) |
| 22. SPCTSGHRQC (SEQ ID NO. 20) | 55. SPCPKGHPFC (SEQ ID NO. 53) | 88. SPCSWFDHHC (SEQ ID NO. 86) |
| 23. SPCVQGRGHC (SEQ ID NO. 21) | 56. SQCKRAHAEC (SEQ ID NO. 54) | 89. SPCSSRAHHC (SEQ ID NO. 87) |

TABLE 1-continued

| | | | | | |
|---|---|---|---|---|---|
| 24. | SPCVSGSRHC (SEQ ID NO. 22) | 57. | SPCHGHSGFC (SEQ ID NO. 55) | 90. | SPCQGNRHFC (SEQ ID NO. 88) |
| 25. | SPCRAHGKAC (SEQ ID NO. 23) | 58. | SPCRFGHHKC (SEQ ID NO. 56) | 91. | SPCIKGPKHC (SEQ ID NO. 89) |
| 26. | STCRKGQGIC (SEQ ID NO. 24) | 59. | SPCKEGRRFC (SEQ ID NO. 57) | 92. | SPCIHNDPQC (SEQ ID NO. 90) |
| 27. | SPCAHKLDHC (SEQ ID NO. 25) | 60. | SPCKQGKHHC (SEQ ID NO. 58) | 93. | SPCDKHSGYC (SEQ ID NO. 91) |
| 28. | SPCVSGHLVC (SEQ ID NO. 26) | 61. | SPCKWGGHHC (SEQ ID NO. 59) | 94. | SPCTMHGTAC (SEQ ID NO. 92) |
| 29. | SPCIHGHRQC (SEQ ID NO. 27) | 62. | SPCRVHGINC (SEQ ID NO. 60) | 95. | SPCFGTNHRC (SEQ ID NO. 93) |
| 30. | SPCIQGGRWC (SEQ ID NO. 28) | 63. | SPCDSRHGIC (SEQ ID NO. 61) | 96. | SPCNHQRGRC (SEQ ID NO. 94) |
| 31. | SHCRQHHGKC (SEQ ID NO. 29) | 64. | SPCRQGRHQC (SEQ ID NO. 62) | 97. | SHCAKKNAMC (SEQ ID NO. 95) |
| 32. | SPCKFAHQFC (SEQ ID NO. 30) | 65. | SPCALGMSHC (SEQ ID NO. 63) | 98. | SPCQRGNKSC (SEQ ID NO. 96) |
| 33. | SHCRDTRNTC (SEQ ID NO. 31) | 66. | SSCRRAHANC (SEQ ID NO. 64) | 99. | SHCPGGSKVC (SEQ ID NO. 97) |
| 34. | SPCHAGVSHC (SEQ ID NO. 32) | 67. | SPCHGFQHSC (SEQ ID NO. 65) | 100. | SPCNANGAWC (SEQ ID NO. 98) |
| 35. | SPCKGAHRMC (SEQ ID NO. 33) | 68. | SPCTHGAAYC (SEQ ID NO. 66) | 101. | SPCPANAKYC (SEQ ID NO. 99) |
| 36. | SPCSRGRGTC (SEQ ID NO. 34) | 69. | SHCQTARGVC (SEQ ID NO. 67) | 102. | SICRKAHYNC (SEQ ID NO. 100) |
| 37. | SPCKGNAQTC (SEQ ID NO. 35) | 70. | SPCSHLRNQC (SEQ ID NO. 68) | 103. | SHCPQDRKYC (SEQ ID NO. 101) |
| 38. | SPCKGAKTHC (SEQ ID NO. 36) | 71. | SPCKEGLLYC (SEQ ID NO. 69) | 104. | SQCPGETKQC (SEQ ID NO. 102) |

Figure 17:
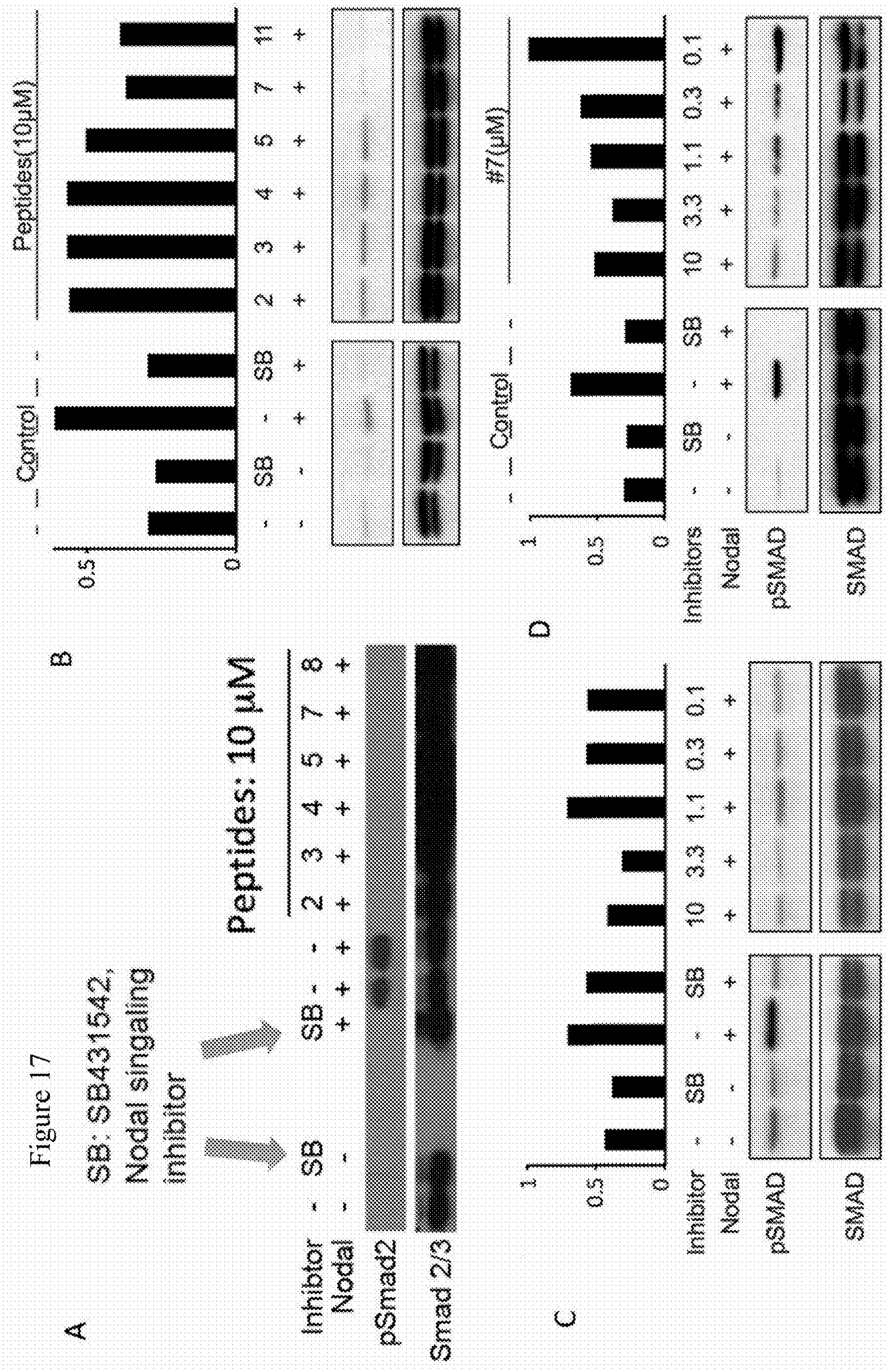
FIG. 17 shows 4 panels showing bicyclic structure ability to inhibit a known signaling event induced by Nodal.

To validate the binding ability of the predicted ligands, we tested the ability of the bicycles to inhibit a known signaling event induced by Nodal. Specifically, we employed Western blot with anti-phospho Smad antibody to detect Nodal-induced phosphorylation of effector protein Smad2 in embryonic carcinoma P19 cells. FIG. 17*a* describes that treatment of P19 cells with 100 ng/mL Nodal for 1 hour in Dulbecco's Modified Eagles Media (DMEM) supplemented with 2.5% fetal bovine serum (FBS)+7.5% bovine serum albumin (BSA) induces increase in pSmad2 intensity. Nodal-induced increase in pSmad is abrogated when P19 cells are incubated with 100 ng/mL Nodal and known kinase inhibitors SB-431542. Similarly, co-treatment with 100 ng/mL Nodal and 100 μM of bicyclic peptides 2 (SPCKAGTGQC (SEQ ID NO. 47)), 3 (SPCKGPSATC (SEQ ID NO. 11)), 4 (SPCKGRHHNC (SEQ ID NO. 39)), 5 (SPCKKAHGAC (SEQ ID NO. 10)), 7 (SPCQRGHMFC (SEQ ID NO. 103)) and 11 (SYCKRAHKNC (SEQ ID NO. 4)) does not increase pSmad2 phosphorylation above the background level. The bicyclic peptides serve as antagonists of Nodal at 100 micromolar concentration. FIG. 17*b* describes that from six bicyclic peptides only two retain potency at 10 μM concentration: bicycles 7 (SPCQRGHMFC (SEQ ID NO. 103)) and 11 (SYCKRAHKNC (SEQ ID NO. 4)) inhibit pSmad2 phosphorylation whereas bicycles 2, 3, 4, and 5 do not inhibit pSmad2 phosphorylation at 10 μM concentration. FIGS. 17*c-d* describe the dose-response of the bicycles 7 and 11 and suggest that half-inhibitory concentration for antagonism of Nodal signaling is between 1 and 3 μM.

SPCQRGHMFC (SEQ ID NO. 103)-TSL6 and SYCKRAHKNC (SEQ ID NO. 4)-TSL6 and derivative compounds have the ability to antagonize the signaling function of protein Nodal in carcinoma cells. Derivative compounds of SPCQRGHMFC (SEQ ID NO. 103)-TSL6 and SYCKRAHKNC (SEQ ID NO. 4)-TSL6 are those that retain similar structural features of these compounds and exhibit a similar or enhanced ability to antagonize the function of Nodal protein. The only known Nodal antagonist peptide is anti-human Nodal monoclonal antibody 3D1 (WO2016057683A2). Small-molecule compounds that can antagonize Nodal comprise SB431542 (noted as SB in FIG. 17) and derivatives thereof. But these compounds do not interact with Nodal and they are inhibitors of ALK5, ALK4 and ALK7 kinases acting downstream of Nodal.

REFERENCES

All publications, patents and patent applications mentioned in this specification are indicative of the level of skill of those skilled in the art to which this invention pertains and, if permitted, are herein incorporated by reference to the same extent as if each individual publication, patent, or patent applications was specifically and individually indicated to be incorporated by reference.

Gregory Paul Winter, Christian Heinis, Elise Bernard, David Loakes, Daniel Paul Teufel, U.S. Pat. No. 9,518,081B2 Peptide libraries Kale, S. S.; Villequey, C.; Kong, X.-D.; Zorzi, A.; Deyle, K.; Heinis, C., Cyclization of peptides with two chemical bridges affords large scaffold diversities. Nature Chemistry 2018, 10, 715-723

Liu, W. D.; Zheng, Y. W.; Kong, X. D.; Heinis, C.; Zhao, Y. B.; Wu, C. L., Precisely Regulated and Efficient Locking of Linear Peptides into Stable Multicyclic Topologies through a One-Pot Reaction. *Angew. Chem. Int. Ed.* 2017, 56, 4458-4463.

Sako, Y.; Morimoto, J.; Murakami, H.; Suga, H., Ribosomal Synthesis of Bicyclic Peptides via Two Orthogonal Inter-Side-Chain Reactions. *J. Am. Chem. Soc.* 2008, 130 (23), 7232-7234.

Hacker, D. E.; Hoinka, J.; Iqbal, E. S.; Przytycka, T. M.; Hartman, M. C., Highly Constrained Bicyclic Scaffolds for the Discovery of Protease-Stable Peptides via mRNA Display. *ACS Chem Biol* 2017, 12 (3), 795-804.

Heinis, C.; Rutherford, T.; Freund, S.; Winter, G., Phage-encoded combinatorial chemical libraries based on bicyclic peptides. *Nat. Chem. Biol.* 2009, 5, 502-507.

Chen, S.; Bertoldo, D.; Angelini, A.; Pojer, F.; Heinis, C., Peptide Ligands Stabilized by Small Molecules. *Angew. Chem. Int. Ed.* 2014, 53, 1602-1606

Diderich, P.; Bertoldo, D.; Dessen, P.; Khan, M. M.; Pizzitola, I.; Held, W.; Huelsken, J.; Heinis, C., Phage Selection of Chemically Stabilized α-Helical Peptide Ligands. *ACS Chem. Biol.* 2016, 11, 1422-1427

Bellotto, S.; Chen, S.; Rentero Rebollo, I.; Wegner, H. A.; Heinis, C., Phage Selection of Photoswitchable Peptide Ligands. *J. Am. Chem. Soc.* 2014, 136, 5880-5883.

Jafari, M. R.; Lakusta, J.; Lundgren, R. J.; Derda, R., Allene Functionalized Azobenzene Linker Enables Rapid and Light-Responsive Peptide Macrocyclization. *Bioconj. Chem.* 2016, 27, 509-514.

Kalhor-Monfared, S.; Jafari, M. R.; Patterson, J. T.; Kitov, P. I.; Dwyer, J. J.; Nuss, J. M.; Derda, R., Rapid biocompatible macrocyclization of peptides with decafluoro-diphenylsulfone. *Chem. Sci.* 2016, 7, 3785-3790

Ng, S.; Derda, R., Phage-displayed macrocyclic glycopeptide libraries. *Org. Biomol. Chem.* 2016, 14, 5539-5545.

Hacker, D. E.; Hoinka, J.; Iqbal, E. S.; Przytycka, T. M.; Hartman, M. C., Highly Constrained Bicyclic Scaffolds for the Discovery of Protease-Stable Peptides via mRNA Display. *ACS Chem Biol* 2017, 12 (3), 795-804.

Wang, G. Z.; Shang, R.; Cheng, W. M.; Fu, Y., Decarboxylative 1,4-Addition of alpha-Oxocarboxylic Acids with Michael Acceptors Enabled by Photoredox Catalysis. *Org. Lett.* 2015, 17 (19), 4830-3.

Bloom, S.; Liu, C.; Kolmel, D. K.; Qiao, J. X.; Zhang, Y.; Poss, M. A.; Ewing, W. R.; MacMillan, D. W. C., Decarboxylative alkylation for site-selective bioconjugation of native proteins via oxidation potentials. *Nat Chem* 2018, 10 (2), 205-211.

Laping, N. J.; Grygielko, E.; Mathur, A.; Butter, S.; Bomberger, J.; Tweed, C.; Martin, W.; Fornwald, J.; Lehr, R.; Harling, J.; Gaster, L.; Callahan, J. F.; Olson, B. A. Inhibition of transforming growth factor (TGF)-beta 1-induced extracellular matrix with a novel inhibitor of the TGF-beta type I receptor kinase activity: SB-431542. *Mol. Pharmacol.* 2002, 62, 58-64.

Lonardo, E.; Hermann, P. C.; Mueller, M. T.; Huber, S.; Balic, A.; Miranda-Lorenzo, I.; Zagorac, S.; Alcala, S.; Roderiguez-Arabaolaza, I.; Ramirez, J. C.; Torres-Ruiz, R.; Garcia, E.; Hidalgo, M.; Cebrian, D. A.; Heuchel, R.; Lohr, M.; Berger, F.; Bartenstein, P.; Aicher, A.; Heeschen, C. Nodal/Activin Signaling Drives Self-Renewal and Tumorigenicity of Pancreatic Cancer Stem Cells and Provides a Target for Combined Drug Therapy. *Cell Stem Cell* 2011, 9, 433-446.

Strizzi, L.; Sandomenico, A.; Margaryan, N. V.; Foca, A.; Sanguigno, L.; Bodenstine, T. M.; Chandler, G. S.; Reed, D. W.; Gilgur, A.; Seftor, E. A.; Seftor, R. E. B.; Khalkhali-Ellis, Z.; *Leonardi*, A.; Ruvo, M.; Hendrix, M. J. C. Effects of a novel Nodal-targeting monoclonal antibody in melanoma. *Oncotarget* 2015, 6, 34071-34086

Chen, J.; Liu, W. B.; Jia, W. D.; Xu, G. L.; Ma, J. L.; Ren, Y.; Chen, H.; Sun, S. N.; Huang, M.; Li, J. S. Embryonic Morphogen Nodal Is Associated with Progression and Poor Prognosis of Hepatocellular Carcinoma. *Plos One* 2014, 9 Proc. Natl. Acad. Sci. U.S.A., 2002, 99 (26), 16899-16903

The invention claimed is:

1. A genetically-encoded peptide construct comprising a bicyclic structure comprising a two-fold symmetric linker having a first end and a second end comprising two reactive groups attached to a genetically encoded polypeptide, wherein the first end is ligated to a terminus of the polypeptide by a covalent bond, and wherein both reactive groups of the linker second end are each ligated to side chain residues of the polypeptide by a covalent bond, wherein the linker comprises an aliphatic chain having between 1-6 carbon atoms, wherein the polypeptide consists of unprotected, natural proteogenic amino acids, and does not comprise a free N-terminus.

2. The construct of claim 1 wherein the linker further comprises an ester, a phenyl, or an amine group.

3. The construct of claim 1 wherein the polypeptide terminus is an N-terminus and the side chain residues are cysteine, lysine or tyrosine.

4. The construct of claim 1 wherein the linker reactive groups are electrophilic groups reactive to thiol, amine or phenol.

5. The construct of claim 1 wherein the linker first end comprises an aldehyde reactive group comprising an oxime, hydrazine, 2-amino benzamidoxime, phosphonium ylide, sulphur ylide, nitrogen ylide or any other carbon nucleophile and carbenoid reagent known to be reactive with aldehydes and stable in aqueous environment.

6. The construct of claim 1 wherein the polypeptide comprises two cysteine residues and an N-terminal serine or threonine residue, wherein the N-terminal serine or threonine is first converted to an aldehyde by selective oxidation and wherein the second end reactive groups are covalently bonded to the cysteine residues.

7. The construct of claim 1 which is attached to a carrier comprising a phage particle bearing the polypeptide externally and including a nucleic acid encoding the polypeptide.

8. The construct of claim 1 which is a RNA display compound, said RNA display bearing the polypeptide; and including an RNA sequence encoding the polypeptide, and linked to the polypeptide.

9. The construct of claim 1 which is a DNA display compound, said DNA display bearing the polypeptide; and including a DNA encoding the polypeptide, linked to the polypeptide.

10. The construct of claim 1 wherein the polypeptide terminus is a C-terminus and the side chain residues are cysteine or lysine, and wherein the linker first end comprises a reactive group with reactivity to C-terminus in acidic pH and the linker second end comprises two electrophilic groups that react specifically with thiol or amine residues.

11. The construct of claim 10 wherein the reactive group with reactivity to C-terminus in acidic pH is a C-terminal-selective photoredoxdecarboxylative conjugate addition.

12. The construct of claim 10 wherein the linker electrophilic groups are groups reactive with thiol in water comprising haloketone, haloacetamide, halobenzyl, a Michael acceptor comprising a conjugated C═C double bond including maleimides, actylates, carbonylacrylic reagents, 3-arylpropiolonitriles, allenamides fluoroarene, chlorotetrazines, Julia-Kocienški-like reagents, 2-azidoacrylates, organometallic palladium reagents, organo gold (I) reagents, conversion of thiols to dehydroalanines (Dha) followed by conjugate addition to Dha.

13. The construct of claim 10 wherein the linker electrophilic groups are groups reactive with amine in water comprising N-hydroxysuccinimide esters, aryl esters, perfluoroaryl esters, perfluoroarenes, ketenes, ortho-phthalaldehydes, or strain-release amine modifying agents.

14. The construct of claim 10 wherein the linker electrophilic groups are groups reactive with phenol in water comprising allylpaladium, diazodicarboxylate, diazonium salts, aniline-formaldehyde hemiaminal, rhodium carbenoids, dirhodium metallopeptide catalysts, Manganese-Catalyzed C—H Alkynylation, Waser's reagent, 1-[(triisopropylsilyl)ethynyl]-1,2-benziodoxol-3(1 H)-one (TIPS-EBX), under gold (I) catalysis, selective ruthenium-(II)-catalyzed C—H activation, palladium (II) acetate catalyzed C—H activation with aryl iodides in water.

15. The construct of claim 1 wherein the polypeptide comprises a terminal serine residue and two cysteine residues separated by at least 2, 3, 4 or 5 amino acid residues.

16. The construct of claim 2 wherein the linker comprises one of:

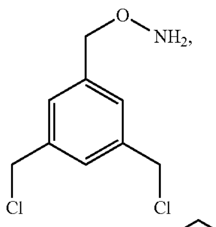

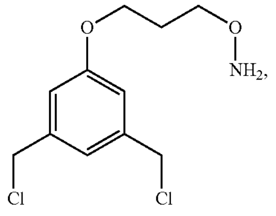

or

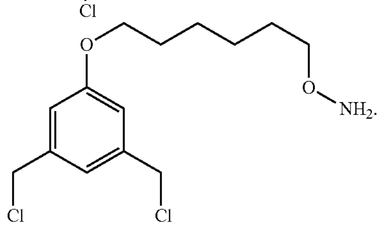

* * * * *

```
SEQUENCE LISTING

<160> NUMBER OF SEQ ID NOS: 107

<210> SEQ ID NO 1
<211> LENGTH: 8
<212> TYPE: PRT
<213> ORGANISM: Artificial Sequence
<220> FEATURE:
<223> OTHER INFORMATION: Synthesized

<400> SEQUENCE: 1

Ser Cys His Val Trp Trp Asp Cys
1               5


<210> SEQ ID NO 2
<211> LENGTH: 8
<212> TYPE: PRT
<213> ORGANISM: Artificial Sequence
<220> FEATURE:
<223> OTHER INFORMATION: Synthesized

<400> SEQUENCE: 2

Ser Val Cys Phe Asp Asn Gly Cys
1               5


<210> SEQ ID NO 3
<211> LENGTH: 11
<212> TYPE: PRT
<213> ORGANISM: Artificial Sequence
<220> FEATURE:
<223> OTHER INFORMATION: Synthesized

<400> SEQUENCE: 3

Ser Trp Asp Tyr Arg Glu Cys Tyr Leu Glu Cys
1               5                   10


<210> SEQ ID NO 4
```

-continued

```
<211> LENGTH: 10
<212> TYPE: PRT
<213> ORGANISM: Artificial Sequence
<220> FEATURE:
<223> OTHER INFORMATION: Synthesized

<400> SEQUENCE: 4

Ser Tyr Cys Lys Arg Ala His Lys Asn Cys
1               5                   10


<210> SEQ ID NO 5
<211> LENGTH: 10
<212> TYPE: PRT
<213> ORGANISM: Artificial Sequence
<220> FEATURE:
<223> OTHER INFORMATION: Synthesized

<400> SEQUENCE: 5

Ser Ile Cys Arg Arg Ala His Gln Asp Cys
1               5                   10


<210> SEQ ID NO 6
<211> LENGTH: 10
<212> TYPE: PRT
<213> ORGANISM: Artificial Sequence
<220> FEATURE:
<223> OTHER INFORMATION: Synthesized

<400> SEQUENCE: 6

Ser Trp Cys Arg Gly His Asp Arg Thr Cys
1               5                   10


<210> SEQ ID NO 7
<211> LENGTH: 10
<212> TYPE: PRT
<213> ORGANISM: Artificial Sequence
<220> FEATURE:
<223> OTHER INFORMATION: Synthesized

<400> SEQUENCE: 7

Ser His Cys Lys Lys Gly His Gly Glu Cys
1               5                   10


<210> SEQ ID NO 8
<211> LENGTH: 10
<212> TYPE: PRT
<213> ORGANISM: Artificial Sequence
<220> FEATURE:
<223> OTHER INFORMATION: Synthesized

<400> SEQUENCE: 8

Ser Trp Cys Arg Gly His Arg Thr Ser Cys
1               5                   10


<210> SEQ ID NO 9
<211> LENGTH: 10
<212> TYPE: PRT
<213> ORGANISM: Artificial Sequence
<220> FEATURE:
<223> OTHER INFORMATION: Synthesized

<400> SEQUENCE: 9

Ser Pro Cys Lys Lys Ala His Ser Ala Cys
1               5                   10


<210> SEQ ID NO 10
<211> LENGTH: 10
```

-continued

<212> TYPE: PRT
<213> ORGANISM: Artificial Sequence
<220> FEATURE:
<223> OTHER INFORMATION: Synthesized

<400> SEQUENCE: 10

Ser Pro Cys Lys Lys Ala His Gly Ala Cys
1 5 10

<210> SEQ ID NO 11
<211> LENGTH: 10
<212> TYPE: PRT
<213> ORGANISM: Artificial Sequence
<220> FEATURE:
<223> OTHER INFORMATION: Synthesized

<400> SEQUENCE: 11

Ser Pro Cys Lys Gly Pro Ser Ala Thr Cys
1 5 10

<210> SEQ ID NO 12
<211> LENGTH: 10
<212> TYPE: PRT
<213> ORGANISM: Artificial Sequence
<220> FEATURE:
<223> OTHER INFORMATION: Synthesized

<400> SEQUENCE: 12

Ser Pro Cys Asn Arg Lys Gly Gln Val Cys
1 5 10

<210> SEQ ID NO 13
<211> LENGTH: 10
<212> TYPE: PRT
<213> ORGANISM: Artificial Sequence
<220> FEATURE:
<223> OTHER INFORMATION: Synthesized

<400> SEQUENCE: 13

Ser His Cys Gln Ala His Asn Gly Thr Cys
1 5 10

<210> SEQ ID NO 14
<211> LENGTH: 10
<212> TYPE: PRT
<213> ORGANISM: Artificial Sequence
<220> FEATURE:
<223> OTHER INFORMATION: Synthesized

<400> SEQUENCE: 14

Ser His Cys Gly Arg Gly Val Ala Ala Cys
1 5 10

<210> SEQ ID NO 15
<211> LENGTH: 10
<212> TYPE: PRT
<213> ORGANISM: Artificial Sequence
<220> FEATURE:
<223> OTHER INFORMATION: Synthesized

<400> SEQUENCE: 15

Ser Pro Cys Ser Asp Ser Asn Lys Arg Cys
1 5 10

<210> SEQ ID NO 16
<211> LENGTH: 10
<212> TYPE: PRT

-continued

<213> ORGANISM: Artificial Sequence
<220> FEATURE:
<223> OTHER INFORMATION: Synthesized

<400> SEQUENCE: 16

Ser Pro Cys Phe Gln Gly Val Arg Gly Cys
1 5 10

<210> SEQ ID NO 17
<211> LENGTH: 10
<212> TYPE: PRT
<213> ORGANISM: Artificial Sequence
<220> FEATURE:
<223> OTHER INFORMATION: Synthesized

<400> SEQUENCE: 17

Ser Pro Cys Asn Lys Gly Gly Ser Val Cys
1 5 10

<210> SEQ ID NO 18
<211> LENGTH: 10
<212> TYPE: PRT
<213> ORGANISM: Artificial Sequence
<220> FEATURE:
<223> OTHER INFORMATION: Synthesized

<400> SEQUENCE: 18

Ser Pro Cys Gly Phe His Thr Gln Glu Cys
1 5 10

<210> SEQ ID NO 19
<211> LENGTH: 10
<212> TYPE: PRT
<213> ORGANISM: Artificial Sequence
<220> FEATURE:
<223> OTHER INFORMATION: Synthesized

<400> SEQUENCE: 19

Ser Pro Cys His Gln Arg Gly Gln Leu Cys
1 5 10

<210> SEQ ID NO 20
<211> LENGTH: 10
<212> TYPE: PRT
<213> ORGANISM: Artificial Sequence
<220> FEATURE:
<223> OTHER INFORMATION: Synthesized

<400> SEQUENCE: 20

Ser Pro Cys Thr Ser Gly His Arg Gln Cys
1 5 10

<210> SEQ ID NO 21
<211> LENGTH: 10
<212> TYPE: PRT
<213> ORGANISM: Artificial Sequence
<220> FEATURE:
<223> OTHER INFORMATION: Synthesized

<400> SEQUENCE: 21

Ser Pro Cys Val Gln Gly Arg Gly His Cys
1 5 10

<210> SEQ ID NO 22
<211> LENGTH: 10
<212> TYPE: PRT
<213> ORGANISM: Artificial Sequence
<220> FEATURE:
<223> OTHER INFORMATION: Synthesized

<400> SEQUENCE: 22

Ser Pro Cys Val Ser Gly Ser Arg His Cys
1 5 10

<210> SEQ ID NO 23
<211> LENGTH: 10
<212> TYPE: PRT
<213> ORGANISM: Artificial Sequence
<220> FEATURE:
<223> OTHER INFORMATION: Synthesized

<400> SEQUENCE: 23

Ser Pro Cys Arg Ala His Gly Lys Ala Cys
1 5 10

<210> SEQ ID NO 24
<211> LENGTH: 10
<212> TYPE: PRT
<213> ORGANISM: Artificial Sequence
<220> FEATURE:
<223> OTHER INFORMATION: Synthesized

<400> SEQUENCE: 24

Ser Thr Cys Arg Lys Gly Gln Gly Ile Cys
1 5 10

<210> SEQ ID NO 25
<211> LENGTH: 10
<212> TYPE: PRT
<213> ORGANISM: Artificial Sequence
<220> FEATURE:
<223> OTHER INFORMATION: Synthesized

<400> SEQUENCE: 25

Ser Pro Cys Ala His Lys Leu Asp His Cys
1 5 10

<210> SEQ ID NO 26
<211> LENGTH: 10
<212> TYPE: PRT
<213> ORGANISM: Artificial Sequence
<220> FEATURE:
<223> OTHER INFORMATION: Synthesized

<400> SEQUENCE: 26

Ser Pro Cys Val Ser Gly His Leu Val Cys
1 5 10

<210> SEQ ID NO 27
<211> LENGTH: 10
<212> TYPE: PRT
<213> ORGANISM: Artificial Sequence
<220> FEATURE:
<223> OTHER INFORMATION: Synthesized

<400> SEQUENCE: 27

Ser Pro Cys Ile His Gly His Arg Gln Cys
1 5 10

<210> SEQ ID NO 28
<211> LENGTH: 10
<212> TYPE: PRT
<213> ORGANISM: Artificial Sequence
<220> FEATURE:

-continued

<223> OTHER INFORMATION: Synthesized

<400> SEQUENCE: 28

```
Ser Pro Cys Ile Gln Gly Gly Arg Trp Cys
1               5                   10
```

<210> SEQ ID NO 29
<211> LENGTH: 10
<212> TYPE: PRT
<213> ORGANISM: Artificial Sequence
<220> FEATURE:
<223> OTHER INFORMATION: Synthesized

<400> SEQUENCE: 29

```
Ser His Cys Arg Gln His His Gly Lys Cys
1               5                   10
```

<210> SEQ ID NO 30
<211> LENGTH: 10
<212> TYPE: PRT
<213> ORGANISM: Artificial Sequence
<220> FEATURE:
<223> OTHER INFORMATION: Synthesized

<400> SEQUENCE: 30

```
Ser Pro Cys Lys Phe Ala His Gln Phe Cys
1               5                   10
```

<210> SEQ ID NO 31
<211> LENGTH: 10
<212> TYPE: PRT
<213> ORGANISM: Artificial Sequence
<220> FEATURE:
<223> OTHER INFORMATION: Synthesized

<400> SEQUENCE: 31

```
Ser His Cys Arg Asp Thr Arg Asn Thr Cys
1               5                   10
```

<210> SEQ ID NO 32
<211> LENGTH: 10
<212> TYPE: PRT
<213> ORGANISM: Artificial Sequence
<220> FEATURE:
<223> OTHER INFORMATION: Synthesized

<400> SEQUENCE: 32

```
Ser Pro Cys His Ala Gly Val Ser His Cys
1               5                   10
```

<210> SEQ ID NO 33
<211> LENGTH: 10
<212> TYPE: PRT
<213> ORGANISM: Artificial Sequence
<220> FEATURE:
<223> OTHER INFORMATION: Synthesized

<400> SEQUENCE: 33

```
Ser Pro Cys Lys Gly Ala His Arg Met Cys
1               5                   10
```

<210> SEQ ID NO 34
<211> LENGTH: 10
<212> TYPE: PRT
<213> ORGANISM: Artificial Sequence
<220> FEATURE:
<223> OTHER INFORMATION: Synthesized -continued

<400> SEQUENCE: 34

Ser Pro Cys Ser Arg Gly Arg Gly Thr Cys
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Synthesized

<400> SEQUENCE: 35

Ser Pro Cys Lys Gly Asn Ala Gln Thr Cys
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Synthesized

<400> SEQUENCE: 36

Ser Pro Cys Lys Gly Ala Lys Thr His Cys
1               5                   10

<210> SEQ ID NO 37
<211> LENGTH: 10
<212> TYPE: PRT
<213> ORGANISM: Artificial Sequence
<220> FEATURE:
<223> OTHER INFORMATION: Synthesized

<400> SEQUENCE: 37

Ser Pro Cys Ala Arg His Gly Ala Thr Cys
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthesized

<400> SEQUENCE: 38

Ser Trp Cys Lys Gly His Thr Gly Ala Cys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthesized

<400> SEQUENCE: 39

Ser Pro Cys Lys Gly Arg His His Asn Cys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthesized

<400> SEQUENCE: 40

Ser His Cys Gly Thr Gly Ile His Arg Cys
1 5 10

<210> SEQ ID NO 41
<211> LENGTH: 10
<212> TYPE: PRT
<213> ORGANISM: Artificial Sequence
<220> FEATURE:
<223> OTHER INFORMATION: Synthesized

<400> SEQUENCE: 41

Ser His Cys Gly Arg Ile Gly Asn Phe Cys
1 5 10

<210> SEQ ID NO 42
<211> LENGTH: 10
<212> TYPE: PRT
<213> ORGANISM: Artificial Sequence
<220> FEATURE:
<223> OTHER INFORMATION: Synthesized

<400> SEQUENCE: 42

Ser Phe Cys Arg Lys Gly His Gly Phe Cys
1 5 10

<210> SEQ ID NO 43
<211> LENGTH: 10
<212> TYPE: PRT
<213> ORGANISM: Artificial Sequence
<220> FEATURE:
<223> OTHER INFORMATION: Synthesized

<400> SEQUENCE: 43

Ser Pro Cys Thr Arg His Asp Ala Thr Cys
1 5 10

<210> SEQ ID NO 44
<211> LENGTH: 10
<212> TYPE: PRT
<213> ORGANISM: Artificial Sequence
<220> FEATURE:
<223> OTHER INFORMATION: Synthesized

<400> SEQUENCE: 44

Ser Pro Cys Asp Asn Arg His Ser Thr Cys
1 5 10

<210> SEQ ID NO 45
<211> LENGTH: 10
<212> TYPE: PRT
<213> ORGANISM: Artificial Sequence
<220> FEATURE:
<223> OTHER INFORMATION: Synthesized

<400> SEQUENCE: 45

Ser Pro Cys Ala Asn Gly His His Ala Cys
1 5 10

<210> SEQ ID NO 46
<211> LENGTH: 10
<212> TYPE: PRT
<213> ORGANISM: Artificial Sequence
<220> FEATURE:
<223> OTHER INFORMATION: Synthesized

<400> SEQUENCE: 46

Ser Trp Cys Lys Gly His Gly Asn Gln Cys
1 5 10

<210> SEQ ID NO 47
<211> LENGTH: 10
<212> TYPE: PRT
<213> ORGANISM: Artificial Sequence
<220> FEATURE:
<223> OTHER INFORMATION: Synthesized

<400> SEQUENCE: 47

Ser Pro Cys Lys Ala Gly Thr Gly Gln Cys
1 5 10

<210> SEQ ID NO 48
<211> LENGTH: 10
<212> TYPE: PRT
<213> ORGANISM: Artificial Sequence
<220> FEATURE:
<223> OTHER INFORMATION: Synthesized

<400> SEQUENCE: 48

Ser His Cys Arg His Gly Gln Arg Glu Cys
1 5 10

<210> SEQ ID NO 49
<211> LENGTH: 10
<212> TYPE: PRT
<213> ORGANISM: Artificial Sequence
<220> FEATURE:
<223> OTHER INFORMATION: Synthesized

<400> SEQUENCE: 49

Ser Gln Cys Arg Asn Gly Gln His Asn Cys
1 5 10

<210> SEQ ID NO 50
<211> LENGTH: 10
<212> TYPE: PRT
<213> ORGANISM: Artificial Sequence
<220> FEATURE:
<223> OTHER INFORMATION: Synthesized

<400> SEQUENCE: 50

Ser Pro Cys Ala His Thr Gly Arg Ser Cys
1 5 10

<210> SEQ ID NO 51
<211> LENGTH: 10
<212> TYPE: PRT
<213> ORGANISM: Artificial Sequence
<220> FEATURE:
<223> OTHER INFORMATION: Synthesized

<400> SEQUENCE: 51

Ser Pro Cys His Gly Ile Ala Asn Val Cys
1 5 10

<210> SEQ ID NO 52
<211> LENGTH: 10
<212> TYPE: PRT
<213> ORGANISM: Artificial Sequence
<220> FEATURE:
<223> OTHER INFORMATION: Synthesized

<400> SEQUENCE: 52

-continued

```
Ser His Cys Arg Arg Ala Gly Ala Asn Cys
1               5                   10


<210> SEQ ID NO 53
<211> LENGTH: 10
<212> TYPE: PRT
<213> ORGANISM: Artificial Sequence
<220> FEATURE:
<223> OTHER INFORMATION: Synthesized

<400> SEQUENCE: 53

Ser Pro Cys Pro Lys Gly His Pro Phe Cys
1               5                   10


<210> SEQ ID NO 54
<211> LENGTH: 10
<212> TYPE: PRT
<213> ORGANISM: Artificial Sequence
<220> FEATURE:
<223> OTHER INFORMATION: Synthesized

<400> SEQUENCE: 54

Ser Gln Cys Lys Arg Ala His Ala Glu Cys
1               5                   10


<210> SEQ ID NO 55
<211> LENGTH: 10
<212> TYPE: PRT
<213> ORGANISM: Artificial Sequence
<220> FEATURE:
<223> OTHER INFORMATION: Synthesized

<400> SEQUENCE: 55

Ser Pro Cys His Gly His Ser Gly Phe Cys
1               5                   10


<210> SEQ ID NO 56
<211> LENGTH: 10
<212> TYPE: PRT
<213> ORGANISM: Artificial Sequence
<220> FEATURE:
<223> OTHER INFORMATION: Synthesized

<400> SEQUENCE: 56

Ser Pro Cys Arg Phe Gly His His Lys Cys
1               5                   10


<210> SEQ ID NO 57
<211> LENGTH: 10
<212> TYPE: PRT
<213> ORGANISM: Artificial Sequence
<220> FEATURE:
<223> OTHER INFORMATION: Synthesized

<400> SEQUENCE: 57

Ser Pro Cys Lys Glu Gly Arg Arg Phe Cys
1               5                   10


<210> SEQ ID NO 58
<211> LENGTH: 10
<212> TYPE: PRT
<213> ORGANISM: Artificial Sequence
<220> FEATURE:
<223> OTHER INFORMATION: Synthesized

<400> SEQUENCE: 58

Ser Pro Cys Lys Gln Gly Lys His His Cys
```

```
1               5                   10


<210> SEQ ID NO 59
<211> LENGTH: 10
<212> TYPE: PRT
<213> ORGANISM: Artificial Sequence
<220> FEATURE:
<223> OTHER INFORMATION: Synthesized

<400> SEQUENCE: 59

Ser Pro Cys Lys Trp Gly Gly His His Cys
1               5                   10


<210> SEQ ID NO 60
<211> LENGTH: 10
<212> TYPE: PRT
<213> ORGANISM: Artificial Sequence
<220> FEATURE:
<223> OTHER INFORMATION: Synthesized

<400> SEQUENCE: 60

Ser Pro Cys Arg Val His Gly Ile Asn Cys
1               5                   10


<210> SEQ ID NO 61
<211> LENGTH: 10
<212> TYPE: PRT
<213> ORGANISM: Artificial Sequence
<220> FEATURE:
<223> OTHER INFORMATION: Synthesized

<400> SEQUENCE: 61

Ser Pro Cys Asp Ser Arg His Gly Ile Cys
1               5                   10


<210> SEQ ID NO 62
<211> LENGTH: 10
<212> TYPE: PRT
<213> ORGANISM: Artificial Sequence
<220> FEATURE:
<223> OTHER INFORMATION: Synthesized

<400> SEQUENCE: 62

Ser Pro Cys Arg Gln Gly Arg His Gln Cys
1               5                   10


<210> SEQ ID NO 63
<211> LENGTH: 10
<212> TYPE: PRT
<213> ORGANISM: Artificial Sequence
<220> FEATURE:
<223> OTHER INFORMATION: Synthesized

<400> SEQUENCE: 63

Ser Pro Cys Ala Leu Gly Met Ser His Cys
1               5                   10


<210> SEQ ID NO 64
<211> LENGTH: 10
<212> TYPE: PRT
<213> ORGANISM: Artificial Sequence
<220> FEATURE:
<223> OTHER INFORMATION: Synthesized

<400> SEQUENCE: 64

Ser Ser Cys Arg Arg Ala His Ala Asn Cys
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: Synthesized

<400> SEQUENCE: 65

Ser Pro Cys His Gly Phe Gln His Ser Cys
1 5 10

<210> SEQ ID NO 66
<211> LENGTH: 10
<212> TYPE: PRT
<213> ORGANISM: Artificial Sequence
<220> FEATURE:
<223> OTHER INFORMATION: Synthesized

<400> SEQUENCE: 66

Ser Pro Cys Thr His Gly Ala Ala Tyr Cys
1 5 10

<210> SEQ ID NO 67
<211> LENGTH: 10
<212> TYPE: PRT
<213> ORGANISM: Artificial Sequence
<220> FEATURE:
<223> OTHER INFORMATION: Synthesized

<400> SEQUENCE: 67

Ser His Cys Gln Thr Ala Arg Gly Val Cys
1 5 10

<210> SEQ ID NO 68
<211> LENGTH: 10
<212> TYPE: PRT
<213> ORGANISM: Artificial Sequence
<220> FEATURE:
<223> OTHER INFORMATION: Synthesized

<400> SEQUENCE: 68

Ser Pro Cys Ser His Leu Arg Asn Gln Cys
1 5 10

<210> SEQ ID NO 69
<211> LENGTH: 10
<212> TYPE: PRT
<213> ORGANISM: Artificial Sequence
<220> FEATURE:
<223> OTHER INFORMATION: Synthesized

<400> SEQUENCE: 69

Ser Pro Cys Lys Glu Gly Leu Leu Tyr Cys
1 5 10

<210> SEQ ID NO 70
<211> LENGTH: 10
<212> TYPE: PRT
<213> ORGANISM: Artificial Sequence
<220> FEATURE:
<223> OTHER INFORMATION: Synthesized

<400> SEQUENCE: 70

Ser Pro Cys Val Lys Gly His Gly Arg Cys
1 5 10

<210> SEQ ID NO 71
<211> LENGTH: 10
<212> TYPE: PRT
<213> ORGANISM: Artificial Sequence
<220> FEATURE:
<223> OTHER INFORMATION: Synthesized

<400> SEQUENCE: 71

Ser Pro Cys His Asn Asn Arg His Thr Cys
1 5 10

<210> SEQ ID NO 72
<211> LENGTH: 10
<212> TYPE: PRT
<213> ORGANISM: Artificial Sequence
<220> FEATURE:
<223> OTHER INFORMATION: Synthesized

<400> SEQUENCE: 72

Ser His Cys Pro Trp Lys Ser Gln His Cys
1 5 10

<210> SEQ ID NO 73
<211> LENGTH: 10
<212> TYPE: PRT
<213> ORGANISM: Artificial Sequence
<220> FEATURE:
<223> OTHER INFORMATION: Synthesized

<400> SEQUENCE: 73

Ser Pro Cys Gly Gln Lys Gly His His Cys
1 5 10

<210> SEQ ID NO 74
<211> LENGTH: 10
<212> TYPE: PRT
<213> ORGANISM: Artificial Sequence
<220> FEATURE:
<223> OTHER INFORMATION: Synthesized

<400> SEQUENCE: 74

Ser Pro Cys Gly Lys Arg Gly Gly Ala Cys
1 5 10

<210> SEQ ID NO 75
<211> LENGTH: 10
<212> TYPE: PRT
<213> ORGANISM: Artificial Sequence
<220> FEATURE:
<223> OTHER INFORMATION: Synthesized

<400> SEQUENCE: 75

Ser Pro Cys Pro Gly Ser His Lys Ala Cys
1 5 10

<210> SEQ ID NO 76
<211> LENGTH: 10
<212> TYPE: PRT
<213> ORGANISM: Artificial Sequence
<220> FEATURE:
<223> OTHER INFORMATION: Synthesized

<400> SEQUENCE: 76

Ser Pro Cys His Met Gly Gly Ala Ile Cys
1 5 10

<210> SEQ ID NO 77
<211> LENGTH: 10
<212> TYPE: PRT
<213> ORGANISM: Artificial Sequence
<220> FEATURE:
<223> OTHER INFORMATION: Synthesized

<400> SEQUENCE: 77

Ser His Cys Val Arg Gly Ala Lys Asn Cys
1 5 10

<210> SEQ ID NO 78
<211> LENGTH: 10
<212> TYPE: PRT
<213> ORGANISM: Artificial Sequence
<220> FEATURE:
<223> OTHER INFORMATION: Synthesized

<400> SEQUENCE: 78

Ser Pro Cys Glu Arg Asp Gly Ala Lys Cys
1 5 10

<210> SEQ ID NO 79
<211> LENGTH: 10
<212> TYPE: PRT
<213> ORGANISM: Artificial Sequence
<220> FEATURE:
<223> OTHER INFORMATION: Synthesized

<400> SEQUENCE: 79

Ser Pro Cys Arg Gly Asn Tyr His Gly Cys
1 5 10

<210> SEQ ID NO 80
<211> LENGTH: 10
<212> TYPE: PRT
<213> ORGANISM: Artificial Sequence
<220> FEATURE:
<223> OTHER INFORMATION: Synthesized

<400> SEQUENCE: 80

Ser Pro Cys Thr Glu Gly Ser His Tyr Cys
1 5 10

<210> SEQ ID NO 81
<211> LENGTH: 10
<212> TYPE: PRT
<213> ORGANISM: Artificial Sequence
<220> FEATURE:
<223> OTHER INFORMATION: Synthesized

<400> SEQUENCE: 81

Ser His Cys Arg Ile Thr Gln His Gly Cys
1 5 10

<210> SEQ ID NO 82
<211> LENGTH: 10
<212> TYPE: PRT
<213> ORGANISM: Artificial Sequence
<220> FEATURE:
<223> OTHER INFORMATION: Synthesized

<400> SEQUENCE: 82

Ser Phe Cys Lys Gly His Lys Pro Tyr Cys
1 5 10

<210> SEQ ID NO 83

<211> LENGTH: 10
<212> TYPE: PRT
<213> ORGANISM: Artificial Sequence
<220> FEATURE:
<223> OTHER INFORMATION: Synthesized

<400> SEQUENCE: 83

Ser Ser Cys Lys Arg Ala His Leu Asn Cys
1 5 10

<210> SEQ ID NO 84
<211> LENGTH: 10
<212> TYPE: PRT
<213> ORGANISM: Artificial Sequence
<220> FEATURE:
<223> OTHER INFORMATION: Synthesized

<400> SEQUENCE: 84

Ser Pro Cys Ser Arg His Ser Lys Tyr Cys
1 5 10

<210> SEQ ID NO 85
<211> LENGTH: 10
<212> TYPE: PRT
<213> ORGANISM: Artificial Sequence
<220> FEATURE:
<223> OTHER INFORMATION: Synthesized

<400> SEQUENCE: 85

Ser His Cys Gln Arg Gln Asn Lys Asn Cys
1 5 10

<210> SEQ ID NO 86
<211> LENGTH: 10
<212> TYPE: PRT
<213> ORGANISM: Artificial Sequence
<220> FEATURE:
<223> OTHER INFORMATION: Synthesized

<400> SEQUENCE: 86

Ser Pro Cys Ser Trp Phe Asp His His Cys
1 5 10

<210> SEQ ID NO 87
<211> LENGTH: 10
<212> TYPE: PRT
<213> ORGANISM: Artificial Sequence
<220> FEATURE:
<223> OTHER INFORMATION: Synthesized

<400> SEQUENCE: 87

Ser Pro Cys Ser Ser Arg Ala His His Cys
1 5 10

<210> SEQ ID NO 88
<211> LENGTH: 10
<212> TYPE: PRT
<213> ORGANISM: Artificial Sequence
<220> FEATURE:
<223> OTHER INFORMATION: Synthesized

<400> SEQUENCE: 88

Ser Pro Cys Gln Gly Asn Arg His Phe Cys
1 5 10

<210> SEQ ID NO 89
<211> LENGTH: 10

<212> TYPE: PRT
<213> ORGANISM: Artificial Sequence
<220> FEATURE:
<223> OTHER INFORMATION: Synthesized

<400> SEQUENCE: 89

Ser Pro Cys Ile Lys Gly Pro Lys His Cys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthesized

<400> SEQUENCE: 90

Ser Pro Cys Ile His Asn Asp Pro Gln Cys
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthesized

<400> SEQUENCE: 91

Ser Pro Cys Asp Lys His Ser Gly Tyr Cys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthesized

<400> SEQUENCE: 92

Ser Pro Cys Thr Met His Gly Thr Ala Cys
1               5                   10

<210> SEQ ID NO 93
<211> LENGTH: 10
<212> TYPE: PRT
<213> ORGANISM: Artificial Sequence
<220> FEATURE:
<223> OTHER INFORMATION: Synthesized

<400> SEQUENCE: 93

Ser Pro Cys Phe Gly Thr Asn His Arg Cys
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthesized

<400> SEQUENCE: 94

Ser Pro Cys Asn His Gln Arg Gly Arg Cys
1               5                   10

<210> SEQ ID NO 95
<211> LENGTH: 10
<212> TYPE: PRT

-continued

<213> ORGANISM: Artificial Sequence
<220> FEATURE:
<223> OTHER INFORMATION: Synthesized

<400> SEQUENCE: 95

Ser His Cys Ala Lys Lys Asn Ala Met Cys
1 5 10

<210> SEQ ID NO 96
<211> LENGTH: 10
<212> TYPE: PRT
<213> ORGANISM: Artificial Sequence
<220> FEATURE:
<223> OTHER INFORMATION: Synthesized

<400> SEQUENCE: 96

Ser Pro Cys Gln Arg Gly Asn Lys Ser Cys
1 5 10

<210> SEQ ID NO 97
<211> LENGTH: 10
<212> TYPE: PRT
<213> ORGANISM: Artificial Sequence
<220> FEATURE:
<223> OTHER INFORMATION: Synthesized

<400> SEQUENCE: 97

Ser His Cys Pro Gly Gly Ser Lys Val Cys
1 5 10

<210> SEQ ID NO 98
<211> LENGTH: 10
<212> TYPE: PRT
<213> ORGANISM: Artificial Sequence
<220> FEATURE:
<223> OTHER INFORMATION: Synthesized

<400> SEQUENCE: 98

Ser Pro Cys Asn Ala Asn Gly Ala Trp Cys
1 5 10

<210> SEQ ID NO 99
<211> LENGTH: 10
<212> TYPE: PRT
<213> ORGANISM: Artificial Sequence
<220> FEATURE:
<223> OTHER INFORMATION: Synthesized

<400> SEQUENCE: 99

Ser Pro Cys Pro Ala Asn Ala Lys Tyr Cys
1 5 10

<210> SEQ ID NO 100
<211> LENGTH: 10
<212> TYPE: PRT
<213> ORGANISM: Artificial Sequence
<220> FEATURE:
<223> OTHER INFORMATION: Synthesized

<400> SEQUENCE: 100

Ser Ile Cys Arg Lys Ala His Tyr Asn Cys
1 5 10

<210> SEQ ID NO 101
<211> LENGTH: 10
<212> TYPE: PRT
<213> ORGANISM: Artificial Sequence
<220> FEATURE:
<223> OTHER INFORMATION: Synthesized

<400> SEQUENCE: 101

Ser His Cys Pro Gln Asp Arg Lys Tyr Cys
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthesized

<400> SEQUENCE: 102

Ser Gln Cys Pro Gly Glu Thr Lys Gln Cys
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthesized

<400> SEQUENCE: 103

Ser Pro Cys Gln Arg Gly His Met Phe Cys
1               5                   10

<210> SEQ ID NO 104
<211> LENGTH: 8
<212> TYPE: PRT
<213> ORGANISM: Artificial Sequence
<220> FEATURE:
<223> OTHER INFORMATION: Synthesized

<400> SEQUENCE: 104

Ser Phe Cys Asp Trp Tyr Gly Cys
1               5

<210> SEQ ID NO 105
<211> LENGTH: 8
<212> TYPE: PRT
<213> ORGANISM: Artificial Sequence
<220> FEATURE:
<223> OTHER INFORMATION: Synthesized

<400> SEQUENCE: 105

Ser Leu Cys Phe Asp Asn Gly Cys
1               5

<210> SEQ ID NO 106
<211> LENGTH: 7
<212> TYPE: PRT
<213> ORGANISM: Artificial Sequence
<220> FEATURE:
<223> OTHER INFORMATION: Synthesized

<400> SEQUENCE: 106

Ser His Asp Cys Tyr Glu Cys
1               5

<210> SEQ ID NO 107
<211> LENGTH: 7
<212> TYPE: PRT
<213> ORGANISM: Artificial Sequence
<220> FEATURE:

-continued

```
<223> OTHER INFORMATION: Synthesized

<400> SEQUENCE: 107

Ser Trp Cys Asp Tyr Arg Cys
1               5
```